US010562853B2

(12) United States Patent
Sniecikowska et al.

(10) Patent No.: US 10,562,853 B2
(45) Date of Patent: Feb. 18, 2020

(54) COMPOUNDS FOR TREATING DISORDERS SENSITIVE TO SEROTONINERGIC REGULATION CONTROLLED BY THE 5-HT1A RECEPTORS

(71) Applicants: NEUROLIXIS, Labruguiere (FR); UNIVERSITE JAGELLONE, Cracow (PL)

(72) Inventors: Joanna Sniecikowska, Wieliczka (PL); Adam Bucki, Wieliczka (PL); Adrian Newman-Tancredi, Castres (FR); Mark Andrew Varney, Dana Point, CA (US)

(73) Assignees: NEUROLIXIS, Labruguiere (FR); UNIVERSITE JAGELLONE, Cracow (PL)

( * ) Notice: Subject to any disclaimer, the term of this patent is extended or adjusted under 35 U.S.C. 154(b) by 0 days.

(21) Appl. No.: 16/312,847

(22) PCT Filed: Jun. 23, 2017

(86) PCT No.: PCT/EP2017/065585
§ 371 (c)(1),
(2) Date: Dec. 21, 2018

(87) PCT Pub. No.: WO2017/220799
PCT Pub. Date: Dec. 28, 2017

(65) Prior Publication Data
US 2019/0194132 A1    Jun. 27, 2019

(30) Foreign Application Priority Data
Jun. 24, 2016 (EP) .................................. 16305769

(51) Int. Cl.
| | |
|---|---|
| C07D 211/38 | (2006.01) |
| C07D 401/12 | (2006.01) |
| C07D 405/12 | (2006.01) |
| A61P 25/14 | (2006.01) |
| A61P 25/22 | (2006.01) |
| A61P 25/24 | (2006.01) |
| C07D 401/14 | (2006.01) |

(52) U.S. Cl.
CPC ............ *C07D 211/38* (2013.01); *A61P 25/14* (2018.01); *A61P 25/22* (2018.01); *A61P 25/24* (2018.01); *C07D 401/12* (2013.01); *C07D 401/14* (2013.01); *C07D 405/12* (2013.01)

(58) Field of Classification Search
CPC .... C07D 211/92; C07D 401/12; C07D 211/38
See application file for complete search history.

(56) References Cited

U.S. PATENT DOCUMENTS

| | | | | |
|---|---|---|---|---|
| 6,448,268 | B1 * | 9/2002 | Vacher ................. | C07D 401/12 514/318 |
| 2014/0135310 | A1 * | 5/2014 | Kolaczkowski ...... | C07D 403/06 514/210.21 |

FOREIGN PATENT DOCUMENTS

| | | | | |
|---|---|---|---|---|
| EP | 2 058 306 A1 | 5/2009 | | |
| EP | 2058306 A1 * | 5/2009 | ........... | C07D 401/12 |
| WO | WO 98/22459 A1 | 5/1998 | | |
| WO | WO-9822459 A1 * | 5/1998 | ........... | C07D 211/38 |
| WO | WO 00/21953 A1 | 4/2000 | | |
| WO | WO-0021953 A1 * | 4/2000 | ........... | C07D 401/12 |

OTHER PUBLICATIONS

A. Leentjens et al., 15 International Journal of Geriatric Psychiatry (2000) (Year: 2000).*
B. Vacher et al., 41 Journal of Medicinal Chemistry (1998) (Year: 1998).*
J. Sniecikowska et al., 62 Journal of Medicinal Chemistry, 2750-2771 (2019) (Year: 2019).*
International Search Report (PCT/ISA/210) issued in PCT/EP2017/065585, dated Aug. 2, 2017.
Written Opinion of the International Searching Authority (PCT/ISA/237) issued in PCT/EP2017/065585, dated Aug. 2, 2017.
Albert et al., "Serotonin-prefrontal cortical circuitry in anxiety and depression phenotypes: pivotal role or pre—and post-synaptic 5-HT1A receptor expression," Frontiers in Behavioral Neuroscience, vol. 8, Article 199, Jun. 6, 2014, pp. 1-13.
Celada et al., "Serotonin 5-HT1A Receptors as Targets for Agents to Treat Psychiatric Disorders: Rationale and Current Status of Research," CNS Drugs, vol. 27, Jun. 12, 2013, 14 pages.
European Search Report for European Application No. 16305769, completed Aug. 3, 2016.
Hamik et al., "Analysis of Tandospirone (SM-3997) Interactions with Neurotransmitter Receptor Binding Sites," Biol. Psychiatry, vol. 28, 1990, pp. 99-109.
Iderberg et al., "Activity of Serotonin 5-HT1A receptor 'biased agonists' in rat models of Parkinson's disease and L-DOPA-induced dyskinesia," Neuropharmacology, vol. 93, 2015 (published online Jan. 31, 2015), pp. 52-67.
International Search Report for International Application No. PCT/EP2017/065585, dated Aug. 2, 2017.

(Continued)

*Primary Examiner* — Alexander R Pagano
(74) *Attorney, Agent, or Firm* — Birch, Stewart, Kolasch & Birch, LLP

(57) ABSTRACT

The invention concerns compounds that possess a high affinity at 5-$HT_{1A}$ receptors and an agonist efficacy, as measured by Emax values from a cellular activation assay, that is higher than that of the compounds described in prior art. The capacity of the compounds of the invention to activate an effector protein complex is higher than that the most efficacious agonist described in prior art. Compounds of the invention also exhibit an exceptionally high selectivity (Ki ratio greater than 1000-fold) with respect, in particular, to dopamine D2 receptors and adrenergic receptors of the alpha1 subtype. This selectivity which constitutes a great advantage since it means that the compounds will avoid inducing (central and peripheral) effects associated with activating or inhibiting such receptors.

29 Claims, 6 Drawing Sheets

(56) References Cited

OTHER PUBLICATIONS

Koek et al., "5-HT1A receptor activation and antidepressant-like effects: F 13714 has high efficacy and marked antidepressant potential," European Journal of Pharmacology, vol. 420, 2001, pp. 103-112.

Koek et al., "F 11440, a Potent, Selective, High Efficacy 5-HT1A Receptor Agonist with Marked Anxiolytic and Antidepressant Potential," The Journal of Pharmacology and Experimental Therapeutics, vol. 287, No. 1, 1998, pp. 266-283.

Kolaczkowski et al., "Novel Arylsulfonamide Derivatives with 5-HT6/5-HT7 Receptor Antagonism Targeting Behavioral and Psychological Symptoms of Dementia," Journal Medicinal Chemistry, Dec. 10, 2013, 15 pages.

McCreary et al., "Serotonin 5-HT1A Receptors and Antipsychotics—An Update in Light of New Concepts and Drugs," Current Pharmaceutical Design, vol. 21, No. 26, 2015, pp. 3725-3731.

Ohno et al., "New insight into the therapeutic role of the serotonergic system in Parkinson's disease," Progress in Neurobiology, vol. 134, 2015 (published online Oct. 9, 2015), pp. 104-121.

Pauwels et al., "Activity of Serotonin (5-HT) Receptor Agonists, Partial Agonists and Antagonists at Cloned Human 5-HT1A Receptors that are Negatively Coupled to Adenylate Cyclase in Permanently Transfected Hela Cells," Biochemical Pharmacology, vol. 45, No. 2, 1993, pp. 375-383.

Porsolt et al., "Behavioral Despair in Rats: A New Model Sensitive to Antidepressant Treatments," European Journal of Pharmacology, vol. 47, 1978, pp. 379-391.

Prinssen et al., "5-HT1A receptor activation and anti-cataleptic effects: high-efficacy agonists maximally inhibit haloperidol-induced catalepsy," European Journal of Pharmacoloy, vol. 453, 2002, pp. 217-221.

\* cited by examiner

FIGURE 2A – Scheme 1 :
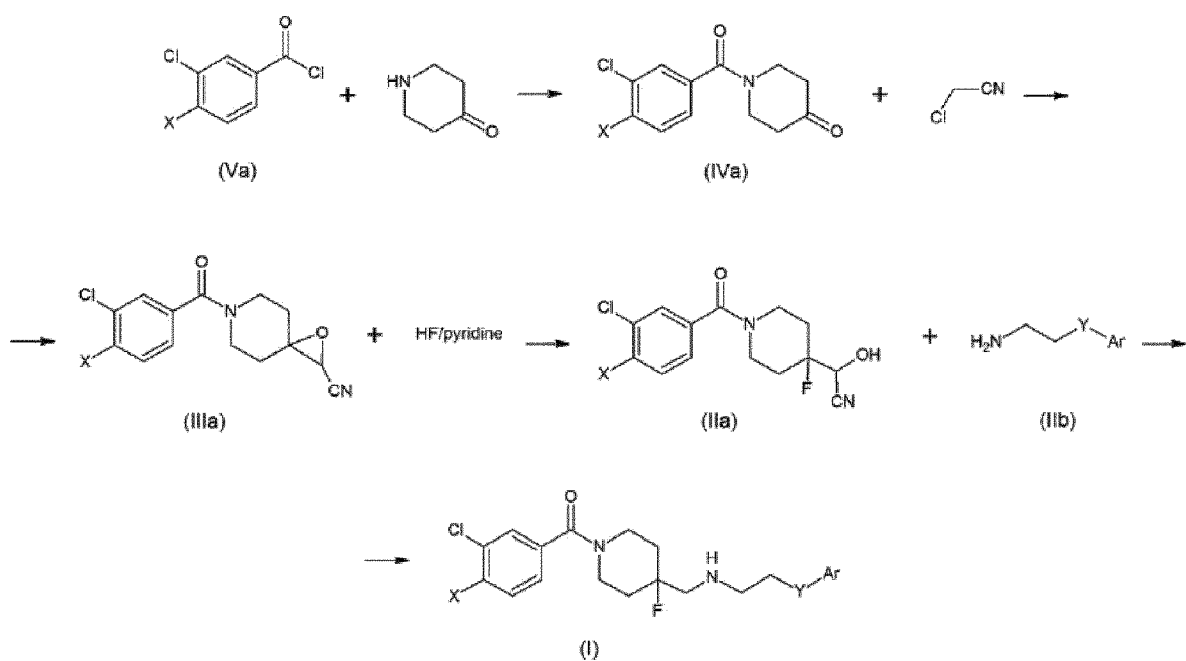

FIGURE 2 B - Scheme 2 :
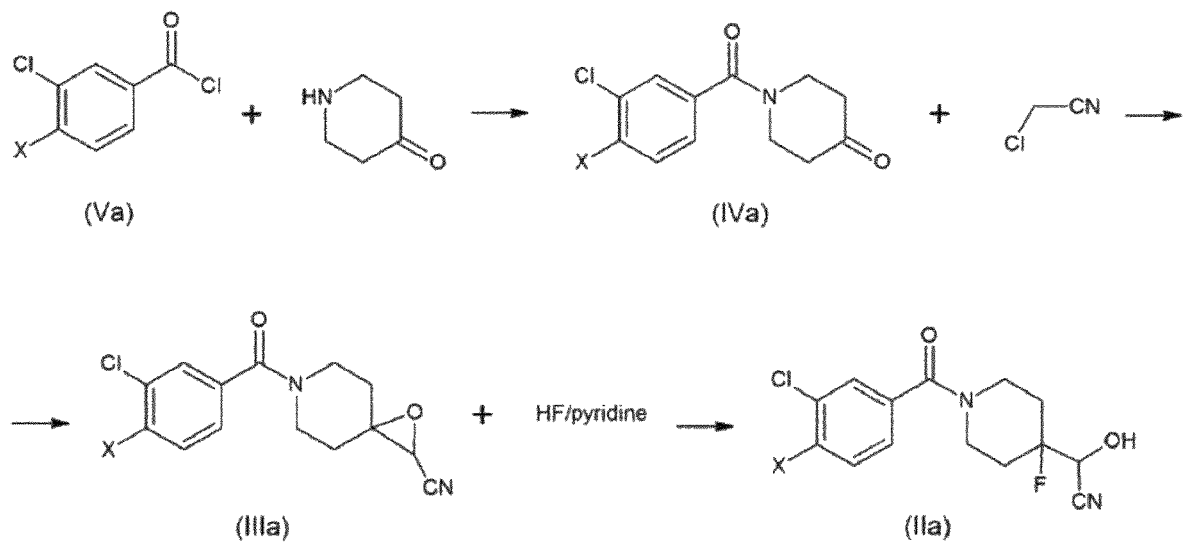
FIGURE 2 C - Scheme 3 :
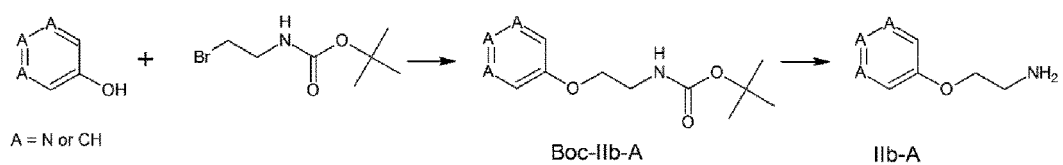

FIGURE 2 D - Scheme 4 :
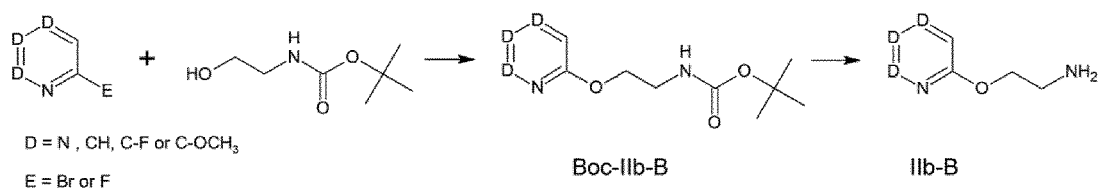
FIGURE 2 E - Scheme 5 :
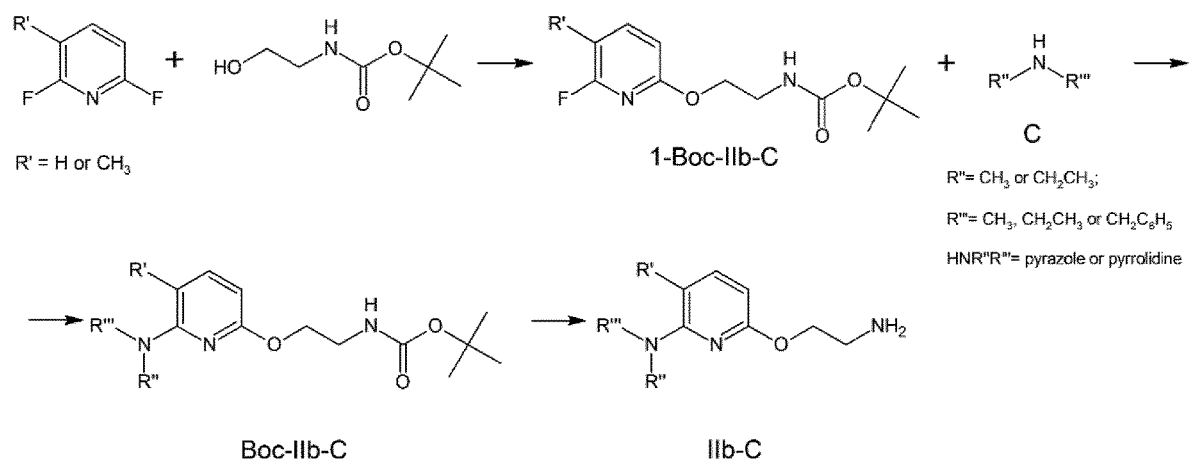

FIGURE 2 F - Scheme 6 :
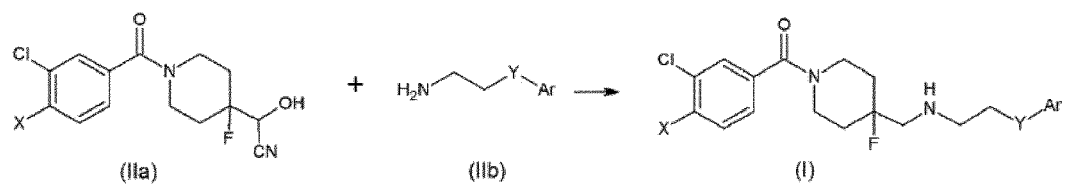
FIGURE 2 G - Scheme 7 :
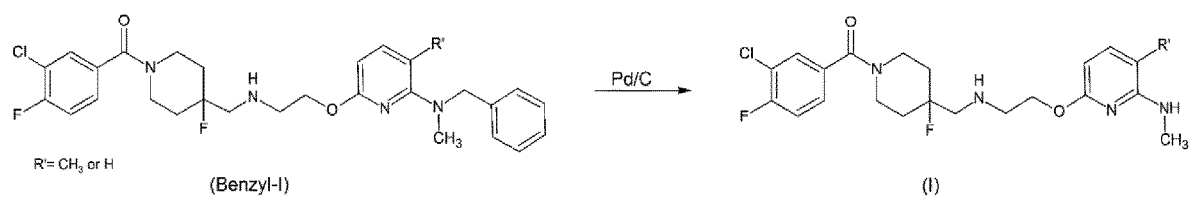
FIGURE 2 H – Scheme 8 :
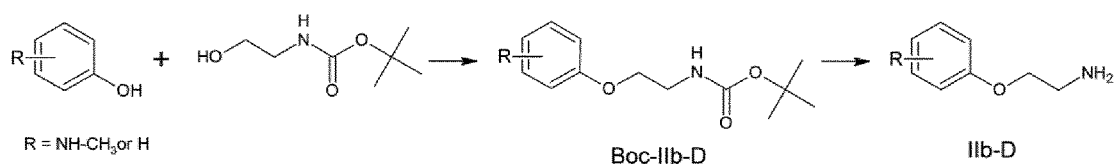

FIGURE 2I – Scheme 9
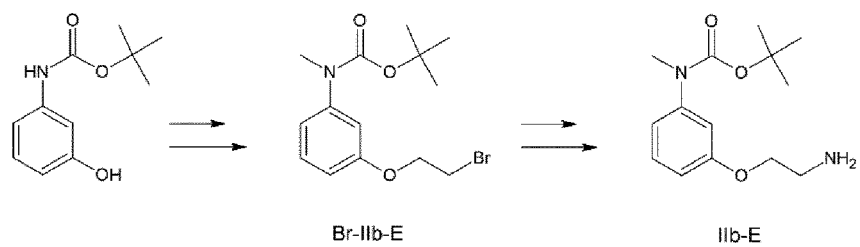
FIGURE 2J – Scheme 10
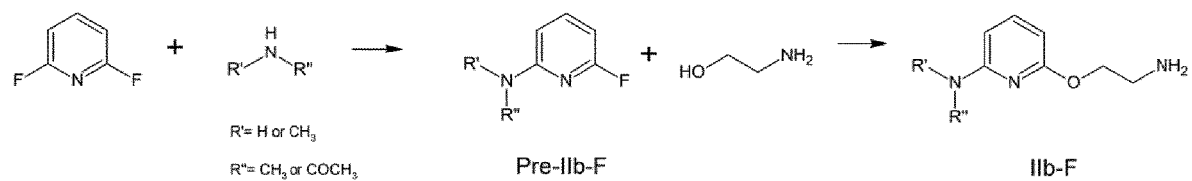
FIGURE 2K – Scheme 11
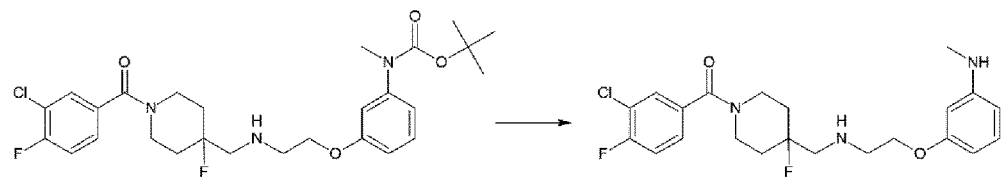

COMPOUNDS FOR TREATING DISORDERS SENSITIVE TO SEROTONINERGIC REGULATION CONTROLLED BY THE 5-HT1A RECEPTORS

Serotonin 5-$HT_{1A}$ receptors are widely expressed in the central nervous system and constitute attractive targets for disorders involving serotonergic function. Indeed, 5-$HT_{1A}$ agonists may be useful for treating several central nervous system disorders (Albert et al., 2014; Celada et al., 2013; McCreary and Newman-Tancredi, 2015; Ohno et al., 2015). Although a very large number of compounds have been claimed as having agonist properties on receptors of the 5-$HT_{1A}$ subtype, only two are clinically available (i.e. buspirone: Europe and United States, and tandospirone: Japan). However, these two compounds belong to the same chemical family (i.e. arylpiperazine) and have relatively similar pharmacological profiles.

Indeed, they behave as partial agonists at 5-$HT_{1A}$ receptors, and do not fully activate the receptors, even when administered at high doses (Hamik et al., 1990; Pauwels et al., 1993; Prinssen et al., 2002). The partial agonist property of these compounds is likely a limiting factor at a therapeutic level. Indeed, high agonist efficacy is necessary for activity in various models of therapeutic activity, including antidepressant-like properties (Forced Swim Test) (Koek et al., 2001), reversal of neuroleptic-induced catalepsy(Prinssen et al., 2002) and inhibition of L-DOPA-induced dyskinesias (Iderberg et al., 2015).

Given the large therapeutic potential of compounds having agonist activity for the 5-$HT_{1A}$ receptors and the absence of drugs whose efficacy approaches that of serotonin, the discovery of novel structures having 5-$HT_{1A}$ agonist properties superior to that of the known ligands is highly desirable.

The Applicant has discovered that several compounds of the formula (I) interact with high affinity at the serotoninergic receptors of the 5-$HT_{1A}$ subtype, on which they behave as high efficacy, selective agonists. As such, the compounds of the invention are potentially useful for treating disorders sensitive to serotoninergic regulation controlled by the 5-$HT_{1A}$ receptors. The field of application of the present invention relates to treatment and/or prevention of depression, the treatment and/or prevention of major depressive disorders, the treatment and/or prevention of anxiety, the treatment the treatment and/or prevention of bipolar depression.

In addition, agonists of the serotonin 5-hydroxytryptamine 5-$HT_{1A}$ receptor have been shown to ameliorate and/or prevent some aspects of movement disorders, such as extrapyramidal side effects associated with neuroleptics treatment and dyskinesia that arise from long-term Levodopa therapy in Parkinson's disease.

The closest prior art is represented by compounds of the pyridin-2-ylmethylamine type (WO 98/22459) corresponding to the following general formula:

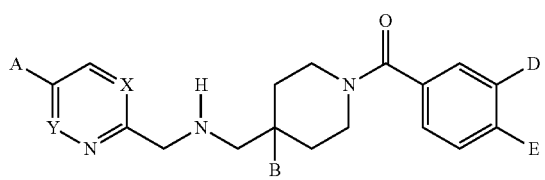

Wherein X represents a carbon atom linked to a hydrogen atom (CH) or a nitrogen atom; Y represents a carbon atom linked to a hydrogen atom (CH) or a nitrogen atom; A represents a methyl, fluoromethyl, cyano, hydroxyl or methoxy radical or a chlorine or fluorine atom, with the proviso, that when A is a methyl radical (CH3 and X and Y simultaneously represent a carbon atom linked to a hydrogen atom, then B necessarily represents a chlorine atom; B represents a chlorine atom or a fluorine atom; D represents a hydrogen atom, a chlorine atom, a fluorine atom, a cyano group or a trifluoromethyl group, E represents a hydrogen, fluorine or chlorine atom.

The compounds of the invention, like those claimed in WO 98/22459, have affinity for 5-$HT_{1A}$ receptors, as measured by Ki values derived from radioligand binding experiments. However, some of the compounds of the invention possess an affinity at 5-HT1A receptors that is an order of magnitude greater than F13640 (befiradol). Furthermore, entirely surprisingly, the structural modifications introduced into the compounds of the invention give them an agonist efficacy, as measured by Emax values from a cellular activation assay, that is higher than that of the compounds described in WO 98/22459. Thus, it is shown, in vitro, that the capacity of several compounds of the invention to activate an effector protein complex is higher than that the most efficacious agonist described in patent WO 98/22459 (befiradol) et Table 1. Compounds (I) also exhibit an exceptionally high selectivity (Ki ratio greater than 1000-fold) with respect, in particular, to dopamine D2 receptors and adrenergic receptors of the alpha1 subtype. This selectivity which constitutes a great advantage since it means that the compounds will avoid inducing (central and peripheral) effects associated with activating or inhibiting such receptors.

The major interest of the compounds of the invention thus lies in their particular capacity to very efficaciously and/or highly selectively activate the receptors of the 5-HT1A subtype; this property is advantageous since it opens up new therapeutic perspectives in human clinical medicine in fields for which there is a great therapeutic need and for which the clinically available 5-HT1A agonists are not effective, for instance the treatment of depressive disorders and movement disorders. As used herein, the term "movement disorder" refers to a condition of the nervous system that affects the intentional ability to produce and/or control body movements or postures. As examples, mention may be made of dyskinesia, akinesia, bradykinesia, tardive dyskinesia, dopamine replacement therapy induced dyskinesia, levodopa induced dyskinesia, ataxia, akathisia, dystonia, essential tremor, myoclonus, chorea, ballismus, athetosis and tics. Movement disorders can also refer to Parkinson's disease, Huntington's disease, Tourette's syndrome, Rett syndrome, Wilson's disease, Machado-Joseph disease, restless leg syndrome.

Accordingly, the present invention is directed to novel compound represented by the general formula (I):

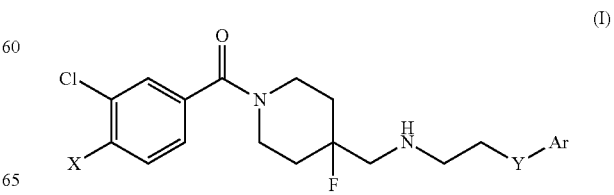

or a pharmaceutically acceptable salt and/or solvate thereof, wherein:

X represents a halo, in particular Cl or F;
Y represents O, S, $CH_2$ or NH, particularly O, S or NH, more particularly O or S; and
Ar is selected from the group consisting of aryl, heterocycloalkyl-fused aryl or heteroaryl, said group being optionally substituted.

In one embodiment the compound of the invention is a compound according to general formula (I) or a pharmaceutically acceptable salt and/or solvate thereof, wherein:

X represents a halo, in particular Cl or F;
Y represents O, S, or NH, in particular O or S, more particularly O and
Ar is selected from the group consisting of aryl, heterocycloalkyl-fused aryl or heteroaryl, said group being optionally substituted with one or several, preferably one or two, groups selected from: halo, preferably F or Cl, —$OR_1$, —$NR_2R_3$, —$NR_4COR_5$, —$NR_6C(O)OR_7$, —$SR_8$, —$S(O)R_9$, —$SO_2R_{10}$, —$SO_2NR_{11}R_{12}$, —$OCOR_{13}$, —$CO_2R_{14}$, —$CONR_{15}R_{16}$, —$OCO_2R_{17}$, —$OCONR_{18}R_{19}$, —$COR_{20}$, —$CF_3$, nitro (—$NO_2$), cyano (—CN) or a group consisting of -($C_1$-$C_6$)alkyl group preferably methyl, heteroaryl preferably pyrazole and heterocycloalkyl preferably pyrrolidine; with $R_1$ to $R_{20}$ being, independently of one another, H, ($C_1$-$C_6$)alkyl group preferably H, methyl or ethyl.

BRIEF DESCRIPTION OF THE DRAWINGS

FIG. 2A presents a general synthesis route for compounds of formula (I).
FIG. 2B presents a general synthesis route for cyanohydrin.
FIG. 2C presents a general synthesis route for compounds of formula IIb-A.
FIG. 2D presents a general synthesis route for compounds of formula IIb-B.
FIG. 2E presents a general synthesis route for compounds of formula IIb-C.
FIG. 2F shows the preparation of compound (I) from compounds IIa and IIb.
FIG. 2G shows the preparation of compound (I) from benzyl intermediates.
FIG. 2H presents a general synthesis route for compounds of formula IIb-D.
FIG. 2I presents a general synthesis route for compounds of formula IIb-E.
FIG. 2J presents a general synthesis route for compounds of formula IIb-F.
FIG. 2K shows the preparation of compound (I) from Boc-protected intermediates.

Figure 1:
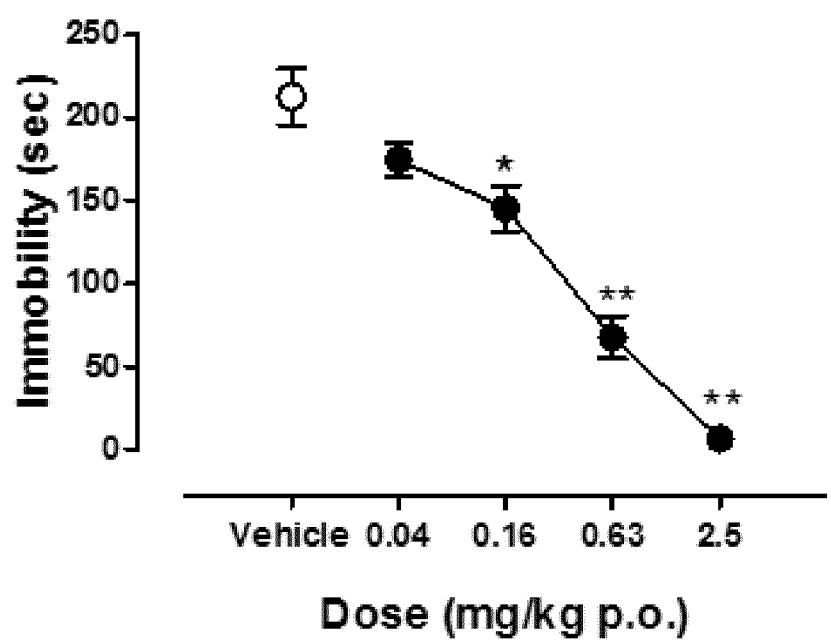
FIG. 1 shows the effects of Compound 18 in the rat Forced Swim Test.

The term "aryl", as used in the present invention, refers to an aromatic hydrocarbon group comprising preferably 6 to 10 carbon atoms and optionally comprising one or more fused rings, such as, for example, a phenyl or naphtyl group. Aryl is any functional group or substituent derived from an aromatic ring, usually an aromatic hydrocarbon, be it phenyl, naphthyl, thienyl, indolyl, for exemple. A simple aryl group is phenyl, $C_6H_5$; it is derived from benzene. The tolyl group, $CH_3C_6H_4$, is derived from toluene (methylbenzene). The xylyl group, $(CH_3)_2C_6H_3$, is derived from xylene (dimethylbenzene), while the naphthyl group, $C_{10}H_7$, is derived from naphthalene.

The term "heteroaryl" as used in the present invention refers to an aromatic hydrocarbon monocycle or bicycle (i.e. comprising two fused rings), each cycle having 5 or 6 members, notably 6 members, and 1 to 4, notably 1 or 2, carbon atoms having each been replaced with a nitrogen or oxygen atom, notably a nitrogen atom. A heteroaryl can be notably thiophene, furan, pyrrole, imidazole, pyrazole, oxazole, oxindole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole,2-hydroxybenzimidazole, pyridine, pyrimidine, pyridazine, pyrazine, triazine, quinoline, isoquinoline, quinoxaline, quinazoline, etc. In particular, the heteroaryl is indole, pyridine, pyrimidine, pyridazine, and pyrazine.

The term "heterocycloalkyl" as used in the present invention refers to a saturated hydrocarbon ring having 5 to 7 members, in which one or more, advantageously one or two, carbon atoms have been each replaced with a heteroatom, such as sulphur, nitrogen or oxygen atoms. It can be notably a 1,3-dioxolanyl, 1,4-dioxanyl, tetrahydrofuranyl, piperidinyl, pyrrolidinyl or tetrahydropyranyl group, preferably 1,4-dioxanyl group or pyrrolidinyl.

The term "heterocycloalkyl-fused aryl", as used in the present invention, refers to an aryl group fused with a heterocycloalkyl group. For example, the heterocycloalkyl-fused aryl may be 1,4 benzodioxanyl.

In a preferred embodiment Ar comprises 6 carbon atoms and is a phenyl, a substituted phenyl and Y is O.

In a preferred embodiment Ar is a phenyl substituted with —$NR_4COR_5$ with R4 and R5 being H or C1-C6 alkyl, particularly methyl.

In a preferred embodiment Ar is a phenyl substituted with a halogen, particularly a F or a Cl, particularly a F.

In a preferred embodiment Ar is a phenyl substituted with O-Me.

In another preferred embodiment Ar is a heteroaryl and is a pyridine, particularly a substituted pyridine; or a pyrazine.

When Ar is a pyridine, in a preferred embodiment the pyridine is substituted with a pyrrolidine. In one preferred embodiment Ar is substituted with one or more, preferably one or two groups selected in the group consisting of halogen, —$OR_1$, —$NR_2R_3$, —$NR_4COR_5$,—$SR_8$, R1, R2, R3, R4, R5 and R8 being H, methyl or ethyl.

In one preferred embodiment Ar is a phenyl or a naphtyl group.

In one embodiment, Ar is a heteroaryl group selected in the group consisting of pyrazole, indole, pyridine, pyrimidine, pyridazine, pyrazine. In particular Ar is selected in the group consisting of pyridine, pyrimidine, pyridazine and pyrazine.

In one embodiment, Ar is a heteroclycloalkyl selected in the group consisting of 1,4-dioxanyl, pyrrolidinyl.

In one embodiment, Ar is a heterocycloalkyl-fused aryl and is 1,4 benzodioxanyl.

The purpose of the second aspect of the invention is a compound of formula (I) according to the invention for use as a drug, and a pharmaceutical composition comprising a compound of formula (I) according to the invention and a pharmaceutically acceptable excipient.

The invention also relates to pharmaceutically acceptable water-soluble salts of compound of formula (I), as well as pharmaceutical compositions containing same, and the use of same as a medicament for the treatment and/or prevention of central nervous system disorders.

Examples of conditions, diseases, or neurological or psychiatric disorders according to the invention include major depression, depressive disorders, anxiety, bipolar depression.

The invention also relates to pharmaceutically acceptable water-soluble salts of compound of formula (I), as well as pharmaceutical compositions containing same, and the use of same as a medicament for treating and/or preventing movement disorders.

In one embodiment, movement disorders that can be treated and./or prevented according to the invention include movement disorders such as dyskinesia, akinesia, bradykinesia, tardive dyskinesia, dopamine replacement therapy induced dyskinesia, levodopa induced dyskinesia, ataxia, akathisia, dystonia, essential tremor, myoclonus, chorea, ballismus, athetosis, tics.

In particular, the purpose of this invention is the use of a compound with formula (I) according to the invention or a composition according to the invention, for the preparation of a pharmaceutical composition intended for the treatment and/or prevention of neuropsychiatric disorders such as depression, major depression, depressive disorders, anxiety and bipolar depression.

In a preferred embodiment, the neurologic and neuropsychiatric disorder is major depression.

In a preferred embodiment, the neurologic and neuropsychiatric disorder is movement disorder selected in the group consisting of dyskinesia, particularly L-DOPA-induced dyskinesia, akinesia, bradykinesia, tardive dyskinesia, dopamine replacement therapy induced dyskinesia, levodopa induced dyskinesia, ataxia, akathisia, dystonia, essential tremor, myoclonus, chorea, ballismus, athetosis and tics, Parkinson's disease, Huntington's disease, Tourette's syndrome, Rett syndrome, Wilson's disease, Machado-Joseph disease, restless leg syndrome.

In a preferred embodiment, the neurologic and neuropsychiatric disorder is anxiety.

In another embodiment, the invention relates to a compound of formula (I) for its use as a drug.

In another embodiment, the invention relates to a compound of formula (I) for its use as a drug for the treatment and/or prevention of depression, more particularly major depression.

In another embodiment, the invention relates to a compound of formula (I) for its use as a drug for the treatment and/or prevention of depressive disorders.

In another embodiment, the invention relates to a compound of formula (I) for its use as a drug for the treatment and/or prevention of movement disorders.

In another embodiment, the invention relates to a compound of formula (I) for its use as a drug for the treatment and/or prevention of a bipolar type major depression according to the DSM IV, particularly a major recurrent depressive disorder.

In another embodiment, the invention relates to a compound of formula (I) for its use as a drug for the treatment and/or prevention of major depression with severity evaluated with a score of more than 26 using the HAMD ("Hamilton Depression Scale") scale, or with a score of more than 35 on the MADRS (Montgomery and Asberg Depression Rating Scale) scale.

In another embodiment, the invention relates to a compound of formula (I) for its use as drug for the treatment and/or prevention of L-DOPA-induced dyskinesia.

In another embodiment, the invention relates to a compound of formula (I) for its use as drug for the treatment and/or prevention of anxiety.

The invention also relates to a method for treating neurological or psychiatric conditions, diseases or disorders, consisting of administering to a patient who requires treatment a compound of formula (I) in a therapeutically effective quantity.

The compounds of formula (I) may be prepared via reaction of a cyanohydrin (IIa) with an appropriate amine (IIb), or their salts, in the presence of sodium cyanoborohydride as reducing agent and optionally a base according to the general synthesis route (FIG. 2A—scheme 1)

In the first step, the commercially available 4-piperidone is acylated by the appropriate derivative (Va) in the presence of triethylamine. Then a Darzens reaction between the obtained benzoylpiperidin-4-ones derivatives (IVa) and an acetonitrile halide (A. Jonczyk, Tetrahedron Lett. (1972) 23, 2395-96) gives the corresponding cyanoepoxides (IIIa). The epoxide (IIIa) undergoes a regioselective ring opening reaction with hydrogen fluoride-pyridine complex (Vacher B. J. Med. Chem. 1999, 42, 1648- 1660; Suga H. Tetrahedron 1990 46 (12) 4247-4254) to afford the cyanohydrins of formula IIa.

The compounds of formula (I) can be purified according to one or more methods chosen from crystallization and/or liquid-phase chromatographic techniques. They may then, if so desired, be salified using a pharmaceutically acceptable mineral or organic acid.

The general synthesis route for preparation of cyanohydrin compound is illustrated in the FIG. 2B—Scheme 2 (preparation of cyanohydrin IIa) and is detailed in the example part of the present invention.

The amine compound (IIb) can be synthetized while some are available commercially.

The following amine compounds (IIb) are commercially available:
2-phenoxyethanamine (IIb-1)
N-[3-(2-aminoethoxy)phenyl]acetamide (IIb-2)
2-(3-chlorophenoxy)ethanamine (IIb-3)
2-(3-fluorophenoxy)ethanamine (IIb-4)
2-(2-methoxyphenoxy)ethanamine (IIb-5)
2-(3-methoxyphenoxy)ethanamine (IIb-6)
2-(4-methoxyphenoxy)ethanamine (IIb-7)
2-[2-(methylsulfanyl)phenoxy]ethanamine (IIb-8)
2-(2,3-dihydro-1,4-benzodioxin-6-yloxy)ethanamine (IIb-9)
2-(quinolin-8-yloxy)ethanamine (IIb-10)
2-(pyridin-2-yloxy)ethanamine (IIb-11)
2-(pyridin-3-yloxy)ethanamine (IIb-12)
2-(pyridin-4-yloxy)ethanamine (IIb-13)
2-[(5-methylpyridin-2-yl)oxy]ethanamine (IIb-14)
2-[(5-chloropyridin-2-yl)oxy]ethanamine (IIb-15)
2-[(3-methoxypyridin-2-yl)oxy]ethanamine (IIb-16)
2-{[4-(trifluoromethyl)pyridin-2-yl]oxy}ethanamine (IIb-17)
2-(pyrimidin-2-yloxy)ethanamine (IIb-18)
2-(pyrimidin-4-yloxy)ethanamine (IIb-19)
2-[(5-methylpyrimidin-2-yl)oxy]ethanamine (IIb-20)
2-(pyridazin-3-yloxy)ethanamine (IIb-21)
2-(pyridin-2-ylsulfanyl)ethanamine (IIb-22)
2-[(3-methoxyphenyl)sulfanyl]ethanamine (IIb-23)
2-((1H-indol-4-yl)oxy)ethanamine (IIb-24)
3-(2-aminoethoxy)-N,N-dimethylaniline (IIb-25)
2-(3-(trifluoromethyl)phenoxy)ethanamine (IIb-26)
3-(2-aminoethoxy)benzamide (IIb-27)
2-(2-aminoethoxy)benzamide (IIb-28)
N1-phenylethane-1,2-diamine (IIb-29)
N1-(pyridin-2-yl)ethane-1,2-diamine (IIb-30)
3-(pyridin-2-yl)propan-1-amine (IIb-31)
4-(2-aminoethoxy)indolin-2-one (IIb-32)

2-(indolin-4-yloxy)ethanamine (IIb-33)
3-phenylpropan-1-amine (IIb-34)
2-((2,2-dimethyl-2,3-dihydrobenzofuran-7-yl)oxy)ethanamine (IIb-35)
2-(2-fluorophenoxy)ethanamine (IIb-36)
2-(2-chlorophenoxy)ethanamine(IIb-37)
2-(m-tolyloxy)ethanamine (IIb-38)
2-(4-fluorophenoxy)ethanamine (IIb-39)
2-(4-chlorophenoxy)ethanamine(IIb-40)
2-((6-methoxypyridin-2-yl)oxy)ethanamine (IIb-41)
2-((5-methoxypyridin-2-yl)oxy)ethanamine (IIb-42)
2-((5-fluoropyridin-2-yl)oxy)ethanamine (IIb-43)
2-((4-fluoropyridin-2-yl)oxy)ethanamine (IIb-44)
2-((6-(trifluoromethyl)pyridin-2-yl)oxy)ethanamine (IIb-45)
2-((6-chloropyridin-2-yl)oxy)ethanamine (IIb-46)
2-((6-methylpyridin-2-yl)oxy)ethanamine (IIb-47)

The preparation of amine compounds (IIb) can be achieved according to different routes leading to three types of amine compounds, namely IIb IIb-A, IIb-B, IIb-C, IIb-D, IIb-E and IIb-F.

The preparation of amine compounds IIb-A can be made according to the general synthesis route depicted in the FIG. 2 C—Scheme 3

The appropriate phenol (1.0 eq, 3.125 mmol) was dissolved in N,N-dimethylformamide (8.5 mL) at room temperature, sodium hydride (1.1 eq, 3.44 mmol) was added in one portion and mixture stirred at room temperature for 10 minutes. 2-Boc-aminoethyl bromide (1.1 eq, 3.44 mmol) in N,N-dimethylformamide (2 mL) was added dropwise and mixture stirred at room temperature for 48 h. After stirring, mixture was quenched with brine, diluted with Rochelle's salt, aqueous extracted with ethyl acetate, organics dried over magnesium sulfate, filtered and concentrated in vacuum. Crude product was purified by flash chromatography (diethyl ether/dichloromethane/methanol 2:7:1) to yield pure product as a yellow oil (yield 27-31%). The appropriate product of formula Boc-IIb-A (0.83 mmol) was poured with 0.1M hydrochloric acid in ethyl acetate (15 mL), and stirred for 24 h. Then, the mixture was filtered giving pure hydrochloride as a white solid. (yield 78-95%).

The preparation of amine compounds IIb-B can be made according to the general synthesis route depicted in the FIG. 2 D—Scheme 4

Tert-butyl-2-hydroxyethyl carbamate (0.95 eq, 8.33 mmol) was dissolved in THF (20 mL), cooled to 0° C., and then sodium hydride (0.95 eq, 8.33 mmol, 60% dispersion) was added in one portion. Mixture was removed from ice bath and allowed to stir at room temperature for 15 minutes. Then, the mixture was re-cooled in ice bath, the appropriate halogen derivative (1.0 eq, 8.77 mmol) was added portionwise over 5 minutes, and mixture was allowed to warm to RT with stirring for 20 hours. The mixture was then cooled to 0° C., quenched with ammonium chloride (saturated, aq), aqueous was extracted with ethyl acetate, organics dried over magnesium sulfate, filtered and concentrated in vacuum to yield crude product (formula Boc-IIb-B), and then used in next reaction without further purification. The appropriate product of formula Boc-IIb-B (0.83 mmol) was poured with 0.1M hydrochloric acid in ethyl acetate (15 ml), and stirred for 24 hours. Then, the mixture was filtered giving pure hydrochloride as a white solid (total yield 31-69%).

The preparation of amine compounds IIb-C can be made according to the general synthesis route depicted in the FIG. 2 E—Scheme 5

Tert-butyl-2-hydroxyethyl carbamate (0.9 eq, 26.09 mmol) was dissolved in THF (40 mL), cooled to 0° C., and then sodium hydride (0.9 eq, 26.09 mmol, 60% dispersion) added in one portion. The mixture was removed from ice bath and allowed to stir at room temperature for 15 minutes. Then, the mixture was added portionwise to cold solution of appropriate halogen derivative in THF (10 mL), and allowed to warm to RT with stirring for 20 hours. The resulting mixture was cooled to 0° C., quenched with ammonium chloride (saturated, aq), aqueous was extracted with ethyl acetate, organics dried over magnesium sulfate, filtered and concentrated in vacuum to yield crude product (formula 1-Boc-IIb-C), and then used in next reaction without further purification. The appropriate product of formula Boc-IIb-C (0.83 mmol) was poured with 0.1M hydrochloric acid in ethyl acetate (15 mL), and stirred for 24-48 hours. Then, the mixture was filtered giving pure hydrochloride as a white solid. (total yield 31-69%).

The preparation of amine compounds IIb-D can be made according to the general synthesis route depicted in the FIG. 2 H—Scheme 8

Tert-butyl-2-hydroxyethyl carbamate (1.0 eq., 16.26 mmol) was dissolved in THF (60 mL) at room temperature, appropriate phenol (1 eq., 16.26 mmol) was added, followed by triphenylphosphine (1 eq., 16.26 mmol). Mixture cooled to 0° C., followed by dropwise addition of DIAD (1 eq., 16.26 mmol) over 10 minutes. Mixture then allowed to warm to room temperature and stirred for 24 hours. After that time, the mixture was warmed to 50° C. and stirred for additional 24 hours. The resulting mixture was concentrated in vacuo, and crude residue was purified via flash chromatography (dichloromethane/methanol 98:2 and then hexane/diethyl ether/ethyl acetate 5:2:3) to yield pure product as a pale yellow oil (yield 25%). The appropriate product of formula Boc-IIb-D (1.45 mmol) was poured with 1 M hydrochloric acid in ethyl acetate (25 mL), and stirred for 16 h. Then, the mixture was filtered giving pure hydrochloride as a white-pink solid. (yield 65%).

The preparation of amine compound IIb-E can be made according to the general synthesis route depicted in FIG. 2 I—Scheme 9

To a solution of 1,2-dibromoethane (5.0 eq., 23.93 mmol) and potassium carbonate (5.0 eq., 23.93 mmol) in acetone, tert-butyl (3-hydroxyphenyl)carbamate was added dropwise. The mixture was warmed to 50° C. and stirred for 48 h. After that time, the resulting mixture was concentrated in vacuo and subsequently quenched with brine. The aqueous was extracted with dichloromethane, organics combined and dried over magnesium sulfate, filtered and concentrated to crude product. Purification via flash chromatography (hexane/ethyl acetate 9:1) yielded pure product as a beige solid (53%). Then, the obtained tert-butyl (3-(2-bromoethoxy)phenyl)carbamate (1 eq., 2.03 mmol) was added to a solution of sodium hydride (1.2 eq., 2.44 mmol) in THF (13 mL) and stirred at 0° C. for 30 minutes. Then, methyl iodide (1.2 eq., 2.44 mmol) was added dropwise and the reaction mixture was warmed to room temperature and stirred additionally for 1 h. After that time, the resulting mixture was concentrated in vacuo and subsequently quenched with water. The aqueous was extracted with ethyl acetate, organics combined and dried over magnesium sulfate, filtered and concentrated to yield crude product (Br-IIb-E) and then used in next reaction without further purification (yield 94%). The obtained tert-butyl (3-(2-bromoethoxy)phenyl)(methyl)carbamate (1 eq., 2.02 mmol) (Br-IIb-E) was dissolved in dry DMF and added dropwise to a solution of potassium phtalimide (1.1 eq., 2.23 mmol) and ether 18-crown-6 (0.03 eq., 0.061 mmol) in dry DMF. The mixture was stirred for 3 h at 50° C. After that time, reaction mixture was cooled to a room temperature and was poured into water (16 mL), stirred for 1 h, precipitate was filtered off, washed with water and dired on the air affording phtalimide derivative (82% yield). The mixture of phtalimide derivative (1 eq., 1.634 mmol), 40% MeNH2 (16 mL) was added, and the resulting reaction mixture was stirred at 50° C. for 2 h. Next, the reaction mixture was cooled to the room temperature and a solution of 10% KOH (16 mL) was added and the resulted mixture was stirred for additional 1 h. After that time, the reaction mixture was refrigerated overnight, the obtained oil was rinsed with water and dried in vacuum to crude product. Purification via flash chromatography (dichloromethane/methanol/ammonia 9:1:0.1) yielded pure product as a colorless solid (IIb-E) (88%).

The preparation of amine compounds IIb-F can be made according to the general synthesis route depicted in the FIG. 2 J—Scheme 10

In a microwave tube 2,6-difluoropyridine (1 eq., 5.47 mmol) was placed and was cooled to 0° C. and then, 2M solution of appropriate amine (or amide) in THF (1.5 eq., 8.21 mmol) was added dropwise. The reaction mixture was heated at 150° C. for 20 min in the microwave reactor. Water was added and the mixture was extracted with ethyl acetate, the organic layers were combined and dried over magnesium sulfate, filtered and concentrated to yield crude product (Pre-IIb-F) and then used in next reaction without further purification (yield 70-84%). The obtained appropriate 6-fluoro-pyridin-2-amine (Pre-IIb-F) (1 eq., 1.77 mmol) was added dropwise to a solution of 2-aminoethanol (3 eq., 5.32 mmol) and sodium hydride (3 eq., 5.32 mmol) in dry 1,4-dioxane. The reaction mixture was heated at 90° C. for 20 min in the microwave reactor. Then the resulting mixture was concentrated in vacuo and subsequently quenched with brine. The aqueous was extracted with ethyl acetate, organics combined and dried over magnesium sulfate, the crude mixture was purified by column chromatography over silica gel using chloroform/methanol/ammonia 9:1:0.1 as eluent (yield 65-82%).

INTERMEDIATE COMPOUNDS

Starting Materials of Formula IVa:
IVa-1

1-(3,4-dichlorobenzoyl)piperidin-4-one

The title compound was prepared starting from the 3,4-dichlorobenzoyl chloride.
$^1$H NMR (300 MHz, CDCl$_3$) δ: 7.58 (d, J=1.8 Hz, 1 H), 7.52 (d, J=8.2 Hz, 1 H), 7.31 (dd, J=2.1, 8.2 Hz, 1 H), 3.86 (br. s., 4 H), 2.51 (br. s., 4 H)
MS: 272 [M+H$^+$].
IVa-2

1-(3-chloro-4-fluorobenzoyl)piperidin-4-one

The title compound was prepared starting from the 3-chloro-4-fluorobenzoyl chloride.
$^1$H NMR (300 MHz, CDCl$_3$) δ: 7.56 (dd, J=2.1, 6.9 Hz, 1 H), 7.37 (ddd, J=2.2, 4.6, 8.4 Hz, 1 H), 7.25-7.17 (m, 1 H), 3.87 (br. s., 4 H), 2.51 (br. s., 4 H)
$^{19}$F NMR (282 MHz, CDCl$_3$) δ: −111.50 (s, 1F)
MS: 256 [M+H$^+$].

Starting Materials of Formula IIIa:
IIIa-1

6-(3,4-dichlorobenzoyl)-1-oxa-6-azaspiro[2.5]octane-2-carbonitrile

The title compound was prepared starting from the compound of formula (IVa-1)
$^1$H NMR (300 MHz, CDCl$_3$) δ: 7.59-7.45 (m, 2 H), 7.31-7.19 (m, 1 H), 4.44-4.15 (m, 1 H), 3.82-3.49 (m, 3 H), 3.41 (s, 1 H), 1.99-1.37 (m, 4 H)
$^{13}$C NMR (75 MHz, CDCl$_3$) δ: 168.2, 134.9, 134.6, 133.2, 130.8, 129.2, 126.3, 115.2, 63.1, 60.4, 47.1, 21.0, 14.2
MS: 311 [M+H$^+$].
IIIa-2

6-(3-chloro-4-fluorobenzoyl)-1-oxa-6-azaspiro[2.5]octane-2-carbonitrile

The title compound was prepared starting from the compound of formula (IVa-2)
$^1$H NMR (300 MHz, CDCl$_3$) δ: 7.52 (dd, J=2.1, 6.7 Hz, 1 H), 7.38-7.29 (m, 1 H), 7.24-7.14 (m, 1 H), 4.35-3.70 (m, 2 H), 3.67-3.49 (m, 2 H), 3.41 (s, 1 H), 2.20-1.69 (m, 4 H)
MS: 295 [M+H$^+$].
Starting Materials of Formula IIa:
IIa-1

2-(1-(3,4-dichlorobenzoyl)-4-fluoropiperidin-4-yl)-2-hydroxyacetonitrile

The title compound was prepared starting from the compound of formula (IIIa-1)
$^1$H NMR (300 MHz, CDCl$_3$) δ: 7.54-7.49 (m, 2 H), 7.26-7.22 (m, 1 H), 4.65 (br. s., 1 H), 4.39 (d, J=12.6 Hz, 1 H), 4.29-4.05 (m, 1 H), 3.76 (br. s., 1 H), 3.49 (s, 2 H), 2.21-1.57 (m, 4 H)
$^{19}$F NMR (282 MHz, CDCl$_3$) δ: −170.77 (s, 1F)
MS: 330 [M+H$^+$].
IIa-2

2-(1-(3-chloro-4-fluorobenzoyl)-4-fluoropiperidin-4-yl)-2-hydroxyacetonitrile

The title compound was prepared starting from the compound of formula (IIIa-2)
$^1$H NMR (300 MHz, CDCl$_3$) δ: 7.49 (dd, J=2.1, 6.7 Hz, 1 H), 7.34-7.27 (m, 1 H), 7.24-7.17 (m, 1 H), 4.65 (br. s., 1 H), 4.40 (d, J=12.6 Hz, 1 H), 3.75 (br. s., 1 H), 3.51-3.03 (m, 2 H), 2.19-1.65 (m, 4 H)
$^{13}$C NMR (75 MHz, CDCl$_3$) δ: 168.5, 159.1, 132.0, 129.8, 127.1, 121.8, 117.0, 116.6, 94.5, 92.1, 66.9, 66.5
MS: 315 [M+H$^+$].
Starting Materials of Formula IIb-A, B, C, D, E, F
Starting Materials of Formula IIb-A:
Starting Materials of Formula Boc-IIb-A.
Boc-IIb-A-1 tert-butyl [2-(pyridazin-4-yloxy)ethyl]carbamate

The title compound was prepared starting from the pyridazin-4-ol.
$^1$H NMR (300 MHz, CDCl$_3$) δ: 7.88 (d, J=3.1 Hz, 1 H), 7.68 (d, J=7.7 Hz, 1 H), 6.42 (dd, J=3.2, 7.8 Hz, 1 H), 4.13 (t, J=5.4 Hz, 2 H), 3.53 (q, J=6.0 Hz, 2 H), 1.42 (s, 9 H).
MS: 240 [M+H$^+$]

Boc-IIb-A-2 tert-butyl [2-(pyrimidin-5-yloxy)ethyl]carbamate

The title compound was prepared starting from the pyrimidin-5-ol.
$^1$H NMR (300 MHz, CDCl$_3$) δ: 8.86 (s, 1 H), 8.41 (s, 2 H), 4.13 (t, J=5.1 Hz, 2 H), 3.57 (q, J=5.4 Hz, 2 H), 1.85-1.71 (m, 1 H), 1.44 (s, 9 H).
MS: 240 [M+H$^+$]
Starting Materials of Formula IIb-A
IIb-A-1

2-(pyridazin-4-yloxy)ethanamine hydrochloride

The title compound was prepared starting from the compound of formula (Boc-IIb-A-1)
1H NMR (300 MHz, DMSO-d$_6$) δ: 8.69 (d, J=7.4 Hz, 1 H), 8.43 (br. s., 3 H), 8.24 (d, J=3.1 Hz, 1 H), 6.88 (dd, J=3.2, 7.6 Hz, 1 H), 4.51 (t, J=5.8 Hz, 2 H), 3.34-3.22 (m, 2 H).
MS: 140 [M+H$^+$]
IIb-A-2

2-(pyrimidin-5-yloxy)ethanamine hydrochloride

The title compound was prepared starting from the compound of formula (Boc-IIb-A-2)
1H NMR (300 MHz, CD$_3$OD) δ: 9.09 (s, 1 H), 8.92 (br. s., 2 H), 4.55 (t, J=4.0 Hz, 2 H), 3.48 (br. s., 2 H) NH protons not detected
MS: 140 [M+H$^+$]
Starting Materials of Formula IIb-B:
Starting Materials of Formula Boc-IIb-B.
Boc-IIb-B-1 tert-butyl {2-[(6-fluoropyridin-2-yl)oxy]ethyl}carbamate

The title compound was prepared starting from 2,6-difluoropyridine.
1H NMR (300 MHz, CDCl$_3$) δ: 7.65 (q, J=8.2 Hz, 1 H), 6.60 (dd, J=1.7, 8.1 Hz, 1 H), 6.47 (dd, J=2.4, 7.8 Hz, 1 H), 4.92 (br. s., 1 H), 4.36-4.28 (m, 2 H), 3.51 (q, J=5.2 Hz, 2 H), 1.44 (s, 9 H).
MS: 257 [M+H$^+$]
Boc-IIb-B-2 tert-butyl [2-(pyrazin-2-yloxy)ethyl]carbamate

The title compound was prepared starting from 2-bromopyrazine.
MS: 240 [M+H$^+$]
Boc-IIb-B-3 tert-butyl (2-((4-methoxypyridin-2-yl)oxy)ethyl)carbamate

The title compound was prepared starting from 2-fluoro-4-methoxypyridine.
MS: 269 [M+H$^+$]
Starting Materials of Formula IIb-B.
IIb-B-1

2-[(6-fluoropyridin-2-yl)oxy]ethanamine hydrochloride

The title compound was prepared starting from the compound of formula (Boc-IIb-B-1)
1H NMR (300 MHz, DMSO-d$_6$) δ: 8.28 (br. s., 3 H), 7.96-7.86 (m, 1 H), 6.76 (dt, J=2.1, 7.6 Hz, 2 H), 4.42-4.35 (m, 2 H), 3.18 (t, J=5.4 Hz, 2 H).
MS: 157 [M+H$^+$]
IIb-B-2

2-(pyrazin-2-yloxy)ethanamine hydrochloride

The title compound was prepared starting from the compound of formula (Boc-IIb-B-2)
1H NMR (300 MHz, DMSO-d$_6$) δ: 8.27 (s, 1 H), 8.17 (s, 2 H), 4.21 (t, J=5.8 Hz, 2 H), 2.87 (t, J=5.9 Hz, 2 H).
MS: 240 [M+H$^+$]
IIb-B-3

2-((4-methoxypyridin-2-yl)oxy)ethanamine

The title compound was prepared starting from the compound of formula (Boc-IIb-B-3)
$^1$H NMR (300 MHz, CDCl$_3$) δ: 7.77 (m, 1 H), 7.20 (m, 1 H), 6.69 (m, 1 H), 4.25 (t, J=5.3 Hz, 2 H), 3.80 (s, 3 H), 3.05 (t, J=5.3 Hz, 2 H), 2.00 (s, 2 H)
MS: 169 [M+H$^+$]
Starting Materials of Formula IIb-C:
Starting Materials of Formula 1-Boc-IIb-C
1-Boc-IIb-C-1 tert-butyl {2-[(6-fluoropyridin-2-yl)oxy]ethyl}carbamate

The title compound was prepared starting from 2,6-difluoropyridine.
1H NMR (300 MHz, CDCl$_3$) δ: 7.65 (q, J=8.2 Hz, 1 H), 6.60 (dd, J=1.7, 8.1 Hz, 1 H), 6.47 (dd, J=2.4, 7.8 Hz, 1 H), 4.92 (br. s., 1 H), 4.36-4.28 (m, 2 H), 3.51 (q, J=5.2 Hz, 2 H), 1.44 (s, 9 H). MS: 257 [M+H$^+$]
1-Boc-IIb-C-2 tert-butyl {2-[(6-fluoro-5-methylpyridin-2-yl)oxy]ethyl}carbamate

The title compound was prepared starting from 2,6-difluoro-3-methylpyridine.
MS: 271 [M+H$^+$]
Starting Materials of Formula Boc-IIb-C
Starting amines of formula C—commercially available:
Pyrrolidine (C-1)
Pyrazole (C-2)
N-methylmethanamine (C-3)
N-ethylethanamine (C-4)
N-methyl-1-phenylmethanamine (C-5)
Boc-IIb-C-1 tert-butyl (2-{[6-(pyrrolidin-1-yl)pyridin-2-yl]oxy}ethyl)carbamate

The title compound was prepared starting from the compounds of formula (1-Boc-IIb-C-1) and (C-1)
1H NMR (300 MHz, CD$_3$OD) δ: 7.34 (t, J=8.0 Hz, 1 H), 5.93 (d, J=9.7 Hz, 2 H), 4.26 (t, J=5.6 Hz, 2 H), 3.44-3.35 (m, 6 H), 2.02-1.94 (m, 4 H), 1.42 (s, 9 H), 1.28 (s, 1 H).
MS: 308 [M+H$^+$]
Boc-IIb-C-2 tert-butyl (2-{[6-(1H-pyrazol-1-yl)pyridin-2-yl]oxy}ethyl)carbamate

The title compound was prepared starting from the compounds of formula (1-Boc-IIb-C-1) and (C-2)

1H NMR (300 MHz, CDCl₃) δ: 8.48 (d, J=2.6 Hz, 1 H), 7.74-7.68 (m, 1 H), 7.62 (d, J=2.1 Hz, 1 H), 7.53 (d, J=8.5 Hz, 1 H), 6.63 (dd, J=0.6, 8.1 Hz, 1 H), 6.44 (dd, J=1.5, 2.6 Hz, 1 H), 5.09-4.96 (m,1 H), 4.42 (t, J=5.3 Hz, 2 H), 3.57 (q, J=5.5 Hz, 2 H), 1.45 (s, 9 H). MS: 305 [M+H⁺]

Boc-IIb-C-3 tert-butyl (2-{[6-(dimethylamino)pyridin-2-yl]oxy}ethyl)carbamate

The title compound was prepared starting from the compounds of formula (1-Boc-IIb-C-1) and (C-3)
MS: 282 [M+H⁺]

Boc-IIb-C-4 tert-butyl (2-{[6-(diethylamino)pyridin-2-yl]oxy}ethyl)carbamate

The title compound was prepared starting from the compounds of formula (1-Boc-IIb-C-1) and (C-4)
MS: 310 [M+H⁺]

Boc-IIb-C-5 tert-butyl (2-((6-(benzyl(methyl)amino)-5-methyl-pyridin-2-yl)oxy)ethyl)carbamate The title compound was prepared starting from the compounds of formula (1-Boc-IIb-C-2) and (C-5)
MS: 372 [M+H⁺]

Boc-IIb-C-6 tert-butyl (2-((6-(benzyl(methyl)amino)pyridin-2-yl)oxy)ethyl)carbamate

The title compound was prepared starting from the compounds of formula (1-Boc-IIb-C-1) and (C-5)
MS: 358 [M+H⁺]

Starting Materials of Formula IIb-C

IIb-C-1

2-{[6-(pyrrolidin-1-yl)pyridin-2-yl]oxy}ethanamine hydrochloride

The title compound was prepared starting from the compound of formula (Boc-IIb-C-1).
1H NMR (300 MHz, DMSO-d₆) δ: 8.25 (br. s., 3 H), 7.43 (t, J=8.0 Hz, 1 H), 5.98 (t, J=8.3 Hz, 2 H), 4.38 (t, J=5.4 Hz, 2 H), 3.41-3.29 (m, 4 H), 3.20-3.09 (m, 2 H), 1.97-1.85 (m, 4 H).
MS: 308 [M+H⁺]

IIb-C-2

2-{[6-(1H-pyrazol-1-yl)pyridin-2-yl]oxy}ethanamine hydrochloride

The title compound was prepared starting from the compound of formula (Boc-IIb-C-2).
1H NMR (300 MHz, CD₃OD) δ: 8.60 (d, J=2.1 Hz, 1 H), 7.87 (t, J=8.0 Hz, 1 H), 7.77 (d, J=1.0 Hz, 1 H), 7.52 (d, J=7.7 Hz, 1 H), 6.83 (d, J=8.2 Hz, 1 H), 6.55 (dd, J=1.7, 2.7 Hz, 1 H), 4.67-4.62 (m, 2 H), 3.45-3.38 (m, 2 H) NH protons not detected
MS: 308 [M+H⁺]

IIb-C-3

6-(2-aminoethoxy)-N,N-dimethylpyridin-2-amine hydrochloride

The title compound was prepared starting from the compound of formula (Boc-IIb-C-3).
MS: 308 [M+H⁺]

IIb-C-4

6-(2-aminoethoxy)-N,N-diethylpyridin-2-amine hydrochloride

The title compound was prepared starting from the compound of formula (Boc-IIb-C-4).
MS: 308 [M+H⁺]

IIb-C-5

6-(2-aminoethoxy)-N-benzyl-N,3-dimethylpyridin-2-amine hydrochloride

The title compound was prepared starting from the compound of formula (Boc-IIb-C-5).
MS: 308 [M+H⁺]

IIb-C-6

6-(2-aminoethoxy)-N-benzyl-N-methylpyridin-2-amine hydrochloride

The title compound was prepared starting from the compound of formula (Boc-IIb-C-6).
MS: 308 [M+H⁺]

Starting Materials of Formula IIb-D
Starting Materials of Formula Boc-IIb-D

Boc-IIb-D-1 tert-butyl (2-(2-(methylamino)phenoxy)ethyl)carbamate

The title compound was prepared starting from the 2-(methylamino)phenol and tert-butyl (2-hydroxyethyl)carbamate
¹H NMR (300 MHz, CDCl₃) δ: 6.98-6.84 (m, 1 H), 6.78-6.70 (m, 1 H), 6.63 (ddd, J=1.5, 7.6, 14.4 Hz, 2 H), 4.95 (br. s., 1 H), 4.04 (t, J=5.3 Hz, 2 H), 3.55 (q, J=5.3 Hz, 2 H), 2.86 (s, 3 H), 1.45 (s, 9 H) NH-Boc proton not detected
MS: 267 [M+H⁺]

Starting Materials of Formula IIb-D

IIb-D-1

2-(2-aminoethoxy)-N-methylaniline

The title compound was prepared starting from the compound of formula (Boc-IIb-D-1).
¹H NMR (300 MHz, CDCl₃) δ: 6.95-6.86 (m, 1 H), 6.81-6.72 (m, 1 H), 6.64 (ddd, J=1.8, 7.5, 14.8 Hz, 2 H), 4.02 (t, J=5.3 Hz, 2 H), 3.10 (t, J=5.3 Hz, 2 H), 2.87 (s, 3 H), 1.89 (br. s., 3 H)
MS: 167 [M+H⁺]

Starting Materials of Formula IIb-E
Starting Materials of Formula Br-IIb-E

Br-IIb-E-1 tert-butyl (3-(2-bromoethoxy)phenyl)(methyl)carbamate

The title compound was prepared starting from the tert-butyl (3-hydroxyphenyl)carbamate, 1,2-dibromoethane and iodomethane
¹H NMR (300 MHz, CDCl₃) δ: 7.26-7.18 (m, 1 H), 6.90-6.80 (m, 2 H), 6.72 (dd, J=1.8, 8.2 Hz, 1 H), 4.28 (t, J=6.4 Hz, 2 H), 3.63 (t, J=6.2 Hz, 2 H), 3.24 (s, 3 H), 1.46 (s, 9 H)
MS: 330 [M+H⁺]

Starting Materials of Formula IIb-E
IIb-E-1

3-(2-aminoethoxy)-N-methylaniline

The title compound was prepared starting from the compound of formula (Br-IIb-E-1).

$^1$H NMR (300 MHz, CDCl$_3$) δ: 7.25-7.17 (m, 1 H), 6.85-6.79 (m, 2 H), 6.75-6.69 (m, 1 H), 3.97 (t, J=5.0 Hz, 2 H), 3.24 (s, 3 H), 3.07 (t, J=5.3 Hz, 2 H), 1.48 (br. s., 2 H), 1.45 (s, 9 H)

MS: 266 [M+H$^+$]

Starting Materials of Formula IIb-F
Starting Materials of Formula Pre-IIb-F
Pre-IIb-F-1

6-fluoro-N-methylpyridin-2-amine

The title compound was prepared starting from 2,6-difluoropirydine and methanamine $^1$H NMR (300MH, CDCl$_3$) δ: 7.53-7.42 (m, 1 H), 6.18 (dd, J=2.3, 8.2 Hz, 1 H), 6.13 (dd, J=2.3, 8.2 Hz, 1 H), 4.77 (br. s., 1 H), 2.90 (d, J=4.1 Hz, 3 H)

$^{19}$F NMR (282 MHz, CDCl$_3$) δ: −70,08 (s, 1F)

MS: 127 [M+H$^+$]

Pre-IIb-F-2

6-fluoro-N,N-dimethylpyridin-2-amine

The title compound was prepared starting from 2,6-difluoropirydine and dimetyhylamine $^1$H NMR (300 MHz, CDCl$_3$) δ: 7.54-7.42 (m, 1 H), 6.27 (dd, J=2.3, 8.2 Hz, 1 H), 6.08 (dd, J=2.9, 7.6 Hz, 1 H), 3.06 (s, 6 H)

$^{19}$F NMR (282 MHz, CDCl$_3$) δ: −69.03 (s, 1F)

MS: 141 [M+H$^+$]

Pre-IIb-F-3

N-(6-fluoropyridin-2-yl)acetamide

The title compound was prepared starting from 2,6-difluoropirydine and acetamide $^1$H NMR (300 MHz, CDCl$_3$) δ: 8.06 (d, J=8.2 Hz, 2 H), 7.78 (q, J=7.8 Hz, 1 H), 6.65 (dd, J=2.3, 7.6 Hz, 1 H), 2.20 (s, 3 H)

MS: 155 [M+H$^+$]

Starting Materials of Formula IIb-F
IIb-F-1

6-(2-aminoethoxy)-N-methylpyridin-2-amine

The title compound was prepared starting from the compound of formula Pre-IIb-F1 and ethanolamine $^1$H NMR (300 MHz, CDCl$_3$) δ: 7.40-7.31 (m, 1 H), 6.02 (d, J=8.2 Hz, 1 H), 5.93 (d, J=7.6 Hz, 1 H), 4.41 (br. s., 1 H), 4.22 (t, J=5.3 Hz, 2 H), 3.03 (t, J=5.3 Hz, 2 H), 2.86 (br. s., 3 H), 1.69 (br. s., 2 H)

MS: 168 [M+H$^+$]

IIb-F-2

6-(2-aminoethoxy)-N,N-dimethylpyridin-2-amine

The title compound was prepared starting from the compound of formula Pre-IIb-F2 and ethanolamine $^1$H NMR (300 MHz, CDCl$_3$) δ: 7.36 (t, J=7.9 Hz, 1 H), 6.01 (dd, J=7.9, 9.1 Hz, 2 H), 4.33-4.25 (m, 2 H), 3.09-2.99 (m, 8 H), 1.46 (s, 2 H)

MS: 182 [M+H$^+$]

IIb-F-3

N-(6-(2-aminoethoxy)pyridin-2-yl)acetamide

The title compound was prepared starting from the compound of formula Pre-IIb-F3 and ethanolamine $^1$H NMR (300 MHz, CDCl$_3$) δ: 7.83 (br. s., 1 H), 7.72 (d, J=7.0 Hz, 1 H), 7.57 (t, J=7.9 Hz, 1 H), 6.47 (d, J=8.8 Hz, 1 H), 4.27-4.16 (m, 2 H), 3.09-2.99 (m, 2 H), 2.19 (s, 3 H), 1.52 (s, 2 H)

MS: 196 [M+H$^+$]

The preparation of compound (I) from compounds IIa and IIb is depicted in the FIG. 2 F—Scheme 6.

The cyanohydrin of formula IIa (1.0 eq, 0.478 mmol) was dissolved in methanol (5 mL) at room temperature, 1,4-diaza-bicyclo[2.2.2]octane (12.5 eq, 5.97 mmol) was added in one portion, followed by appropriate amine of formula IIb (1.6 eq , 0.764 mmol), 4A molecular sieves (1.04 g), sodium cyanoborohydride (7.8eq, 3.73 mmol), and iron sulfate (FeSO4.7H2O) (1.2 eq, 0.526 mmol). Mixture stirred at room temperature until the cyanohydrin was consumed. After stirring for 72 hours, mixture filtered to remove insoluble material, concentrated in vacuo to remove methanol and subsequently quenched with brine. The Aqueous was extracted with ethyl acetate three times, organics combined and dried over magnesium sulfate, filtered and concentrated to crude product. Purification via flash chromatography (5% methanol/ethyl acetate) yielded pure product as a colorless oil. The yield of compounds (I) was in the range of 28-98%, and HPLC purity in the range of 95-100%.

According to the above general procedure, various compounds of formula (I) according to the invention were prepared and are depicted in the example section.

Compound (I) can also be prepared starting from their Boc-protected intermediates (i.e. compound 75) according to FIG. 2 K—Scheme 11 depicting the general synthesis.

The appropriate product of formula IIb-E (1 eq., 0.15 mmol) was poured with 1M hydrochloric acid in ethyl acetate (5 mL), and stirred for 24 h. Then, the mixture was filtered giving pure hydrochloride as a white-gray solid. (yield 71%).

Compound (I) can also be prepared starting from their benzyl intermediates (i.e. compound 49 and 50) according to FIG. 2 G—Scheme 7 depicting the general synthesis.

The appropriate compound of formula (Benzyl-I) (0.100 g, 0.189 mmol) was dissolved in ethanol (2 mL) and added to a round bottom flask containing 10% Pd/C (0.100 g) under nitrogen gas. Cyclohexene (1 mL) was then added and mixture warmed to 90° C. with stirring. After 72 hours, mixture was cooled to room temperature, filtered over celite, and filtrate concentrated in vacuo to yield crude product as an orange oil. Crude was purified via flash chromatography (ethyl acetate/hexanes/trimethylamine 3:6:1) to yield pure product as a light tan solid (22% yield).

The invention also extends to additive salts from compounds of aforementioned formula I, with pharmaceutically acceptable mineral or organic acids.

More particularly, the present invention target some of the 1-48 numbered compounds of formula (I) selected in the group consisting of:

Compound 1

(3-chloro-4-fluorophenyl)(4-fluoro-4-(((2-phenoxyethyl)amino)methyl)piperidin-1-yl)methanone The title compound was prepared starting from the compound (IIa-2) and amine (IIb-1).

¹H NMR (300 MHz, CDCl₃) δ: 7.48 (dd, J=2.1, 7.2 Hz, 1 H), 7.33-7.26 (m, 3 H), 7.22-7.13 (m, 1 H), 6.99-6.86 (m, 3 H), 4.51 (br. s., 1 H), 4.07 (t, J=5.1 Hz, 2 H), 3.71-3.53 (m, 1 H), 3.22 (br. s., 2 H), 3.03 (t, J=5.1 Hz, 2 H), 2.92-2.77 (m, 2 H), 2.01 (br. s., 2 H), 1.67 (br. s., 3 H)
¹⁹F NMR (282 MHz, CDCl₃) δ: −112,63 (s, 1F), −166,48 (s, 1F)
¹³C NMR (75 MHz, CDCl₃) δ: 168.1, 158.7, 157.1, 132.9, 129.7, 129.5, 127.1, 121.6, 121.4, 120.9, 116.9, 116.6, 114.5, 95.5, 93.2, 67.2, 57.5, 57.2, 49.3
MS: 409 [M+H⁺]
Compound 2

N-(3-(2-(((1-(3-chloro-4-fluorobenzoyl)-4-fluoropiperidin-4-yl)methyl)amino)ethoxy)phenyl)acetamide The title compound was prepared starting from the compound (IIa-2) and amine (IIb-2).
¹H NMR (300 MHz, CDCl₃) δ: 7.89 (br. s., 1 H), 7.46 (dd, J=2.1, 6.9 Hz, 1 H), 7.35-7.31 (m, 1 H), 7.30-7.24 (m, 1 H), 7.21-7.11 (m, 2 H), 6.92 (d, J=8.0 Hz, 1 H), 6.61 (dd, J=2.1, 8.2 Hz, 1 H), 5.86-5.58 (m, 5 H), 4.48 (br. s., 1 H), 4.03 (t, J=5.1 Hz, 2 H), 3.58 (br. s., 1 H), 3.42 -3.10 (m, 2 H), 3.00 (t, J=5.0 Hz, 2 H), 2.89-2.76 (m, 2 H), 2.13 (s, 3 H), 2.03 (br. s., 2 H), 1.63 (br. s., 3 H)
¹³C NMR (75 MHz, CDCl₃) δ: 173.0, 168.1, 160.4, 159.2, 157.1, 139.4, 132.8, 129.6, 127.1, 121.5, 116.8, 112.2, 110.2, 106.4, 95.4, 93.2, 67.3, 57.3, 57.0, 49.2, 22.6
MS: 466 [M+H⁺]
Compound 3

N-(3-(2-(((1-(3,4-dichlorobenzoyl)-4-fluoropiperidin-4-yl)methyl)amino)ethoxy)phenyl)acetamide The title compound was prepared starting from the compound (IIa-1) and amine (IIb-2)
¹H NMR (300 MHz, CDCl₃) δ: 7.56-7.45 (m, 2 H), 7.34 (br. s., 1 H), 7.23 (dd, J=1.9, 8.1 Hz, 1 H), 7.10-6.97 (m, 1 H), 6.89 (d, J=7.2 Hz, 1 H), 6.65 (d, J=7.4 Hz, 1 H), 6.26-6.11 (m, 1 H), 4.52 (br. s., 1 H), 4.05 (t, J=5.0 Hz, 2 H), 3.57 (br. s., 1 H), 3.47-3.09 (m, 2 H), 3.06-2.97 (m, 2 H), 2.90-2.77 (bd, 2 H), 2.16 (s, 3 H), 1.84-1.45 (m, 5 H)
MS: 483 [M+H⁺]
Compound 4

(3-chloro-4-fluorophenyl)(4-(((2-(3-chlorophenoxy)ethyl)amino)methyl)-4-fluoropiperidin-1-yl)methanone The title compound was prepared starting from the compound (IIa-2) and amine (IIb-3)
¹H NMR (300 MHz, CDCl₃) δ: 7.48 (dd, J=2.1, 6.9 Hz, 1 H), 7.33-7.26 (m, 1 H), 7.18 (dt, J=5.1, 8.3 Hz, 2 H), 6.96-6.91 (m, 1 H), 6.90 (t, J=2.1 Hz, 1 H), 6.78 (ddd, J=0.8, 2.4, 8.3 Hz, 1 H), 4.52 (br. s., 1 H), 4.04 (t, J=5.0 Hz, 2 H), 3.60 (br. s., 1 H), 3.37 (br. s., 2 H), 3.02 (t, J=5.1 Hz, 2 H), 2.90-2.77 (m, 2 H), 2.02 (br. s., 2 H), 1.63 (s, 3 H)
¹³C NMR (75 MHz, CDCl₃) δ: 168.1, 160.5, 159.5, 157.1, 134.9, 132.9, 130.2, 129.7, 127.0, 121.1, 116.8, 114.9, 113.0, 95.5, 93.2, 67.6, 57.5, 57.2, 49.1
MS: 443 [M+H⁺]
Compound 5

(3-chloro-4-fluorophenyl)(4-fluoro-4-(((2-(3-fluorophenoxy)ethyl)amino)methyl)piperidin-1-yl)methanone The title compound was prepared starting from the compound (IIa-2) and amine (IIb-4)

¹H NMR (300 MHz, CDCl₃) δ: 7.48 (dd, J=2.1, 6.9 Hz, 1 H), 7.33-7.26 (m, 1 H), 7.24-7.13 (m, 2 H), 6.67 (tdd, J=1.0, 2.0, 9.5 Hz, 2 H), 6.64-6.58 (m, 1 H), 4.51 (br. s., 1 H), 4.04 (t, J=5.0 Hz, 2 H), 3.60 (br. s., 1 H), 3.46-3.10 (m, 2 H), 3.03 (t, J=5.1 Hz, 2 H), 2.90-2.77 (m, 2 H), 2.01 (br. s., 2 H), 1.63 (br. s., 3 H)
¹³C NMR (75 MHz, CDCl₃) δ: 168.1, 165.2, 162.0, 160.2, 157.1, 132.9, 130.0, 127.1, 121.5, 116.8, 110.2, 107.7, 102.2, 95.5, 93.2, 67.7, 57.5, 57.2, 49.1
MS: 427 [M+H⁺]
Compound 6

(3-chloro-4-fluorophenyl)(4-fluoro-4-(((2-(2-methoxyphenoxy)ethyl)amino)methyl)piperidin-1-yl)methanone The title compound was prepared starting from the compound (IIa-2) and amine (IIb-5)
¹H NMR (300 MHz, CDCl₃) δ: 7.48 (dd, J=2.1, 6.9 Hz, 1 H), 7.32-7.26 (m, 1 H), 7.20-7.13 (m, 1 H), 6.98-6.85 (m, 4 H), 4.50 (br. s., 1 H), 4.12 (t, J=5.3 Hz, 2 H), 3.84 (s, 3 H), 3.60 (br. s., 1 H), 3.45-3.13 (m, 2 H), 3.04 (t, J=5.3 Hz, 2 H), 2.91-2.79 (m, 2 H), 2.10-1.92 (m, 2 H), 1.70 (br. s., 3 H)
¹⁹F NMR (282 MHz, CDCl₃) δ: −112,66 (s, 1F), −166,26 (s, 1F)
¹³C NMR (75 MHz, CDCl₃) δ: 168.0, 160.4, 157.1, 149.8, 148.2, 133.0, 129.7, 127.1, 121.6, 120.9, 116.8, 114.2, 111.9, 95.5, 93.2, 69.0, 57.4, 57.1, 55.8, 49.3
MS: 439 [M+H⁺]
Compound 7

(3,4-dichlorophenyl)(4-fluoro-4-(((2-(2-methoxyphenoxy)ethyl)amino)methyl)piperidin-1-yl)methanone The title compound was prepared starting from the compound (IIa-1) and amine (IIb-5)
¹H NMR (300 MHz, CDCl₃) δ: 7.53-7.45 (m, 2 H), 7.23 (dd, J=1.8, 8.2 Hz, 1 H), 6.99-6.84 (m, 4 H), 4.51 (br. s., 1 H), 4.12 (t, J=5.3 Hz, 2 H), 3.84 (s, 3 H), 3.57 (br. s., 1 H), 3.46-3.10 (m, 2 H), 3.04 (t, J=5.1 Hz, 2 H), 2.91-2.78 (m, 2 H), 2.00 (br. s., 2 H), 1.77 (br. s., 3 H)
¹³C NMR (75 MHz, CDCl₃) δ: 167.9, 149.7, 148.2, 135.7, 134.1, 133.0, 130.6, 129.1, 126.2, 121.6, 120.9, 114.2, 111.9, 95.5, 93.2, 69.0, 57.3, 55.8, 49.3, 29.7
MS: 455 [M+H⁺]
Compound 8

(3-chloro-4-fluorophenyl)(4-fluoro-4-(((2-(3-methoxyphenoxy)ethyl)amino)methyl)piperidin-1-yl)methanone The title compound was prepared starting from the compound (IIa-2) and amine (IIb-6)
¹H NMR (300 MHz, CDCl₃) δ: 7.48 (dd, J=2.1, 6.9 Hz, 1 H), 7.33-7.26 (m, 1 H), 7.21-7.13 (m, 2 H), 6.54-6.48 (m, 2 H), 6.47-6.45 (m, 1 H), 4.52 (br. s., 1 H), 4.05 (t, J=5.1 Hz, 2 H), 3.78 (s, 3 H), 3.59 (br. s., 1 H), 3.45-3.11 (m, 2 H), 3.02 (t, J=5.0 Hz, 2 H), 2.91-2.76 (m, 2 H), 2.01 (br. s., 2 H), 1.71 (br. s., 3 H)
¹³C NMR (75 MHz, CDCl₃) δ: 168.1, 160.8, 160.4, 160.0, 157.1, 132.9, 129.8, 127.1, 121.5, 116.8, 106.6, 106.4, 101.0, 95.5, 93.2, 67.3, 57.4, 57.1, 55.3, 49.3
MS: 439 [M+H⁺]

Compound 9

(3,4-dichlorophenyl)(4-fluoro-4-(((2-(3-methoxyphenoxy)ethyl)amino)methyl)piperidin-1-yl)methanone The title compound was prepared starting from the compound (IIa-1) and amine (IIb-6)

¹H NMR (300 MHz, CDCl₃) δ: 7.53-7.47 (m, 2 H), 7.23 (dd, J=1.8, 8.2 Hz, 1 H), 7.18 (t, J=8.1 Hz, 1 H), 6.56-6.43 (m, 3 H), 4.51 (br. s., 1 H), 4.05 (t, J=5.1 Hz, 2 H), 3.79 (s, 3 H), 3.60 (br. s., 1 H), 3.38 (br. s., 2 H), 3.02 (t, J=5.0 Hz, 2 H), 2.90-2.78 (m, 2 H), 2.01 (br. s., 2 H), 1.59 (br. s., 3 H)

MS: 455 [M+H⁺]

Compound 10

(3-chloro-4-fluorophenyl)(4-fluoro-4-(((2-(4-methoxyphenoxy)ethyl)amino)methyl)piperidin-1-yl)methanone The title compound was prepared starting from the compound (IIa-2) and amine (IIb-7)

¹H NMR (300 MHz, CDCl₃) δ: 7.48 (dd, J=2.1, 6.9 Hz, 1 H), 7.33-7.26 (m, 1 H), 7.22-7.14 (m, 1 H), 6.83 (s, 4 H), 4.50 (br. s., 1 H), 4.01 (t, J=5.1 Hz, 2 H), 3.76 (s, 3 H), 3.60 (br. s., 1 H), 3.44-3.13 (m, 2 H), 3.00 (t, J=5.1 Hz, 2 H), 2.90-2.78 (m, 2 H), 2.02 (s, 2 H), 1.64 (br. s., 3 H)

¹³C NMR (75 MHz, CDCl₃) δ: 168.1, 160.4, 157.1, 153.4, 132.9, 129.7, 127.1, 121.5, 116.8, 115.5, 114.7, 95.5, 93.2, 68.0, 57.5, 57.2, 55.7, 49.4

MS: 439 [M+H⁺]

Compound 11

(3,4-dichlorophenyl)(4-fluoro-4-(((2-(4-methoxyphenoxy)ethyl)amino)methyl)piperidin-1-yl)methanone The title compound was prepared starting from the compound (IIa-1) and amine (IIb-7)

¹H NMR (300 MHz, CDCl₃) δ: 7.54-7.44 (m, 2 H), 7.23 (dd, J=2.1, 8.2 Hz, 1 H), 6.83 (s, 4 H), 4.52 (br. s., 1 H), 4.01 (t, J=5.1 Hz, 2 H), 3.76 (s, 3 H), 3.57 (br. s., 1 H), 3.45-3.10 (m, 2 H), 3.00 (t, J=5.0 Hz, 2 H), 2.88-2.77 (m, 2 H), 2.02 (m, 2 H), 1.61 (br. s., 3 H)

¹⁹F NMR (282 MHz, CDCl₃) δ: −166,50 (s, 1F)

¹³C NMR (75 MHz, CDCl₃) δ: 167.9, 154.0, 152.9, 135.7, 134.1, 133.0, 130.6, 129.1, 126.2, 115.5, 114.6, 95.5, 93.2, 68.0, 57.5, 57.2, 55.7, 49.4

MS: 455 [M+H⁺]

Compound 12

(3-chloro-4-fluorophenyl)(4-fluoro-4-(((2-(2-(methylthio)phenoxy)ethyl)amino)methyl)piperidin-1-yl)methanone The title compound was prepared starting from the compound (IIa-2) and amine (IIb-8)

¹H NMR (300 MHz, CDCl₃) δ: 7.48 (dd, J=2.1, 6.9 Hz, 1 H), 7.32-7.26 (m, 1 H), 7.20-7.07 (m, 3 H), 7.01-6.94 (m, 1 H), 6.83 (d, J=8.2 Hz, 1 H), 4.51 (br. s., 1 H), 4.13 (t, J=5.0 Hz, 2 H), 3.58 (br. s., 1 H), 3.45-3.13 (m, 2 H), 3.07 (t, J=5.0 Hz, 2 H), 2.94-2.82 (m, 2 H), 2.41 (s, 3 H), 2.10-1.92 (m, 2 H), 1.75 (br. s., 3 H)

¹³C NMR (75 MHz, CDCl₃) δ: 168.0, 160.4, 157.1, 155.2, 133.0, 129.7, 127.6, 127.1, 125.6, 121.6, 121.4, 116.8, 111.6, 95.5, 93.2, 68.5, 57.4, 57.1, 49.1, 14.4

MS: 455 [M+H⁺]

Compound 13

((3,4-dichlorophenyl)(4-fluoro-4-(((2-(2-(methylthio)phenoxy)ethyl)amino)methyl)piperidin-1-yl) methanone The title compound was prepared starting from the compound (IIa-1) and amine (IIb-8)

¹H-NMR (300 MHz, CDCl₃) δ: 7.51-7.48 (m., 2H), 7.26-7.24 (m., 1H), 7.13-7.10 (m., 2H), 7.00-6.96 (m., 1H), 6.85-6.83 (m., 1H), 4.52-4.50 (m., 1H), 4.16-4.13 (t., J=5.1 Hz, 2H), 3.58-3.10 (m., 3H), 3.09-3.07 (t., J=5.3 Hz, 2H), 2.92-2.87 (d., J=19.9 Hz, 2H), 2.42 (s., 3H), 2.01 (br s., 2H) 1,69-1.24 (m., 3H).

MS: 471 [M+H⁺]

Compound 14

(3-chloro-4-fluorophenyl)(4-(((2-((2,3-dihydrobenzo[b][1,4]dioxin-5-yl)oxy)ethyl)amino)methyl)-4-fluoropiperidin-1-yl)methanone The title compound was prepared starting from the compound (IIa-2) and amine (IIb-9)

¹H NMR (300 MHz, CDCl₃) δ: 7.48 (dd, J=2.1, 6.9 Hz, 1 H), 7.32-7.26 (m, 1 H), 7.21-7.14 (m, 1 H), 6.78-6.71 (m, 1 H), 6.53 (ddd, J=1.3, 8.2, 10.8 Hz, 2 H), 4.50 (br. s., 1 H), 4.32-4.27 (m, 2 H), 4.27-4.23 (m, 2 H), 4.16-4.07 (m, 2 H), 3.60 (br. s., 1 H), 3.34 (br. s., 2 H), 3.05 (t, J =5.3 Hz, 2 H), 2.91-2.78 (m, 2 H), 2.02 (s, 2 H), 1.63 (br. s., 3 H)

MS: 467 [M+H⁺]

Compound 15

(3,4-dichlorophenyl)(4-(((2-((2,3-dihydrobenzo[b][1,4]dioxin-5-yl)oxy)ethyl)amino)methyl)-4-fluoropiperidin-1-yl)methanone The title compound was prepared starting from the compound (IIa-1) and amine (IIb-9)

¹H NMR (300 MHz, CDCl₃) δ: 7.53-7.46 (m, 2 H), 7.23 (dd, J=1.8, 8.2 Hz, 1 H), 6.78-6.71 (m, 1 H), 6.52 (ddd, J=1.4, 8.3, 10.8 Hz, 2 H), 4.51 (br. s., 1 H), 4.31-4.27 (m, 2 H), 4.27-4.23 (m, 2 H), 4.11 (t, J=5.4 Hz, 2 H), 3.56 (br. s., 1 H), 3.45-3.11 (m, 2 H), 3.04 (t, J=5.1 Hz, 2 H), 2.90-2.79 (m, 2 H), 2.08-1.92 (m, 2 H), 1.67 (br. s., 3 H)

¹⁹F NMR (282 MHz, CDCl₃) δ: −166,28 (s, 1F)

¹³C NMR (75 MHz, CDCl₃) δ: 167.9, 148.2, 144.4, 135.7, 134.1, 133.9, 133.0, 130.6, 129.1, 126.2, 120.2, 110.5, 106.3, 95.5, 93.2, 69.0, 64.4, 64.2, 57.3, 49.2

MS: 483 [M+H⁺]

Compound 16

(3-chloro-4-fluorophenyl)(4-fluoro-4-(((2-(quinolin-8-yloxy)ethyl)amino)methyl)piperidin-1-yl)methanone The title compound was prepared starting from the compound (IIa-2) and amine (IIb-10)

¹H NMR (300 MHz, CDCl₃) δ: 8.92 (dd, J=1.8, 4.1 Hz, 1 H), 8.15 (dd, J=1.7, 8.3 Hz, 1 H), 7.50 -7.38 (m, 4 H), 7.28 (dd, J=2.1, 4.6 Hz, 1 H), 7.19-7.12 (m, 1 H), 7.09 (dd, J=1.7, 7.3 Hz, 1 H), 4.50 (br. s., 1 H), 4.34 (t, J=5.3 Hz, 2 H), 3.58 (br. s., 1 H), 3.39-3.13 (m, 4 H), 2.98-2.86 (m, 2 H), 2.06-1.97 (m, 2 H), 1.66 (br. s., 3 H)

¹³C NMR (75 MHz, CDCl₃) δ: 168.0, 160.4, 157.1, 154.5, 149.2, 140.2, 136.1, 132.9, 129.7, 129.5, 127.1, 126.7, 121.7, 120.1, 116.7, 109.4, 95.5, 93.2, 68.7, 57.4, 57.1, 49.1

MS: 460 [M+H⁺]

Compound 17

(3,4-dichlorophenyl)(4-fluoro-4-(((2-(quinolin-8-yloxy)ethyl)amino)methyl)piperidin-1-yl)methanone The title compound was prepared starting from the compound (IIa-1) and amine (IIb-10)
$^1$H-NMR (300 MHz, CDCl$_3$) δ: 7.52-7.41 (m, 5H), 7.27 (m, 2H), 7.26-7.19 (m, 1H), 7.12-7.09 (m, 1H), 4.52 (m, 1H), 4.72-4.43 (t, J=5.1 Hz, 2H), 3.55 (m, 1H), 3.37 (m, 1H), 3.26-3.23 (t, J=5.2 Hz, 2H), 3.17 (m, 1H), 2.95-2.90 (d, J=19.9 Hz, 2H), 2.01 (br s, 2H) 1,69-1.24 (m, 3H).
MS: 477 [M+H$^+$]

Compound 18

(3-chloro-4-fluorophenyl)(4-fluoro-4-(((2-(pyridin-2-yloxy)ethyl)amino)methyl)piperidin-1-yl)methanone The title compound was prepared starting from the compound (IIa-2) and amine (IIb-11)
$^1$H NMR (300 MHz, CDCl$_3$) δ: 8.16-8.08 (m, 1 H), 7.61-7.52 (m, 1 H), 7.47 (dd, J=1.8, 7.0 Hz, 1 H), 7.33-7.26 (m, 1 H), 7.20-7.12 (m, 1 H), 6.90-6.82 (m, 1 H), 6.77-6.68 (m, 1 H), 4.50 (br. s., 1 H), 4.42-4.33 (m, 2 H), 3.57 (br. s., 1 H), 3.46-3.06 (m, 2 H), 3.02 (t, J=5.3 Hz, 2 H), 2.91-2.73 (m, 2 H), 2.01 (br. s., 2 H), 1.87-1.52 (m, 3 H)
$^{19}$F NMR (282 MHz, CDCl$_3$) δ: −112,63 (s, 1F), −166,52 (s, 1F)
$^{13}$C NMR (75 MHz, CDCl$_3$) δ: 168.0, 163.6, 160.4, 157.1, 146.8, 138.6, 132.9, 129.7, 127.1, 121.5, 116.8, 111.0, 95.5, 93.2, 65.1, 57.4, 57.1, 49.2
MS: 410 [M+H$^+$]

Compound 19

(3-chloro-4-fluorophenyl)(4-fluoro-4-(((2-(pyridin-3-yloxy)ethyl)amino)methyl)piperidin-1-yl)methanone The title compound was prepared starting from the compound (IIa-2) and amine (IIb-12)
$^1$H NMR (300 MHz, CDCl$_3$) δ: 8.32 (td, J=1.0, 1.7 Hz, 1 H), 8.25-8.21 (m, 1 H), 7.48 (dd, J=2.1, 6.9 Hz, 1 H), 7.33-7.26 (m, 1 H), 7.23-7.13 (m, 3 H), 4.52 (br. s., 1 H), 4.11 (t, J=5.1 Hz, 2 H), 3.61 (br. s., 1 H), 3.18 (d, J=5.1 Hz, 2 H), 3.05 (t, J=5.1 Hz, 2 H), 2.90-2.79 (m, 2 H), 2.08-1.95 (m, 2 H), 1.79 (br. s., 3 H)
$^{13}$C NMR (75 MHz, CDCl$_3$) δ: 168.1, 160.5, 157.1, 154.9, 142.3, 137.9, 132.9, 129.7, 127.1, 123.8, 121.1, 116.8, 95.5, 93.3, 93.2, 67.8, 57.5, 57.2, 49.1
MS: 410 [M+H$^+$]

Compound 20

(3-chloro-4-fluorophenyl)(4-fluoro-4-(((2-(pyridin-4-yloxy)ethyl)amino)methyl)piperidin-1-yl)methanone The title compound was prepared starting from the compound (IIa-1) and amine (IIb-13)
MS: 410 [M+H$^+$]

Compound 21

(3-chloro-4-fluorophenyl)(4-fluoro-4-(((2-((5-methylpyridin-2-yl)oxy)ethyl)amino)methyl)piperidin-1-yl)methanone The title compound was prepared starting from the compound (IIa-2) and amine (IIb-14)
$^1$H-NMR (300 MHz, CDCl$_3$) δ: 7.94-7.9 3 (m., 1H), 7.49-7.47 (m., 1H), 7.41-7.28 (m., 2H), 7.20-7.16 (m., 1H), 6.67-6.65 (d., 1H), 4.51 (m., 1H), 4.38-4.35 (t., J=5.1 Hz, 2H), 3.64-3.18 (m., 3H), 3.04-3.01 (t., J=5.3 Hz, 2H), 2.87-2.82 (d., J=19.9 Hz, 2H), 2.24 (s., 3H), 2.00 (br s., 2H) 1,83-1.51 (m., 3H).
MS: 424 [M+H$^+$]

Compound 22

(3-chloro-4-fluorophenyl)(4-(((2-((5-chloropyridin-2-yl)oxy)ethyl)amino)methyl)-4-fluoropiperidin-1-yl)methanone The title compound was prepared starting from the compound (IIa-2) and amine (IIb-15)
$^1$H NMR (300 MHz, CDCl$_3$) δ: 8.08 (d, J=2.1 Hz, 1 H), 7.56-7.45 (m, 2 H), 7.33-7.26 (m, 1 H), 7.22-7.13 (m, 1 H), 6.70 (dd, J=0.6, 8.8 Hz, 1 H), 4.51 (br. s., 1 H), 4.41-4.31 (m, 2 H), 3.64 (d, J=19.5 Hz, 1 H), 3.43-3.13 (m, 2 H), 3.02 (t, J=5.3 Hz, 1 H), 2.89-2.77 (m, 2 H), 2.00 (br. s., 2 H), 1.62 (br. s., 3 H)
$^{13}$C NMR (75 MHz, CDCl$_3$) δ: 168.1, 162.1, 160.5, 157.1, 145.1, 138.6, 132.9, 129.7, 127.1, 124.2, 116.8, 112.0, 95.5, 93.2, 65.7, 57.4, 57.1, 49.1
MS: 444 [M+H$^+$]

Compound 23

(3-chloro-4-fluorophenyl)(4-fluoro-4-(((2-((3-methoxypyridin-2-yl)oxy)ethyl)amino)methyl)piperidin-1-yl)methanone The title compound was prepared starting from the compound (IIa-2) and amine (IIb-16)
$^1$H NMR (300 MHz, CDCl$_3$) δ: 7.70 (dd, J=1.4, 5.0 Hz, 1 H), 7.47 (dd, J=2.1, 6.9 Hz, 1 H), 7.32-7.26 (m, 1 H), 7.22-7.13 (m, 1 H), 7.05 (dd, J=1.4, 7.8 Hz, 1 H), 6.84 (dd, J=5.1, 7.7 Hz, 1 H), 4.48 (t, J=5.5 Hz, 3 H), 3.85 (s, 3 H), 3.60 (br. s., 1 H), 3.44-3.15 (m, 2 H), 3.08 (t, J=5.4 Hz, 2 H), 2.92-2.77 (m, 2 H), 1.98 (br. s., 2 H), 1.66 (br. s., 3 H)
MS: 440 [M+H$^+$]

Compound 24

(3-chloro-4-fluorophenyl)(4-fluoro-4-(((2-((4-(trifluoromethyl)pyridin-2-yl)oxy)ethyl)amino)methyl)piperidin-1-yl)methanone The title compound was prepared starting from the compound (IIa-2) and amine (IIb-17)
$^1$H NMR (300 MHz, CDCl$_3$) δ: 8.28 (d, J=5.4 Hz, 1 H), 7.47 (dd, J=2.1, 6.9 Hz, 1 H), 7.32-7.26 (m, 1 H), 7.21-7.13 (m, 1 H), 7.07 (dd, J=0.9, 5.3 Hz, 1 H), 6.99-6.94 (m, 1 H), 4.50 (br. s., 1 H), 4.46-4.40 (m, 2 H), 3.60 (br. s., 1 H), 3.34 (br. s., 2 H), 3.03 (t, J=5.3 Hz, 2 H), 2.90-2.76 (m, 2 H), 2.00 (br. s., 2 H), 1.69 (br. s., 3 H)
$^{13}$C NMR (75 MHz, CDCl$_3$) δ: 168.1, 164.0, 160.4, 157.1, 148.3, 140.7, 132.9, 129.7, 127.1, 121.5, 116.8, 112.4, 107.7, 95.5, 93.2, 66.0, 57.4, 57.1, 49.0
MS: 478 [M+H$^+$]

Compound 25

(3-chloro-4-fluorophenyl)(4-fluoro-4-(((2-((6-fluoropyridin-2-yl)oxy)ethyl)amino)methyl)piperidin-1-yl)methanone The title compound was prepared starting from the compound (IIa-2) and amine (IIb-B-1)

¹H NMR (300 MHz, CDCl₃) δ: 7.64 (q, J=8.0 Hz, 1 H), 7.47 (dd, J=2.1, 6.9 Hz, 1 H), 7.33-7.27 (m, 1 H), 7.22-7.11 (m, 1 H), 6.59 (dd, J=1.7, 8.1 Hz, 1 H), 6.46 (dd, J=2.4, 7.8 Hz, 1 H), 4.50 (br. s., 1 H), 4.40-4.31 (m, 2 H), 3.58 (br. s., 1 H), 3.44-3.10 (m, 2 H), 3.01 (t, J=5.4 Hz, 2 H), 2.89-2.75 (m, 2 H), 2.00 (br. s., 2 H), 1.64 (br. s., 3 H)
¹³C NMR (75 MHz, CDCl₃) δ: 168.1, 163.7, 162.8, 160.4, 157.1, 142.6, 132.9, 129.7, 127.1, 121.5, 116.8, 107.1, 100.2, 95.5, 93.2, 65.9, 57.3, 57.0, 48.9
MS: 428 [M+H⁺]
Compound 26

(3-chloro-4-fluorophenyl)(4-fluoro-4-(((2-((6-(methylamino)pyridin-2-yl)oxy)ethyl)amino)methyl)piperidin-1-yl)methanone The title compound was prepared starting from the compound (IIa-2) and amine (IIb-F-1) and also was prepared from compound 49 (pre-compound 26)
¹H NMR (300 MHz, CDCl₃) δ: 7.47 (dd, J=2.3, 7.0 Hz, 1 H), 7.35 (t, J=1.0 Hz, 1 H), 7.31-7.26 (m, 1 H), 7.21-7.11 (m, 1 H), 6.00 (d, J=8.2 Hz, 1 H), 5.93 (d, J=8.2 Hz, 1 H), 4.50 (br. s., 1 H), 4.39 (d, J=4.7 Hz, 1 H), 4.33-4.25 (m, 2 H), 3.57 (br. s., 1 H), 3.45-3.03 (m, 2 H), 2.99 (t, J=5.3 Hz, 2 H), 2.89-2.74 (m, 5 H), 1.99 (br. s., 2 H), 1.66 (br. s., 3 H)
¹⁹F NMR (282 MHz, CDCl₃) δ: −112,71 (s, 1F), −166,27 (s, 1F)
¹³C NMR (75 MHz, CDCl₃) δ: 168.0, 163.1, 160.4, 158.6, 157.1, 140.1, 132.9, 129.7, 127.1, 121.5, 116.8, 97.3, 95.5, 93.2, 64.8, 57.4, 57.1, 49.4, 29.1
MS: 439 [M+H⁺]
Compound 27

(3-chloro-4-fluorophenyl)(4-(((2-((6-(dimethylamino)pyridin-2-yl)oxy)ethyl)amino)methyl)-4-fluoropiperidin-1-yl)methanone The title compound was prepared starting from the compound (IIa-2) and amine (IIb-F-2)
¹H NMR (300 MHz, CDCl₃) δ: 7.47 (dd, J=1.8, 7.0 Hz, 1 H), 7.40-7.32 (m, 1 H), 7.31-7.26 (m, 1 H), 7.20-7.11 (m, 1 H), 5.99 (dd, J=7.6, 15.2 Hz, 2 H), 4.49 (br. s., 1 H), 4.40-4.32 (m, 2 H), 3.58 (br. s., 1 H), 3.46-3.06 (m, 2 H), 3.05-2.94 (m, 8 H), 2.83 (d, J=19.9 Hz, 2 H), 2.00 (br. s., 2 H), 1.72 (br. s., 3 H)
¹⁹F NMR (282 MHz, CDCl₃) δ: −112,70 (s, 1F), −166,30 (s, 1F)
¹³C NMR (75 MHz, CDCl₃) δ: 168.0, 162.5, 160.4, 158.3, 157.1, 139.8, 132.9, 129.7, 127.1, 121.5, 116.8, 97.2, 96.1, 95.5, 93.2, 64.6, 57.4, 57.1, 49.4, 37.9
MS: 453 [M+H⁺]
Compound 28

(3-chloro-4-fluorophenyl)(4-(((2-((6-(diethylamino)pyridin-2-yl)oxy)ethyl)amino)methyl)-4-fluoropiperidin-1-yl)methanone The title compound was prepared starting from the compound (IIa-2) and amine (IIb-C-4)
MS: 481 [M+H⁺]
Compound 29

(3-chloro-4-fluorophenyl)(4-fluoro-4-(((2-((6-(pyrrolidin-1-yl)pyridin-2-yl)oxy)ethyl)amino)methyl)piperidin-1-yl)methanone The title compound was prepared starting from the compound (IIa-2) and amine (IIb-C-1)
¹H NMR (300 MHz, CDCl₃) δ: 7.48 (dd, J=1.9, 7.1 Hz, 1 H), 7.38-7.31 (m, 1 H), 7.31-7.26 (m, 1 H), 7.21-7.14 (m, 1 H), 5.94 (d, J=7.7 Hz, 1 H), 5.88 (d, J=8.2 Hz, 1 H), 4.51 (br. s., 1 H), 4.39-4.33 (m, 2 H), 3.64 (d, J=19.5 Hz, 1 H), 3.41 (t, J=6.8 Hz, 4 H), 3.17 (br. s., 2 H), 3.01 (t, J=5.3 Hz, 2 H), 2.88-2.77 (m, 2 H), 2.08-1.92 (m, 6 H), 1.63 (br. s., 3 H)
¹³C NMR (75 MHz, CDCl₃) δ: 168.0, 162.9, 160.4, 156.7, 139.6, 133.0, 129.7, 127.1, 121.5, 116.7, 95.4, 93.2, 64.6, 57.4, 57.1, 49.5, 46.6
MS: 479 [M+H⁺]
Compound 30

(4-(((2-((6-(1H-pyrazol-1-yl)pyridin-2-yl)oxy)ethyl)amino)methyl)-4-fluoropiperidin-1-yl)(3-chloro-4-fluorophenyl)methanone The title compound was prepared starting from the compound (IIa-2) and amine (IIb-C-2)
¹H NMR (300 MHz, CDCl₃) δ: 8.45 (d, J=2.6 Hz, 1 H), 7.73-7.65 (m, 2 H), 7.51 (d, J=7.7 Hz, 1 H), 7.47 (dd, J=2.1, 6.9 Hz, 1 H), 7.32-7.26 (m, 1 H), 7.21-7.12 (m, 1 H), 6.62 (d, J=7.4 Hz, 1 H), 6.43 (dd, J=1.8, 2.6 Hz, 1 H), 4.61-4.37 (m, 3 H), 3.59 (br. s., 1 H), 3.44-3.15 (m, 2 H), 3.14-3.07 (m, 2 H), 2.97-2.85 (m, 2 H), 1.99-1.90 (m, 2 H), 1.85-1.43 (m, 3 H)
¹³C NMR (75 MHz, CDCl₃) δ: 175.6, 168.2, 162.4, 160.5, 157.1, 149.3, 142.0, 141.2, 132.7, 129.7, 127.0, 121.5, 116.8, 107.7, 104.2, 95.2, 92.9, 65.0, 57.0, 56.5, 48.8
MS: 476 [M+H⁺]
Compound 31

(3-chloro-4-fluorophenyl)(4-fluoro-4-(((2-((5-methyl-6-(methylamino)pyridin-2-yl)oxy)ethyl)amino)methyl)piperidin-1-yl)methanone The title compound was prepared starting from the compound 50 (pre-compound-31).
MS: 453 [M+H⁺]
Compound 32

(3-chloro-4-fluorophenyl)(4-fluoro-4-(((2-(pyrimidin-2-yloxy)ethyl)amino)methyl)piperidin-1-yl)methanone The title compound was prepared starting from the compound (IIa-2) and amine (IIb-18)
¹H-NMR (300 MHz, CDCl₃) δ: 8.52-8.51 (m., 2H), 7.49-7.47 (m., 1H), 7.29-7.28 (m., 1H), 7.20-7.16 (m., 1H), 6.97-6.94 (m., 1H), 4.51 (br. s., 1H), 4.48-4.45 (t., J=5.0 Hz, 2H), 3.73-3.15 (m., 3H), 3.08-3.05 (t., J=5.3 Hz, 2H), 2.85 (m., 2H), 2.01 (br. s. 2H) 1.77-1.50 (m., 3H).
MS: 411 [M+H⁺]
Compound 33

(3-chloro-4-fluorophenyl)(4-fluoro-4-(((2-(pyrimidin-5-yloxy)ethyl)amino)methyl)piperidin-1-yl)methanone The title compound was prepared starting from the compound (IIa-2) and amine (IIb-A-2)
¹H NMR (300 MHz, CDCl₃) δ: 8.85 (s, 1 H), 8.41 (s, 2 H), 7.47 (dd, J=2.1, 6.9 Hz, 1 H), 7.32-7.26 (m, 1 H), 7.21-7.12 (m, 1 H), 4.50 (br. s., 1 H), 4.16 (t, J=5.0 Hz, 2 H), 3.60 (br. s., 1 H), 3.46-3.12 (m, 2 H), 3.07 (t, J=5.0 Hz, 2 H), 2.91-2.78 (m, 2 H), 2.00 (br. s., 2 H), 1.79-1.55 (m, 3 H)

¹³C NMR (75 MHz, CDCl₃) δ: 168.1, 160.5, 157.1, 152.8, 151.7, 143.6, 132.8, 129.7, 127.1, 116.8, 95.5, 93.2, 68.3, 57.5, 57.2, 48.9

MS: 411 [M+H⁺]

Compound 34

(3-chloro-4-fluorophenyl)(4-fluoro-4-(((2-(pyrimidin-4-yloxy)ethyl)amino)methyl)piperidin-1-yl)methanone The title compound was prepared starting from the compound (IIa-2) and amine (IIb-19)

MS: 411 [M+H⁺]

Compound 35

(3-chloro-4-fluorophenyl)(4-fluoro-4-(((2-((5-methylpyrimidin-2-yl)oxy)ethyl)amino)methyl)piperidin-1-yl)methanone The title compound was prepared starting from the compound (IIa-2) and amine (IIb-20)

¹H-NMR (CDCl₃) δ: 8.32 (s, 2H), 7.49-7.47 (m, 1H), 7.32-7.28 (m, 1H), 7.20-7.16 (m, 1H), 4.54 (br s, 1H), 4.44-4.41 (t, J=5.0 Hz, 2H), 3.60-3.16 (m, 3H), 3.06-3.02 (t, J=5.3 Hz, 2H), 2.86 (m, 2H), 2.25 (s, 3H), 2.04 (br s, 2H) 1.81-1.52 (m, 3H).

MS: 425 [M+H⁺]

Compound 36

(3-chloro-4-fluorophenyl)(4-fluoro-4-(((2-(pyrazin-2-yloxy)ethyl)amino)methyl)piperidin-1-yl)methanone The title compound was prepared starting from the compound (IIa-2) and amine (IIb-B-2)

¹H NMR (300 MHz, CDCl₃) δ: 8.22 (d, J=1.3 Hz, 1 H), 8.11 (d, J=2.8 Hz, 1 H), 8.06 (dd, J=1.4, 2.7 Hz, 1 H), 7.47 (dd, J=2.1, 6.9 Hz, 1 H), 7.32-7.26 (m, 1 H), 7.21-7.12 (m, 1 H), 4.63-4.36 (m, 3 H), 3.59 (br. s., 1 H), 3.27 (br. s., 2 H), 3.04 (t, J=5.3 Hz, 2 H), 2.90-2.77 (m, 2 H), 2.00 (br. s., 2 H), 1.64 (br. s., 3 H)

¹³C NMR (75 MHz, CDCl₃) δ: 168.1, 160.3, 157.1, 140.5, 136.7, 135.9, 132.9, 129.7, 127.1, 121.5, 116.8, 95.5, 93.2, 65.7, 57.4, 57.1, 48.9

MS: 411 [M+H⁺]

Compound 37

(3-chloro-4-fluorophenyl)(4-fluoro-4-(((2-(pyridazin-4-yloxy)ethyl)amino)methyl)piperidin-1-yl)methanone The title compound was prepared starting from the compound (IIa-2) and amine (IIb-A-1)

¹H NMR (300 MHz, CDCl₃) δ: 7.88 (d, J=3.1 Hz, 1 H), 7.76 (d, J=7.7 Hz, 1 H), 7.46 (dd, J=2.1, 6.9 Hz, 1 H), 7.31-7.24 (m, 1 H), 7.22-7.14 (m, 1 H), 6.42 (dd, J=3.2, 7.8 Hz, 1 H), 4.48 (br. s., 1 H), 4.08-4.00 (m, 2 H), 3.59 (br. s., 1 H), 3.42-3.14 (m, 2 H), 3.13-3.05 (m, 2 H), 2.81-2.67 (m, 2 H), 1.94 (br. s., 2 H), 1.70 (br. s., 3 H)

¹³C NMR (75 MHz, CDCl₃) δ: 168.1, 160.5, 157.1, 150.1, 142.1, 132.7, 129.7, 127.1, 121.6, 117.0, 116.6, 95.4, 93.1, 59.5, 57.3, 57.0, 48.9

MS: 411 [M+H⁺]

Compound 38

(3-chloro-4-fluorophenyl)(4-fluoro-4-(((2-(pyridazin-3-yloxy)ethyl)amino)methyl)piperidin-1-yl)methanone The title compound was prepared starting from the compound (IIa-2) and amine (IIb-21)

MS: 411 [M+H⁺]

Compound 39

(3-chloro-4-fluorophenyl)(4-fluoro-4-(((2-((3-methoxyphenyl)thio)ethyl)amino)methyl)piperidin-1-yl)methanone The title compound was prepared starting from the compound (IIa-2) and amine (IIb-23)

¹H NMR (300 MHz, CDCl₃) δ: 7.48 (dd, J=1.9, 7.1 Hz, 1 H), 7.32-7.26 (m, 1 H), 7.18 (dt, J=6.4, 8.3 Hz, 2 H), 6.95-6.90 (m, 1 H), 6.90-6.88 (m, 1 H), 6.73 (ddd, J=1.0, 2.5, 8.3 Hz, 1 H), 4.62-4.37 (m, 1 H), 3.79 (s, 3 H), 3.54 (br. s., 1 H), 3.44-3.11 (m, 2 H), 3.09-3.02 (m, 2 H), 2.91-2.84 (m, 2 H), 2.80-2.69 (m, 2 H), 2.07-1.89 (m, 2 H), 1.60 (br. s., 3 H)

¹³C NMR (75 MHz, CDCl₃) δ: 168.1, 160.4, 159.8, 157.1, 137.0, 132.9, 129.8, 127.0, 121.6, 121.4, 116.8, 115.0, 111.8, 95.4, 93.1, 57.1, 56.8, 55.3, 48.7, 34.0

MS: 455 [M+H⁺]

Compound 40

(3-chloro-4-fluorophenyl)(4-fluoro-4-(((2-(pyridin-2-ylthio)ethyl)amino)methyl)piperidin-1-yl)methanone The title compound was prepared starting from the compound (IIa-2) and amine (IIb-22)

¹H NMR (300 MHz, CDCl₃) δ: 8.39 (td, J=1.2, 5.5 Hz, 1 H), 7.52-7.40 (m, 2 H), 7.32-7.26 (m, 1 H), 7.21-7.13 (m, 2 H), 6.97 (ddd, J=1.0, 5.0, 7.3 Hz, 1 H), 4.50 (br. s., 1 H), 3.59 (br. s., 1 H), 3.41-3.07 (m, 5 H), 2.96 (t, J=6.4 Hz, 2 H), 2.86-2.72 (m, 2 H), 1.97 (br. s., 2 H), 1.63 (br. s., 3 H)

¹³C NMR (75 MHz, CDCl₃) δ: 168.0, 160.4, 158.4, 157.1, 149.4, 135.9, 132.9, 129.7, 127.1, 122.5, 121.5, 119.5, 116.8, 95.5, 93.2, 57.0, 56.7, 49.4, 30.0

MS: 426 [M+H⁺]

Compound 41

(3,4-dichlorophenyl)(4-fluoro-4-(((2-phenoxyethyl)amino)methyl)piperidin-1-yl)methanone The title compound was prepared starting from the compound (IIa-1) and amine (IIb-1)

¹H NMR (300 MHz, CDCl₃) δ: 7.54-7.45 (m, 2 H), 7.33-7.26 (m, 2 H), 7.23 (dd, J=2.1, 8.2 Hz, 1 H), 7.00-6.86 (m, 3 H), 4.52 (br. s., 1 H), 4.07 (t, J=5.1 Hz, 2 H), 3.58 (br. s., 1 H), 3.44-3.10 (m, 2 H), 3.03 (t, J=5.1 Hz, 2 H), 2.91-2.78 (m, 2 H), 2.02 (br. s., 2 H), 1.61 (s, 3 H)

MS: 426 [M+H⁺]

Compound 42

(3,4-dichlorophenyl)(4-fluoro-4-(((2-(3-fluorophenoxy)ethyl)amino)methyl)piperidin-1-yl)methanone The title compound was prepared starting from the compound (IIa-1) and amine (IIb-4)

¹H NMR (300 MHz, CDCl₃) δ: 7.57-7.42 (m, 2 H), 7.26-7.17 (m, 2 H), 6.73-6.55 (m, 3 H), 4.52 (br. s., 1 H), 4.04 (t, J=5.1 Hz, 2 H), 3.59 (br. s., 1 H), 3.44-3.10 (m, 2 H), 3.03 (t, J=5.0 Hz, 2 H), 2.91-2.75 (m, 2 H), 2.01 (br. s., 2 H), 1.62 (br. s., 3 H)

MS: 444 [M+H$^+$]

Compound 43

(4-(((2-(3-chlorophenoxy)ethyl)amino)methyl)-4-fluoropiperidin-1-yl)(3,4-dichlorophenyl)methanone The title compound was prepared starting from the compound (IIa-1) and amine (IIb-3)

$^1$H NMR (300 MHz, CDCl$_3$) δ: 7.53-7.46 (m, 2 H), 7.25-7.15 (m, 2 H), 6.97-6.87 (m, 2 H), 6.78 (ddd, J=1.0, 2.4, 8.3 Hz, 1 H), 4.52 (br. s., 1 H), 4.04 (t, J=5.1 Hz, 2 H), 3.59 (br. s., 1 H), 3.46-3.12 (m, 2 H), 3.02 (t, J=5.1 Hz, 2 H), 2.91-2.76 (m, 2 H), 2.00 (d, J=12.3 Hz, 2 H), 1.61 (br. s., 3 H)

MS: 460 [M+H$^+$]

Compound 44

(4-(((2-((1H-indol-4-yl)oxy)ethyl)amino)methyl)-4-fluoropiperidin-1-yl)(3-chloro-4-fluorophenyl)methanone The title compound was prepared starting from the compound (IIa-2) and amine (IIb-24)

$^1$H NMR (300 MHz, CD$_3$OD) δ: 7.57 (dd, J=1.8, 7.0 Hz, 1 H), 7.40-7.27 (m, 2 H), 7.13-7.06 (m, 1 H), 7.03-6.96 (m, 2 H), 6.53-6.47 (m, 2 H), 4.41 (br. s., 1 H), 4.22 (t, J=5.3 Hz, 2 H), 3.67-3.33 (m, 2 H), 3.27-3.14 (m, 1 H), 3.09 (t, J=5.3 Hz, 2 H), 2.97-2.85 (m, 2 H), 2.04 -1.69 (m, 4 H) NH protons not detected $^{19}$F NMR (282 MHz, CDCl$_3$) δ: −112.58 (s, 1F), −166.43 (s, 1F)

$^{13}$C NMR (75 MHz, CD$_3$OD) δ: 168.5, 152.1, 137.8, 135.9, 135.5, 133.0, 129.3, 127.2, 122.6, 121.6, 121.0, 118.8, 116.5, 104.7, 99.9, 98.1, 66.9, 56.7, 56.2, 48.9

MS: 448 [M+H$^+$]

Compound 45

(3-chloro-4-fluorophenyl)(4-(((2-(3-(dimethylamino)phenoxy)ethyl)amino)methyl)-4-fluoropiperidin-1-yl)methanone The title compound was prepared starting from the compound (IIa-2) and amine (IIb-25)

$^1$H NMR (300 MHz, CDCl$_3$) δ: 7.48 (dd, J=2.1, 6.7 Hz, 1 H), 7.34-7.25 (m, 1 H), 7.22-7.07 (m, 2 H), 6.40-6.32 (m, 1 H), 6.31-6.22 (m, 2 H), 4.50 (br. s., 1 H), 4.06 (t, J=5.0 Hz, 2 H), 3.60 (br. s., 1 H), 3.47-3.08 (m, 2 H), 3.02 (t, J=5.0 Hz, 2 H), 2.93 (s, 6 H), 2.84 (d, J=19.9 Hz, 2 H), 2.00 (br. s., 2 H), 1.87-1.47 (m, 3 H)

$^{13}$C NMR (75 MHz, CDCl$_3$) δ: 168.1, 160.4, 159.8, 157.1, 152.0, 132.9, 129.7, 127.1, 121.5, 116.8, 105.9, 101.9, 99.6, 95.5, 93.2, 67.0, 57.4, 57.1, 49.4, 40.6

MS: 452 [M+H$^+$]

Compound 46

(3-chloro-4-fluorophenyl)(4-fluoro-4-(((2-(3-(trifluoromethyl)phenoxy)ethyl)amino)methyl)piperidin-1-yl)methanone The title compound was prepared starting from the compound (IIa-2) and amine (IIb-26)

$^1$H NMR (300 MHz, CDCl$_3$) δ: 7.48 (dd, J=2.1, 6.7 Hz, 1 H), 7.42-7.34 (m, 1 H), 7.33-7.26 (m, 1 H), 7.24-7.16 (m, 2 H), 7.13 (d, J=3.5 Hz, 1 H), 7.06 (dd, J=2.9, 8.2 Hz, 1 H), 4.48 (br. s., 1 H), 4.09 (t, J=5.0 Hz, 2 H), 3.75-3.48 (m, 1 H), 3.47-3.10 (m, 2 H), 3.05 (t, J=5.0 Hz, 2 H), 2.91-2.76 (m, 2 H), 2.07-1.95 (m, 2 H), 1.83-1.44 (m, 3 H)

$^{13}$C NMR (75 MHz, CDCl$_3$) δ: 168.1, 160.5, 158.9, 157.1, 132.9, 130.0, 129.7, 127.1, 121.5, 117.9, 117.6, 116.9, 116.6, 111.3, 95.5, 93.2, 67.7, 57.5, 57.2, 49.1

MS: 477 [M+H$^+$]

Compound 47

3-(2-(((1-(3-chloro-4-fluorobenzoyl)-4-fluoropiperidin-4-yl)methyl)amino)ethoxy)benzamide The title compound was prepared starting from the compound (IIa-2) and amine (IIb-27)

$^1$H NMR (300 MHz, CDCl$_3$) δ: 7.46 (dd, J=1.8, 7.0 Hz, 1 H), 7.42-7.37 (m, 1 H), 7.35-7.23 (m, 3 H), 7.20-7.11 (m, 1 H), 7.04 (td, J=2.9, 5.9 Hz, 1 H), 6.43-6.04 (m, 2 H), 4.49 (br. s., 1 H), 4.09 (t, J=5.3 Hz, 2 H), 3.58 (br. s., 1 H), 3.45-3.08 (m, 2 H), 3.02 (t, J=5.3 Hz, 2 H), 2.83 (d, J =19.9 Hz, 2 H), 1.98 (br. s., 3 H), 1.81-1.48 (m, 2 H)

$^{19}$F NMR (282 MHz, CDCl$_3$) δ: −112.58 (s, 1F), −166.41 (s, 1F)

MS: 452 [M+H$^+$]

Compound 48

2-(2-(((1-(3-chloro-4-fluorobenzoyl)-4-fluoropiperidin-4-yl)methyl)amino)ethoxy)benzamide The title compound was prepared starting from the compound (IIa-2) and amine (IIb-28)

$^1$H NMR (300 MHz, DMSO-d$_6$) δ: 7.95 (s, 1 H), 7.81 (dd, J=1.8, 7.6 Hz, 1 H), 7.65 (dd, J=1.8, 7.0 Hz, 1 H), 7.54 (br. s., 1 H), 7.50-7.37 (m, 3 H), 7.12 (d, J=8.2 Hz, 1 H), 7.00 (t, J=7.9 Hz, 1 H), 4.33-4.07 (m, 3 H), 3.38 (br. s., 1 H), 3.27-2.97 (m, 2 H), 2.93 (t, J=5.3 Hz, 2 H), 2.81-2.66 (m, 2 H), 2.13 (br. s., 1 H), 1.96-1.64 (m, 4 H)

$^{13}$C NMR (75 MHz, DMSO-d$_6$) δ: 167.2, 166.8, 159.7, 157.2, 134.4, 132.9, 131.3, 129.7, 128.2, 123.1, 121.0, 120.2, 117.4, 113.8, 96.7, 94.4, 68.5, 56.9, 56.6, 49.0

MS: 452 [M+H$^+$]

Compound 49 (Pre-compound 26)

(4-(((2-((6-(benzyl(methyl)amino)pyridin-2-yl)oxy)ethyl)amino)methyl)-4-fluoropiperidin-1-yl)(3-chloro-4-fluorophenyl)methanone The title compound was prepared starting from the compound (IIa-2) and amine (IIb-C-6).

1H-NMR (300 MHz, CDCl$_3$) δ: 7.15-7.49 (4 m, 9 H), 6.00-6.05 (dd, 2 H), 4.79 (s, 2 H), 4.48 (bs, 1 H), 4.32 (t, 2 H), 3.02-3.62 (m, 4 H), 3.00 (s, 3 H), 2.95 (t, 2 H), 1.52-2.02 (m, 4 H).

MS: 530 [M+H$^+$]

Compound 50 (Pre-compound 31)

(4-(((2-((6-(benzyl(methyl)amino)-5-methylpyridin-2-yl)oxy)ethyl)amino)methyl)-4-fluoropiperidin-1-yl)(3-chloro-4-fluorophenyl)methanone The title compound was prepared starting from the compound (IIa-2) and amine (IIb-C-5)

MS: 544 [M+H$^+$]

Compound 51

(3-chloro-4-fluorophenyl)(4-fluoro-4-(((2-(2-(methylamino)phenoxy)ethyl)amino)methyl)piperidin-1-yl)methanone The title compound was prepared starting from the compound (IIa-2) and amine (IIb-D-1)

¹H NMR (300 MHz, CDCl₃) δ: 7.52-7.44 (m, 1 H), 7.34-7.26 (m, 1 H), 7.23-7.12 (m, 1 H), 6.96-6.87 (m, 1 H), 6.78 (dd, J=1.5, 7.9 Hz, 1 H), 6.64 (dq, J=1.8, 7.8 Hz, 2 H), 4.50 (br. s., 1 H), 4.09 (t, J=5.3 Hz, 2 H), 3.60 (br. s., 1 H), 3.45-3.13 (m, 2 H), 3.05 (t, J=5.0 Hz, 2 H), 2.90-2.75 (m, 5 H), 2.00 (br. s., 3 H), 1.64 (m., J=15.8 Hz, 3 H)
¹⁹F NMR (282 MHz, CDCl₃) δ: −112.58 (s, 1F), −166.62 (s, 1F)
MS: 438 [M+H⁺]

Compound 52

(3-chloro-4-fluorophenyl)(4-fluoro-4-(((2-(3-(methylamino)phenoxy)ethyl)amino)methyl)piperidin-1-yl)methanone The title compound was prepared from the compound 75.
¹H NMR (300 MHz, CDCl₃) δ: 7.48 (dd, J=1.8, 7.0 Hz, 1 H), 7.33-7.25 (m, 1 H), 7.19 (td, J=8.3, 11.6 Hz, 2 H), 6.86-6.77 (m, 2 H), 6.74-6.65 (m, 1 H), 4.51 (br. s., 1 H), 4.04 (t, J=5.3 Hz, 2 H), 3.58 (br. s., 1 H), 3.35 (br. s., 1 H), 3.23 (s, 3 H), 3.02 (t, J=5.0 Hz, 2 H), 2.91-2.75 (m, 2 H), 2.00 (br. s., 2 H), 1.64 (br. s., 3 H)
¹⁹F NMR (282 MHz, CDCl₃) δ: −114.75 (s, 1F), −166.64 (s, 1F)
¹³C NMR (75 MHz, CDCl₃) δ: 169.0, 160.0, 156.1, 150.7, 129.7, 129.3, 128.8, 127.1, 122.5, 111.6, 105.9, 102.8, 98.9, 95.6, 93.3, 67.0, 57.5, 57.2, 56.2, 49.4
MS: 438 [M+H⁺]

Compound 53

(3-chloro-4-fluorophenyl)(4-fluoro-4-(((2-(phenylamino)ethyl)amino)methyl)piperidin-1-yl)methanone The title compound was prepared starting from the compound (IIa-2) and amine (IIb-29)
¹H NMR (300 MHz, CDCl₃) δ: 7.48 (dd, J=1.8, 7.0 Hz, 1 H), 7.33-7.24 (m, 1 H), 7.22-7.13 (m, 3 H), 6.76-6.67 (m, 1 H), 6.66-6.58 (m, 2 H), 4.51 (br. s., 1 H), 3.60 (br. s., 1 H), 3.35 (d, J=15.8 Hz, 1 H), 3.24-3.17 (m, 2 H), 3.17-3.02 (m, 1 H), 2.91 (t, J=5.6 Hz, 2 H), 2.85-2.71 (m, 2 H), 2.02 (br. s., 3 H), 1.84-1.41 (m, 3 H)
¹³C NMR (75 MHz, CDCl₃) δ: 168.1, 160.5, 157.1, 148.3, 129.7, 129.3, 127.1, 127.1, 117.6, 116.8, 113.0, 95.4, 93.2, 57.1, 56.9, 48.9, 43.3
MS: 408 [M+H⁺]

Compound 54

(3-chloro-4-fluorophenyl)(4-fluoro-4-(((2-(pyridin-2-ylamino)ethyl)amino)methyl)piperidin-1-yl)methanone The title compound was prepared starting from the compound (IIa-2) and amine (IIb-30)
¹H NMR (300 MHz, CDCl₃) δ: 8.08-8.00 (m, 1 H), 7.47 (dd, J=2.1, 6.7 Hz, 1 H), 7.44-7.35 (m, 1 H), 7.32-7.26 (m, 1 H), 7.20-7.11 (m, 1 H), 6.55 (dd, J=5.3, 6.4 Hz, 1 H), 6.39 (d, J=8.2 Hz, 1 H), 5.10 (br. s., 1 H), 4.48 (br. s., 1 H), 3.57 (br. s., 1 H), 3.40-3.08 (m, 4 H), 3.00 (br. s., 1 H), 2.89 (t, J=5.9 Hz, 2 H), 2.78 (d, J=1.0 Hz, 1 H), 2.67 (br. s., 1 H), 2.01 (s, 2 H), 1.59 (d, J=17.0 Hz, 2 H)
¹⁹F NMR (282 MHz, CDCl₃) δ: −112.61 (s, 1F); −166.72 (s, 1F)
MS: 409 [M+H⁺]

Compound 55

(3-chloro-4-fluorophenyl)(4-fluoro-4-(((3-(pyridin-2-yl)propyl)amino)methyl)piperidin-1-yl)methanone The title compound was prepared starting from the compound (IIa-2) and amine (IIb-31)
¹H NMR (300 MHz, CDCl₃) δ: 8.53-8.43 (m, 1 H), 7.57 (dt, J=1.8, 7.6 Hz, 1 H), 7.46 (dd, J=1.8, 7.0 Hz, 1 H), 7.32-7.24 (m, 1 H), 7.21-7.04 (m, 3 H), 4.47 (br. s., 1 H), 3.57 (br. s., 1 H), 3.44-3.05 (m, 2 H), 2.80 (dd, J=7.9, 15.5 Hz, 3 H), 2.73-2.60 (m, 3 H), 2.07-1.84 (m, 4 H), 1.69 (br. s., 3 H)
¹⁹F NMR (282 MHz, CDCl₃) δ: −112.68 (s, 1F), −166.56 (s, 1F)
¹³C NMR (75 MHz, CDCl₃) δ: 168.0, 161.7, 160.4, 157.1, 149.2, 136.3, 132.9, 129.7, 127.1, 122.8, 121.0, 116.8, 95.5, 93.2, 57.5, 57.2, 49.8, 35.9, 29.9
MS: 408 [M+H⁺]

Compound 56

4-(2-(((1-(3-chloro-4-fluorobenzoyl)-4-fluoropiperidin-4-yl)methyl)amino)ethoxy)indolin-2-one The title compound was prepared starting from the compound (IIa-2) and amine (IIb-32)
MS: 464 [M+H⁺]

Compound 57

(3-chloro-4-fluorophenyl)(4-fluoro-4-(((2-(indolin-4-yloxy)ethyl)amino)methyl)piperidin-1-yl)methanone The title compound was prepared starting from the compound (IIa-2) and amine (IIb-33)
¹H NMR (300 MHz, CDCl₃) δ: 7.48 (dd, J=2.3, 7.0 Hz, 1 H), 7.35-7.26 (m, 1 H), 7.23-7.11 (m, 1 H), 6.97 (t, J=7.9 Hz, 1 H), 6.29 (dd, J=7.9, 14.4 Hz, 2 H), 4.51 (br. s., 1 H), 4.08 (t, J=5.0 Hz, 2 H), 3.56 (t, J=8.5 Hz, 3 H), 3.47-3.08 (m, 2 H), 3.06-2.93 (m, 4 H), 2.91-2.76 (m, 2 H), 2.02 (br. s., 2 H), 1.85-1.44 (m, 2 H) NH protons not detected
¹⁹F NMR (282 MHz, CDCl₃) δ: −112.63 (s, 1F), −166.68 (s, 1F)
MS: 450 [M+H⁺]

Compound 58

N-(6-(2-(((1-(3-chloro-4-fluorobenzoyl)-4-fluoropiperidin-4-yl)methyl)amino)ethoxy)pyridin-2-yl)acetamide The title compound was prepared starting from the compound (IIa-2) and amine (IIb-F-3)
¹H NMR (300 MHz, CDCl₃) δ: 7.78 (br. s., 1 H), 7.71 (d, J=7.6 Hz, 1 H), 7.56 (t, J=7.9 Hz, 1 H), 7.46 (dd, J=1.8, 7.0 Hz, 1 H), 7.33-7.26 (m, 1 H), 7.21-7.08 (m, 1 H), 6.45 (d, J=8.8 Hz, 1 H), 4.50 (br. s., 1 H), 4.27 (t, J=5.0 Hz, 2 H), 3.58 (br. s., 1 H), 3.47-3.03 (m, 2 H), 2.98 (t, J=5.3 Hz, 2 H), 2.88-2.71 (m, 2 H), 2.17 (s, 3 H), 1.95 (br. s., 3 H), 1.79-1.45 (m, 2 H)
¹⁹F NMR (282 MHz, CDCl₃) δ: −112.57 (s, 1F), −166.35 (s, 1F)
¹³C NMR (75 MHz, CDCl₃) δ: 168.4, 168.0, 162.3, 160.4, 157.1, 148.9, 141.0, 132.9, 129.7, 127.1, 121.5, 116.8, 105.7, 95.5, 93.3, 65.4, 57.4, 57.1, 49.2, 24.7
MS: 467 [M+H⁺]

Compound 59

(3-chloro-4-fluorophenyl)(4-fluoro-4-(((3-phenylpropyl)amino)methyl)piperidin-1-yl)methanone The title compound was prepared starting from the compound (IIa-2) and amine (IIb-34)

¹H NMR (300 MHz, CDCl₃) δ: 7.48 (dd, J=2.3, 7.0 Hz, 1 H), 7.34-7.23 (m, 3 H), 7.22-7.10 (m, 4 H), 4.50 (br. s., 1 H), 3.60 (d, J=19.9 Hz, 1 H), 3.46-3.08 (m, 2 H), 2.80-2.60 (m, 6 H), 2.09-1.90 (m, 2 H), 1.87-1.45 (m, 5 H)
¹³C NMR (75 MHz, CDCl₃) δ: 168.0, 160.4, 157.1, 142.0, 132.9, 129.7, 128.3, 127.1, 125.8, 121.5, 116.8, 95.5, 93.2, 57.6, 57.3, 49.8, 33.5, 31.5
MS: 407 [M+H⁺]
Compound 60

(3-chloro-4-fluorophenyl)(4-(((2-((2,2-dimethyl-2,3-dihydrobenzofuran-7-yl)oxy)ethyl)amino)methyl)-4-fluoropiperidin-1-yl)methanone The title compound was prepared starting from the compound (IIa-2) and amine (IIb-35)
¹H NMR (300 MHz, CDCl₃) δ: 7.48 (dd, J=1.8, 7.0 Hz, 1 H), 7.32-7.25 (m, 1 H), 7.22-7.13 (m, 1 H), 6.81-6.70 (m, 3 H), 4.50 (br. s., 1 H), 4.15 (t, J=5.0 Hz, 2 H), 3.71-3.50 (m, 1 H), 3.48-3.08 (m, 2 H), 3.06-2.96 (m, 4 H), 2.83 (d, J=19.9 Hz, 2 H), 1.99 (br. s., 2 H), 1.83 (br. s., 3 H), 1.49 (s, 6 H)
¹³C NMR (75 MHz, CDCl₃) δ: 168.0, 160.4, 157.1, 147.9, 143.5, 132.9, 129.7, 128.6, 127.1, 120.3, 118.1, 116.8, 113.7, 95.5, 93.2, 87.3, 69.0, 57.4, 57.1, 49.2, 43.2, 28.3
MS: 479 [M+H⁺]
Compound 61

(3-chloro-4-fluorophenyl)(4-fluoro-4-(((2-(2-fluorophenoxy)ethyl)amino)methyl)piperidin-1-yl)methanone The title compound was prepared starting from the compound (IIa-2) and amine (IIb-36)
¹H NMR (300 MHz, CDCl₃) δ: 7.51-7.45 (m, 1 H), 7.33-7.25 (m, 1 H), 7.21-7.13 (m, 1 H), 7.11-7.01 (m, 2 H), 7.01-6.86 (m, 2 H), 4.50 (br. s., 1 H), 3.58 (br. s., 1 H), 3.47-3.14 (m, 2 H), 3.05 (t, J=5.0 Hz, 2 H), 2.86 (d, J=19.9 Hz, 2 H), 2.00 (s, 2 H), 1.83-1.51 (m, 3 H)
¹³C NMR (75 MHz, CDCl₃) δ: 160.4, 157.1, 154.5, 151.2, 146.8, 132.9, 129.7, 127.1, 124.3, 121.5, 116.9, 116.6, 116.4, 116.1, 115.3, 95.5, 93.2, 69.2, 57.4, 57.1, 49.2
MS: 427 [M+H⁺]
Compound 62

(3-chloro-4-fluorophenyl)(4-fluoro-4-(((2-(2-chlorophenoxy)ethyl)amino)methyl)piperidin-1-yl)methanone The title compound was prepared starting from the compound (IIa-2) and amine (IIb-37)
¹H NMR (300 MHz, CDCl₃) δ: 7.47 (dd, J=1.8, 7.0 Hz, 1 H), 7.35 (dd, J=1.8, 7.6 Hz, 1 H), 7.32-7.26 (m, 1 H), 7.24-7.12 (m, 2 H), 6.96-6.84 (m, 2 H), 4.49 (br. s., 1 H), 4.12 (t, J=5.0 Hz, 2 H), 3.59 (d, J=5.9 Hz, 1 H), 3.45-3.12 (m, 2 H), 3.07 (t, J=5.0 Hz, 2 H), 2.95-2.80 (m, 2 H), 2.00 (br. s., 2 H), 1.84 (s, 1 H), 1.77-1.53 (m, 2 H)
¹³C NMR (75 MHz, CDCl₃) δ: 168.0, 160.4, 157.1, 154.2, 133.0, 130.3, 129.7, 127.8, 127.0, 121.7, 116.9, 116.6, 113.7, 95.5, 93.2, 68.9, 57.4, 57.1, 49.0
MS: 443 [M+H⁺]
Compound 63

(3-chloro-4-fluorophenyl)(4-fluoro-4-(((2-(m-tolyloxy)ethyl)amino)methyl)piperidin-1-yl)methanone The title compound was prepared starting from the compound (IIa-2) and amine (IIb-38)
¹H NMR (300 MHz, CD₃OD) δ: 7.59 (dd, J=1.8, 7.0 Hz, 1 H), 7.45-7.37 (m, 1 H), 7.36-7.28 (m, 1 H), 7.17-7.06 (m, 1 H), 6.78-6.66 (m, 3 H), 4.43 (br. s., 1 H), 4.05 (t, J=5.3 Hz, 2 H), 3.68-3.49 (m, 1 H), 3.39 (br. s., 1 H), 3.28-3.09 (m, J=5.3 Hz, 1 H), 3.00 (t, J=5.6 Hz, 2 H), 2.91-2.79 (m, 2 H), 2.29 (s, 3 H), 2.06-1.62 (m, 4 H) NH proton not detected
¹³C NMR (75 MHz, CD₃OD) δ: 168.6, 160.4, 158.8, 157.0, 139.2, 133.0, 129.1, 127.3, 121.3, 121.0, 116.6, 114.9, 111.1, 95.0, 92.7, 66.5, 56.7, 56.4, 48.8, 20.2
MS: 423 [M+H⁺]
Compound 64

(3-chloro-4-fluorophenyl)(4-fluoro-4-(((2-(4-fluorophenoxy)ethyl)amino)methyl)piperidin-1-yl)methanone The title compound was prepared starting from the compound (IIa-2) and amine (IIb-39)
¹H NMR (300 MHz, CDCl₃) δ: 7.48 (dd, J=2.3, 7.0 Hz, 1 H), 7.33-7.24 (m, 1 H), 7.22-7.11 (m, 1 H), 7.01-6.90 (m, 2 H), 6.88-6.78 (m, 2 H), 4.51 (br. s., 1 H), 4.02 (t, J=5.3 Hz, 2 H), 3.62 (d, J=19.3 Hz, 1 H), 3.48-3.10 (m, 2 H), 3.01 (t, J=5.0 Hz, 2 H), 2.83 (d, J=19.9 Hz, 2 H), 2.06-1.94 (m, 2 H), 1.83-1.45 (m, 3 H)
¹³C NMR (75 MHz, CDCl₃) δ: 168.1, 160.5, 158.9, 157.1, 155.7, 154.9, 132.9, 129.7, 127.1, 121.5, 116.8, 115.8, 115.5, 95.5, 93.2, 68.0, 57.5, 57.2, 49.3
MS: 427 [M+H⁺]
Compound 65

(3-chloro-4-fluorophenyl)(4-fluoro-4-(((2-(4-chlorophenoxy)ethyl)amino)methyl)piperidin-1-yl)methanone The title compound was prepared starting from the compound (IIa-2) and amine (IIb-40)
¹H NMR (300 MHz, CDCl₃) δ: 7.48 (dd, J=2.1, 6.7 Hz, 1 H), 7.34-7.12 (m, 4 H), 6.87-6.77 (m, 2 H), 4.50 (br. s., 1 H), 4.02 (t, J=5.0 Hz, 2 H), 3.74-3.49 (m, 1 H), 3.24 (br. s., 2 H), 3.02 (t, J=5.0 Hz, 2 H), 2.91-2.74 (m, 2 H), 2.00 (br. s., 2 H), 1.88-1.44 (m, 3 H)
¹³C NMR (75 MHz, CDCl₃) δ: 168.1, 160.5, 157.4, 157.1, 132.9, 129.7, 129.3, 127.1, 125.8, 121.5, 116.9, 116.6, 115.7, 95.5, 93.2, 67.7, 57.5, 57.2, 49.2
MS: 443 [M+H⁺]
Compound 66

(3-chloro-4-fluorophenyl)(4-fluoro-4-(((2-((6-methoxypyridin-2-yl)oxy)ethyl)amino)methyl)piperidin-1-yl)methanone The title compound was prepared starting from the compound (IIa-2) and amine (IIb-41)
¹H NMR (300 MHz, CDCl₃) δ: 7.52-7.43 (m, 2 H), 7.33-7.23 (m, 1 H), 7.22-7.12 (m, 1 H), 6.29 (dd, J=1.5, 7.9 Hz, 2 H), 4.49 (br. s., 1 H), 4.41-4.32 (m, 2 H), 3.88 (s, 3 H), 3.67-3.53 (m, 1 H), 3.46-3.10 (m, 2 H), 3.02 (t, J=5.3 Hz, 2 H), 2.90-2.76 (m, 2 H), 1.99 (br. s., 2 H), 1.83-1.56 (m, 3 H)
¹³C NMR (75 MHz, CDCl₃) δ: 168.1, 163.0, 162.6, 160.4, 157.1, 141.0, 132.9, 129.7, 127.1, 121.5, 116.8, 101.2, 95.4, 93.1, 65.2, 57.4, 57.1, 53.4, 49.2
MS: 440 [M+H⁺]
Compound 67

(3-chloro-4-fluorophenyl)(4-fluoro-4-(((2-((5-methoxypyridin-2-yl)oxy)ethyl)amino)methyl)piperidin-1-yl)methanone The title compound was prepared starting from the compound (IIa-2) and amine (IIb-42)

¹H NMR (300 MHz, CDCl₃) δ: 7.77 (d, J=2.9 Hz, 1 H), 7.47 (dd, J=1.8, 7.0 Hz, 1 H), 7.33-7.26 (m, 1 H), 7.23-7.12 (m, 2 H), 6.67 (d, J=9.4 Hz, 1 H), 4.51 (br. s., 1 H), 4.33 (t, J=5.3 Hz, 2 H), 3.80 (s, 3 H), 3.70-3.48 (m, 1 H), 3.45-3.06 (m, 2 H), 3.00 (t, J=5.3 Hz, 2 H), 2.83 (d, J=1.0 Hz, 2 H), 2.01 (br. s., 2 H), 1.62 (br. s., 3 H)
¹⁹F NMR (282 MHz, CDCl₃) δ: −112.66 (s, 1F), −166.47 (s, 1F)
¹³C NMR (75 MHz, DMSO-d₆) δ: 163.3, 155.7, 153.4, 146.4, 128.2, 126.3, 125.0, 122.3, 121.9, 116.8, 112.0, 106.3, 90.8, 88.5, 60.5, 52.7, 52.4, 51.5, 44.6
MS: 440 [M+H⁺]
Compound 68

(3-chloro-4-fluorophenyl)(4-fluoro-4-(((2-((4-methoxypyridin-2-yl)oxy)ethyl)amino)methyl)piperidin-1-yl)methanone The title compound was prepared starting from the compound (IIa-2) and amine (IIb-B-3)
¹H NMR (300 MHz, CDCl₃) δ: 7.88 (d, J=6.4 Hz, 1 H), 7.44 (dd, J=2.1, 6.7 Hz, 1 H), 7.29-7.20 (m, 1 H), 7.19-7.08 (m, 1 H), 6.44 (dd, J=2.3, 5.9 Hz, 1 H), 6.17 (d, J=1.8 Hz, 1 H), 4.45 (br. s., 1 H), 4.37-4.28 (m, 2 H), 3.77 (s, 3 H), 3.67-3.45 (m, 1 H), 3.44-3.02 (m, 2 H), 2.97 (t, J=5.3 Hz, 2 H), 2.79 (d, J=19.9 Hz, 2 H), 2.38 (br. s., 1 H), 1.97 (br. s., 2 H), 1.60 (d, J=17.0 Hz, 2 H)
¹³C NMR (75 MHz, CDCl₃) δ: 168.1, 165.5, 160.4, 157.1, 147.2, 132.7, 129.6, 127.1, 121.5, 116.8, 106.3, 95.3, 94.1, 93.0, 65.1, 57.2, 56.9, 55.2, 49.1
MS: 440 [M+H⁺]
Compound 69

(3-chloro-4-fluorophenyl)(4-fluoro-4-(((2-((5-fluoropyridin-2-yl)oxy)ethyl)amino)methyl)piperidin-1-yl)methanone The title compound was prepared starting from the compound (IIa-2) and amine (IIb-43)
¹H NMR (300 MHz, CDCl₃) δ: 7.96 (d, J=2.9 Hz, 1 H), 7.47 (dd, J=2.1, 6.7 Hz, 1 H), 7.38-7.26 (m, 2 H), 7.22-7.11 (m, 1 H), 6.70 (dd, J=3.2, 9.1 Hz, 1 H), 4.50 (br. s., 1 H), 4.39-4.28 (m, 2 H), 3.74-3.48 (m, 1 H), 3.46-3.06 (m, 2 H), 3.00 (t, J=5.3 Hz, 2 H), 2.90-2.74 (m, 2 H), 2.01 (br. s., 2 H), 1.62 (br. s., 3 H)
¹⁹F NMR (282 MHz, CDCl₃) δ: −112.63 (s, 1F), −139.15 (s, 1F), −166,59 (s, 1F)
¹³C NMR (75 MHz, CDCl₃) δ: 168.1, 160.1, 157.1, 153.8, 133.3, 132.9, 129.7, 127.1, 126.6, 121.5, 116.8, 111.5, 95.5, 93.2, 65.7, 57.4, 57.1, 49.1
MS: 428 [M+H⁺]
Compound 70

(3-chloro-4-fluorophenyl)(4-fluoro-4-(((2-((4-fluoropyridin-2-yl)oxy)ethyl)amino)methyl)piperidin-1-yl)methanone The title compound was prepared starting from the compound (IIa-2) and amine (IIb-44)
¹H NMR (300 MHz, CDCl₃) δ: 8.08 (dd, J=5.9, 8.8 Hz, 1 H), 7.47 (dd, J=1.8, 7.0 Hz, 1 H), 7.33-7.27 (m, 1 H), 7.23-7.11 (m, 1 H), 6.65 (ddd, J=2.3, 5.7, 7.8 Hz, 1 H), 6.43 (dd, J=2.3, 10.0 Hz, 1 H), 4.51 (br. s., 1 H), 4.44-4.34 (m, 2 H), 3.58 (br. s., 1 H), 3.47-3.07 (m, 2 H), 3.01 (t, J=5.3 Hz, 2 H), 2.83 (d, J=19.9 Hz, 2 H), 2.01 (br. s., 2 H), 1.58 (br. s., 3 H)
¹⁹F NMR (282 MHz, CDCl₃) δ: −101.70 (s, 1F), −112.61 (s, 1F), −166.62 (s, 1F)
¹³C NMR (75 MHz, CDCl₃) δ: 171.9, 168.3, 165.7, 160.4, 148.8, 132.9, 129.7, 127.1, 121.5, 116.8, 106.2, 97.8, 95.5, 93.2, 65.9, 57.4, 57.1, 49.1
MS: 428 [M+H⁺]
Compound 71

(3-chloro-4-fluorophenyl)(4-fluoro-4-(((2-((6-(trifluoromethyl)pyridin-2-yl)oxy)ethyl)amino)methyl)piperidin-1-yl)methanone The title compound was prepared starting from the compound (IIa-2) and amine (IIb-45)
¹H NMR (300 MHz, CDCl₃) δ: 7.70 (t, J=7.6 Hz, 1 H), 7.47 (dd, J=1.8, 7.0 Hz, 1 H), 7.33-7.26 (m, 1 H), 7.25-7.12 (m, 2 H), 6.91 (d, J=8.2 Hz, 1 H), 4.64-4.35 (m, 3 H), 3.59 (br. s., 1 H), 3.47-3.09 (m, 2 H), 3.04 (t, J=5.6 Hz, 2 H), 2.84 (d, J=19.9 Hz, 2 H), 2.00 (br. s., 2 H), 1.87-1.53 (m, 3 H)
¹³C NMR (75 MHz, CDCl₃) δ: 168.1, 163.6, 160.4, 157.1, 139.5, 132.9, 129.7, 127.1, 121.5, 116.8, 114.6, 113.3, 95.5, 93.2, 65.7, 57.3, 57.0, 48.9
MS:478 [M+H⁺]
Compound 72

(3-chloro-4-fluorophenyl)(4-(((2-((6-chloropyridin-2-yl)oxy)ethyl)amino)methyl)-4-fluoropiperidin-1-yl)methanone The title compound was prepared starting from the compound (IIa-2) and amine (IIb-46)
¹H NMR (300 MHz, CDCl₃) δ: 7.55-7.41 (m, 2 H), 7.33-7.25 (m, 1 H), 7.21-7.12 (m, 1 H), 6.88 (d, J=7.6 Hz, 1 H), 6.64 (d, J=8.2 Hz, 1 H), 4.50 (br. s., 1 H), 4.41-4.34 (m, 2 H), 3.60 (d, J=19.9 Hz, 1 H), 3.46-3.09 (m, 2 H), 3.04-2.95 (m, 2 H), 2.89-2.73 (m, 2 H), 1.99 (br. s., 2 H), 1.82-1.49 (m, 3 H)
¹³C NMR (75 MHz, CDCl₃) δ: 168.0, 163.3, 160.4, 157.1, 148.3, 140.7, 132.9, 129.7, 127.1, 121.5, 116.8, 116.5, 109.1, 95.5, 93.2, 65.8, 57.3, 57.0, 49.0
MS: 444 [M+H⁺]
Compound 73

(3-chloro-4-fluorophenyl)(4-(((2-((6-methylpyridin-2-yl)oxy)ethyl)amino)methyl)-4-fluoropiperidin-1-yl)methanone The title compound was prepared starting from the compound (IIa-2) and amine (IIb-47)
¹H NMR (300 MHz, CDCl₃) δ: 7.51-7.40 (m, 2 H), 7.32-7.26 (m, 1 H), 7.17 (t, J=8.5 Hz, 1 H), 6.71 (d, J=7.0 Hz, 1 H), 6.51 (d, J=8.2 Hz, 1 H), 4.48 (br. s., 1 H), 4.41-4.33 (m, 2 H), 3.58 (br. s., 1 H), 3.47-3.06 (m, 2 H), 3.01 (t, J=5.3 Hz, 2 H), 2.90-2.76 (m, 2 H), 2.42 (s, 3 H), 2.00 (br. s., 2 H), 1.85-1.52 (m, 3 H)
¹³C NMR (75 MHz, CDCl₃) δ: 168.0, 163.2, 160.4, 156.7, 138.9, 132.9, 129.7, 127.1, 121.5, 116.8, 115.9, 107.0, 95.5, 93.2, 65.0, 57.4, 57.1, 49.4, 24.1
MS: 424 [M+H⁺]
Compound 74

(3,4-dichlorophenyl)(4-fluoro-4-(((2-(pyridin-2-yloxy)ethyl)amino)methyl)piperidin-1-yl)methanone The title compound was prepared starting from the compound (IIa-1) and amine (IIb-11)

¹H NMR (300 MHz, CDCl₃) δ: 8.17-8.08 (m, 1 H), 7.61-7.53 (m, 1 H), 7.52-7.44 (m, 2 H), 7.23 (dd, J=1.8, 8.2 Hz, 1 H), 6.91-6.82 (m, 1 H), 6.77-6.69 (m, 1 H), 4.50 (br. s., 1 H), 4.43-4.34 (m, 2 H), 3.71-3.47 (m, 1 H), 3.47-3.07 (m, 2 H), 3.03 (t, J=5.3 Hz, 2 H), 2.84 (d, J=1.0 Hz, 2 H), 2.00 (br. s., 2 H), 1.61 (br. s., 3 H)

¹⁹F NMR (282 MHz, CDCl₃) δ: −166.55 (s, 1F)

¹³C NMR (75 MHz, CDCl₃) δ: 167.9, 163.6, 146.8, 138.7, 135.6, 134.1, 133.0, 130.6, 129.1, 126.2, 116.9, 111.0, 95.5, 93.2, 64.9, 57.3, 57.1, 49.2

MS: 426 [M+H⁺]

Compound 75 (Pre-compound 52)

(3,4-dichlorophenyl)(4-fluoro-4-(((2-(pyridin-2-yloxy)ethyl)amino)methyl)piperidin-1-yl)methanone The title compound was prepared starting from the compound (IIa-2) and amine (IIb-E-1)

¹H NMR (300 MHz, CDCl₃) δ: 7.48 (dd, J=1.8, 7.0 Hz, 1 H), 7.33-7.25 (m, 1 H), 7.19 (td, J=8.3, 11.6 Hz, 2 H), 6.86-6.77 (m, 2 H), 6.74-6.65 (m, 1 H), 4.51 (br. s., 1 H), 4.04 (t, J=5.3 Hz, 2 H), 3.58 (br. s., 1 H), 3.35 (br. s., 1 H), 3.23 (s, 3 H), 3.20-3.08 (m, 1 H), 3.02 (t, J=5.0 Hz, 2 H), 2.91-2.75 (m, 2 H), 2.00 (br. s., 2 H), 1.64 (br. s., 3 H), 1.45 (s, 9 H)

MS: 538 [M+H⁺]

In one embodiment, the present invention also concerns compounds 49 and 50 as intermediates for the preparation of compounds of general formula I.

49. (4-(((2-((6-(benzyl(methyl)amino)pyridin-2-yl)oxy)ethyl)amino)methyl)-4-fluoropiperidin-1-yl)(3-chloro-4-fluorophenyl)methanone 50. (4-(((2-((6-(benzyl(methyl)amino)-5-methylpyridin-2-yl)oxy)ethyl)amino)methyl)-4-fluoropiperidin-1-yl)(3-chloro-4-fluorophenyl)methanone Within the context of the present invention, the preferred compounds of formula (I) are:

1. (3-chloro-4-fluorophenyl)-4-fluoro-4-(((2-phenoxyethyl)amino)methyl)piperidin-1-yl)methanone
2. N-(3-(2-(((1-(3-chloro-4-fluorobenzoyl)-4-fluoropiperidin-4-yl)methyl)amino)ethoxy)phenyl)acetamide
3. N-(3-(2-(((1-(3,4-dichlorobenzoyl)-4-fluoropiperidin-4-yl)methyl)amino)ethoxy)phenyl)acetamide
5. (3-chloro-4-fluorophenyl)-4-fluoro-4-(((2-(3-fluorophenoxy)ethyl)amino)methyl)piperidin-1-yl)methanone
8. (3-chloro-4-fluorophenyl)-4-fluoro-4-(((2-(3-methoxyphenoxy)ethyl)amino)methyl)piperidin-1- yl)methanone
18. (3-chloro-4-fluorophenyl)-4-fluoro-4-(((2-(pyridin-2-yloxy)ethyl)amino)methyl)piperidin-1-yl)methanone
29. (3-chloro-4-fluorophenyl)-4-fluoro-4-(((2-((6-(pyrrolidin-1-yl)pyridin-2-yl)oxy)ethyl)amino)methyl)piperidin-1-yl)methanone
36. (3-chloro-4-fluorophenyl)-4-fluoro-4-(((2-(pyrazin-2-yloxy)ethyl)amino)methyl)piperidin-1-yl)methanone as well as their salts with pharmaceutically acceptable mineral or organic acids or hydrates.

The subject of the invention is also the pharmaceutical compositions containing, as active ingredient, at least one of the compounds of general formula (I) or one of its salts or hydrates of its salts in combination with one or more inert carriers or other pharmaceutically acceptable vehicles.

More particularly, the purpose of the invention is the use of a compound with formula (I) or one of its pharmaceutically acceptable salts according to this invention, for use as a drug that can be administrated orally, intravenously, or by an intraperitoneal or intramuscular route, or by any other route which permits to obtain an antidepressant effect according to this invention, or making patients suffering from major depression who were resistant to classical antidepressant treatments, sensitive to these treatments, or to obtain the required prevention or treatment in the previous uses.

Active substances of drugs or pharmaceutical compositions according to the invention may be in any of the oral galenic forms normally used including tablets, capsules and liquid preparations such as elixirs and suspensions containing various colour, taste and stabilisation masking substances.

To produce oral galenic forms according to the invention, the active substance may be mixed with various conventional materials such as starch, calcium carbonate, lactose, sucrose and dibasic calcium phosphate to facilitate the encapsulation process. Magnesium stearate as an additive, provides a useful lubrication function if necessary.

Active substances of pharmaceutical compositions according to the invention may be dissolved or present in suspension in a pharmaceutically acceptable sterile liquid such as sterile water, a sterile organic solvent or a mixture of these two liquids. Preferably, such a liquid is appropriate for parenteral injection.

When the active substance is sufficiently soluble, it can be dissolved in a normal saline solution such as a pharmaceutically acceptable sterile liquid; if it is not sufficiently soluble, it can be dissolved in aqueous solutions of an appropriate organic solvent, for example propylene glycol or polyethylene glycol. Aqueous propylene glycol containing 10 to 75% by weight of glycol is usually appropriate. In other examples, other compositions can be obtained by dispersing the active substance as a very fine concentrate in an aqueous carboxymethylic solution of starch cellulose or sodium, or in an appropriate oil, for example peanut oil.

Liquid pharmaceutical compositions such as sterile solutions or suspensions can be used for intramuscular, intraperitoneal or subcutaneous injections.

Preferably, the pharmaceutical composition is in the form of unit doses, for example such as tablets or capsules. In this form, the composition is subdivided into unit doses containing appropriate quantities of active substance; unit doses may be packaged compositions, for example powders, flasks or phials. The quantity of active substance in a unit dose of the composition may be modified or adjusted by 2 mg or less, or by 50 mg or more, depending on the particular need and the activity of the active substance.

The recommended oral dose of compounds with formula (I) for man may be from 0.01 to 100 mg/day and this dose may be administered in two to four separate doses.

Those skilled in the art also are aware that methods of administrating compounds according to this invention can change significantly. Apart from other oral administrations, slow release compositions may be preferred. Other administration methods may include but are not limited to intravenous injections, intramuscular and intraperitoneal injections, subcutaneous implants, and mouth, sublingual, transdermal, topic, rectal and intranasal administration.

The pharmaceutical compositions according to the invention may be, by way of example, compounds which can be administered orally, nasally, sublingually, rectally or parenterally. By way of example of compositions which can be administered orally, there may be mentioned tablets, gelatin capsules, granules, powders and oral solutions or suspensions. The formulations appropriate for the chosen form for administration are known and described for example in: Remington, The Science and Practice of Pharmacy, 19th edition, 1995, Mack Publishing Company.

The term "pharmaceutically acceptable" refers to molecular entities and compositions which have no adverse or allergic effect or any unwanted reaction when administered to humans. When used here, the term "pharmaceutically acceptable excipient" includes any diluents, adjuvants or excipients, such as preservatives, fillers, disintegrating agents, wetting agents, emulsifiers, dispersing agents, antibacterial or antifungal agents, or even agents which help delay intestinal and digestive absorption and resorption. The use of these media or carriers is well known to the person skilled in the art. The term "pharmaceutically acceptable salts" of a compound refers to the salts defined here and which possess the pharmacological activity of the parent compound.

Such salts include: acid addition salts formed with mineral acids, such as hydrochloric acid, hydrobromic acid, sulphuric acid, nitric acid, phosphoric acid and similar, or formed with organic salts, such as acetic acid, benzensulphonic acid, benzoic acid, camphorsulphonic acid, citric acid, ethanesulphonic acid, fumaric acid, glucoheptonic acid, gluconic acid, glutamic acid, glycolic acid, hydroxynaphtoic acid, 2-hydroxyethanesulphonic acid, lactic acid, maleic acid, malic acid, mandelic acid, methanesulphonic acid, muconic acid, 2-napthalenesulphonic acid, proprionic acid, salicylic acid, succinic acid, dibenzoyl-L-tartaric acid, tartric acid, p-toluenesulphonic acid, trimethylacetic acid, trifluoroacetic acid and similar.

The pharmaceutically acceptable salts also include solvent (solvates) addition forms or crystalline forms (polymorphs), such as defined here, of the same acid addition salt.

The effective dose of a compound of the invention varies according to numerous parameters such as for example the chosen route of administration, the weight, age, gender, state of progression of the pathology to be treated and the sensitivity of the individual to be treated. Consequently, the optimum dosage will have to be determined according to the parameters which are judged to be relevant by the specialist in the field.

Although the effective doses of a compound of the invention can vary in large proportions, the daily doses could be between 0.001 mg and 10 mg per kg of bodyweight of the individual to be treated.

A daily dose of a compound of the invention of between 0.01 mg and 1 mg per kg of bodyweight of the individual to be treated is however preferred.

The examples and the Figures described below are intended to illustrate the invention without in any way limiting its scope.

Binding Affinity and In Vivo Tests

The binding affinity of the compounds of the invention for 5-$HT_{1A}$ serotonin receptor, alpha1 adrenergic receptor and $D_2$ dopamine receptor were evaluated according to the testing procedure as depicted below:

Radioligand Binding Assay—Preparation of Test Compounds 10 mM stock solutions of tested compounds were prepared in DMSO. Serial dilutions of compounds were prepared in 96-well microplate in assay buffers using automated pipetting system epMotion 5070 (Eppendorf) or CyBio Felix (CyBio AG). Each compound was tested in 10 concentrations from $10^{-6}$ to $10^{-10}$ M (final concentration). In case of very high affinity, the test was repeated with the concentration range shifted to $10^{-8}$ to $10^{-13}$ M (final concentration).

5-$HT_{1A}$ Serotonin Receptor Binding Assay

Radioligand binding was performed using membranes from CHO-K1 cells stably transfected with the human 5-$HT_{1A}$ receptor. All assays were carried out in duplicates. 50 μL working solution of the tested compounds, 50 μL [3H]-8-OH-DPAT (final concentration 1 nM, Kd 0.8 nM) and 150 μL diluted membranes (10 μg protein per well) prepared in assay buffer (50 mM Tris-HCl, pH 7.4, 10 mM $MgCl_2$, 0.1 mM EDTA, 0.1% ascorbic acid) were transferred to polypropylene 96-well microplate using 96-wells pipetting station Rainin Liquidator (MettlerToledo). Serotonin (10 μM) was used to define nonspecific binding. Microplate was covered with a sealing tape, mixed and incubated for 60 minutes at 27° C. The reaction was terminated by rapid filtration through GF/C filter mate presoaked with 0.3% polyethyleneimine for 30 minutes. Ten rapid washes with 200 μL 50 mM Tris-HCl buffer (4° C., pH 7.4) were performed using automated harvester system Harvester-96 MACH III FM (Tomtec). The filter mates were dried at 37° C. in forced air fan incubator and then solid scintillator MeltiLex was melted on filter mates at 90° C. for 5 minutes. Radioactivity was counted in MicroBeta2 scintillation counter (PerkinElmer) at approximately 30% efficiency. Data were fitted to a one-site curve-fitting equation with Prism 6 (GraphPad Software) and Ki values were estimated from the Cheng-Prusoff equation.

Alpha1-adrenergic Receptor Binding Assay

Radioligand binding was performed using tissue (rat cortex). All assays were carried out in duplicates. 50 μL working solution of the tested compounds, 50 μL [3H]-prazosin (final concentration 0.2 nM, Kd 0.2 nM) and 150 μL tissue suspension prepared in assay buffer (50 mM Tris-HCl, pH 7.6) were transferred to polypropylene 96well microplate using 96wells pipetting station Rainin Liquidator (MettlerToledo). Phentolamine (10 μM) was used to define nonspecific binding. Microplate was covered with a sealing tape, mixed and incubated for 30 minutes at 30° C. The reaction was terminated by rapid filtration through GF/B filter mate. Ten rapid washes with 200 μL 50 mM Tris-HCl buffer (4° C., pH 7.6) were performed using automated harvester system Harvester-96 MACH III FM (Tomtec). The filter mates were dried at 37° C. in forced air fan incubator and soaked in 10 mL of liquid scintillation cocktail Ultima Gold MV (PerkinElmer, USA). After even distribution of scintillation cocktail filter bag was sealed. Radioactivity was counted in MicroBeta2 scintillation counter (PerkinElmer) at approximately 30% efficiency. Data were fitted to a one-site curve-fitting equation with Prism 6 (Graph Pad Software) and Ki values were estimated from the Cheng-Prusoff equation.

$D_2$ Dopamine Receptor Binding Assay

Radioligand binding was performed using membranes from CHO-K1 cells stably transfected with the human D2 receptor. All assays were carried out in duplicates. 50 μL working solution of the tested compounds, 50 μL [3H]-methylspiperon (final concentration 0.4 nM, Kd 0.4 nM) and 150 μL diluted membranes (10 μg protein per well) prepared in assay buffer (50 mM HEPES, pH 7.4, 50 mM NaCl, 5 mM $MgCl_2$, 0.5 mM EDTA) were transferred to polypropylene 96well microplate using 96wells pipetting station Rainin Liquidator (MettlerToledo). (+)-butaclamol (10 μM) was used to define nonspecific binding. Microplate was covered with a sealing tape, mixed and incubated for 60 minutes at 37° C. The reaction was terminated by rapid filtration through GF/C filter mate presoaked with 0.3% polyethyleneimine for 30 minutes. Ten rapid washes with 200 μL 50 mM Tris buffer (4° C., pH 7.4) were performed using automated harvester system Harvester-96 MACH III FM (Tomtec). The filter mates were dried at 37° C. in forced air fan incubator and then solid scintillator MeltiLex was melted on filter mates at 90° C. for 5 minutes. Radioactivity was counted in MicroBeta2 scintillation counter (PerkinElmer) at approximately 30% efficiency. Data were fitted to a one-site curve-fitting equation with Prism 6 (GraphPad Software) and Ki values were estimated from the Cheng-Prusoff equation.

5-$HT_{1A}$ Serotonin Receptor Agonist Efficacy Assay

A cellular aequorin-based functional assay was performed with recombinant CHO-K1 cells expressing mitochondrially targeted aequorin, human GPCR and the promiscuous G protein α16 for 5-HT1A. Assay was executed according to previously described protocol (Kolaczkowski et al., 2014). After thawing, cells were transferred to assay buffer (DMEM/HAM's F12 with 0.1% protease free BSA) and centrifuged. The cell pellet was resuspended in assay buffer and coelenterazine h was added at final concentrations of 5 μM. The cells suspension was incubated at 16° C., protected from light with constant agitation for 16 h and then diluted with assay buffer to the concentration of 100,000 cells/ml. After 1 h of incubation, 50 μl of the cells suspension was dispensed using automatic injectors built into the radiometric and luminescence plate counter MicroBeta2 LumiJET (PerkinElmer, USA) into white opaque 96-well microplates preloaded with test compounds. Immediate light emission generated following calcium mobilization was recorded for 30 s. In antagonist mode, after 25 min of incubation the reference agonist was added to the above assay mix and light emission was recorded again. Final concentration of the reference agonist was equal to EC80 (100 nM serotonin).

Forced Swim Test (FST) in Rats

The experiment was carried out according to a well-characterized method (Porsolt et al., 1978). On the first day of an experiment, the animals (n=7-8 per group) were gently individually placed in Plexiglas cylinders (40 cm high, 18 cm in diameter) containing water (15 cm deep) maintained at 23-25° C. for 15 min. On removal from water, the rats were placed for 30 min in a Plexiglas box under a 60 W incandescent filament bulb to dry. On the following day (24 h later), test compound was administered to rats by oral administration (p.o.) route 60 minutes before the rats were re-placed in the cylinder and the total duration of their immobility was recorded during the 5-min test period. The swimming behaviour entailed active swimming motions, e.g., moving horizontally around in the cylinder, and immobility was assigned when no additional activity was observed other than that necessary to keep the rat's head above the water. Fresh water was used for each animal. Data were analysed by One-way ANOVA, followed by Dunnet's post-hoc test for comparison with control (vehicle-treatment) group.

Developed formulas of compounds 1-75 are detailed below.

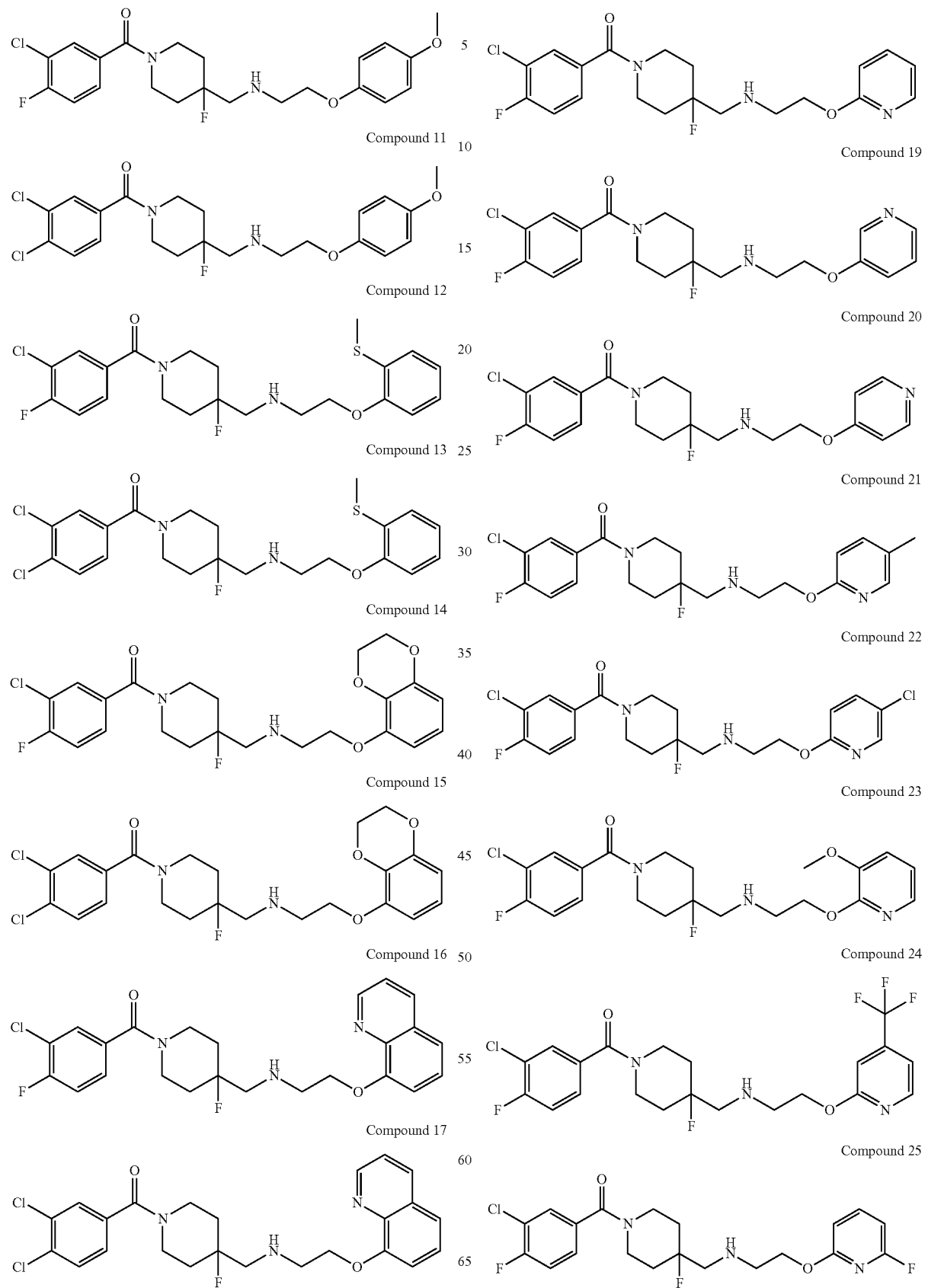

Compound 26
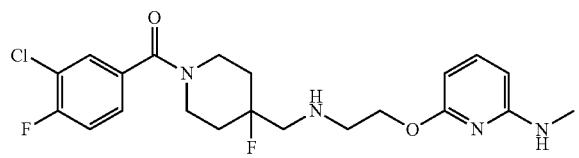
Compound 27
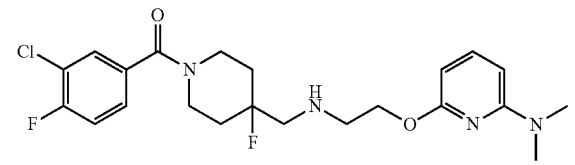
Compound 28
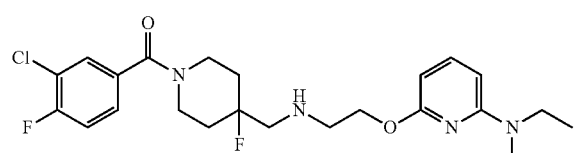
Compound 29
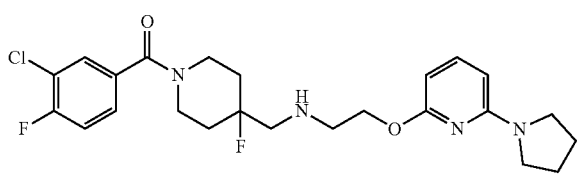
Compound 30
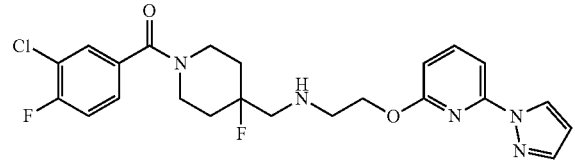
Compound 31
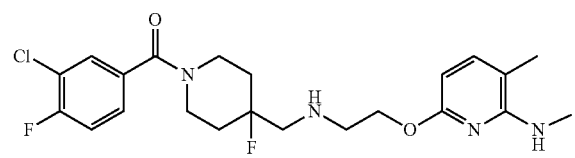
Compound 32
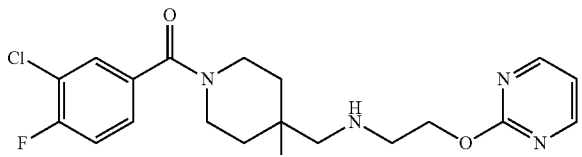
Compound 33
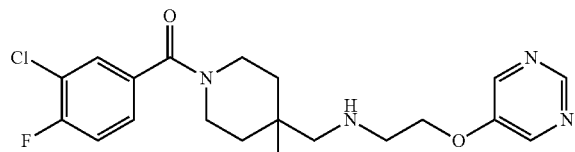
Compound 34
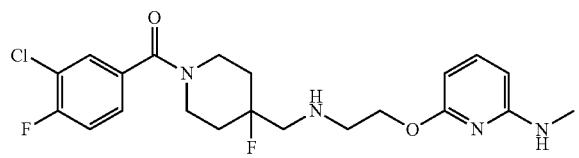
Compound 35
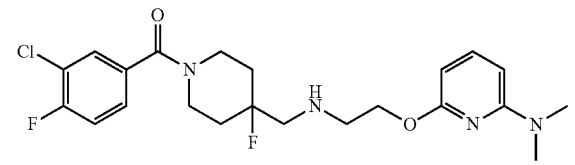
Compound 36
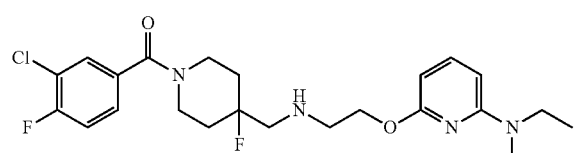
Compound 37
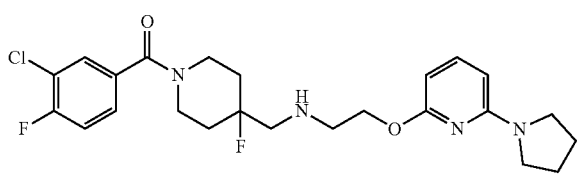
Compound 38
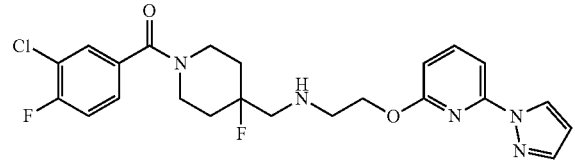
Compound 39
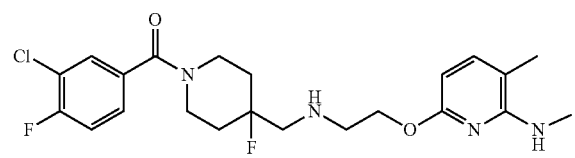
Compound 40
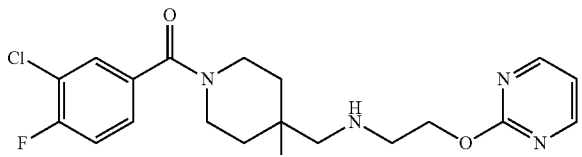
Compound 41
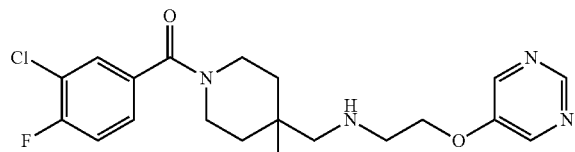

Compound 42
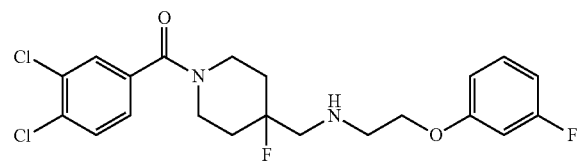
Compound 43
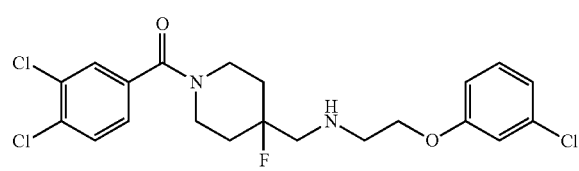
Compound 44
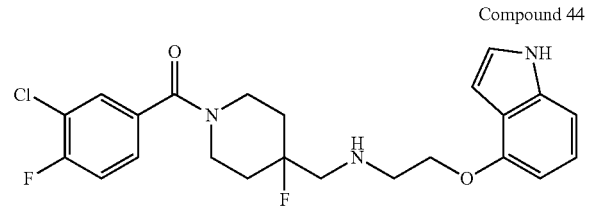
Compound 45
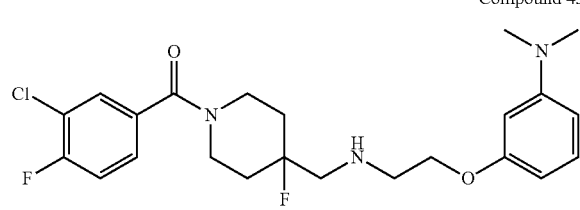
Compound 46
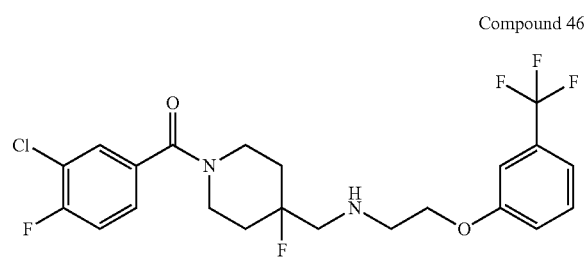
Compound 47
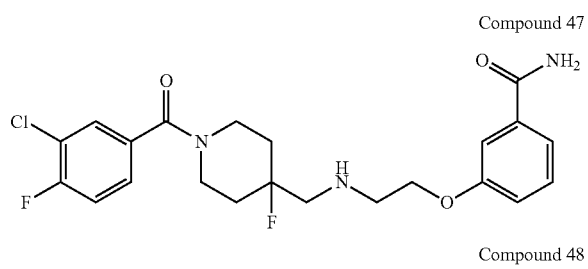
Compound 48
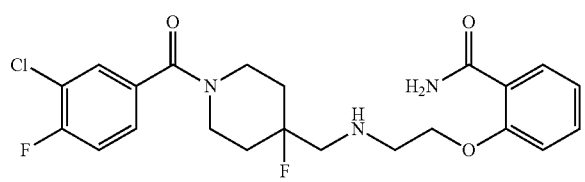
Compound 51
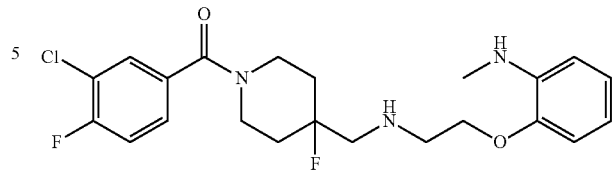
Compound 52
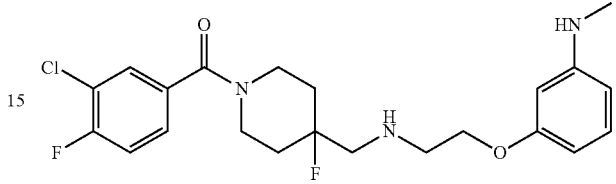
Compound 53
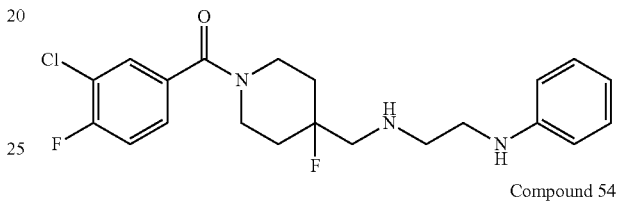
Compound 54
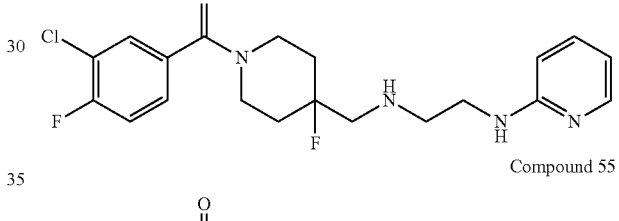
Compound 55
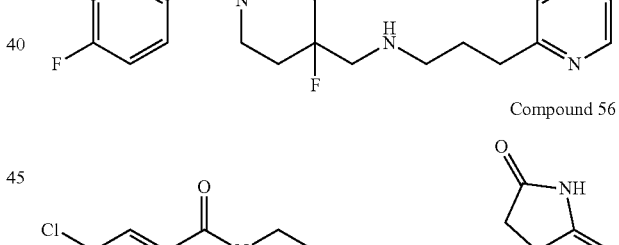
Compound 56
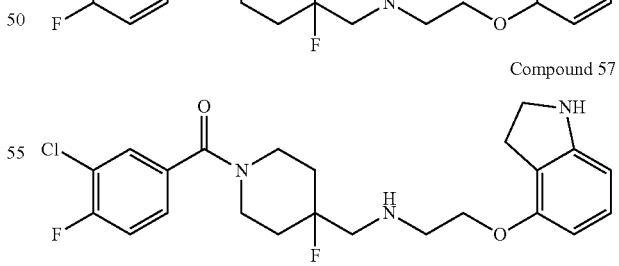
Compound 57
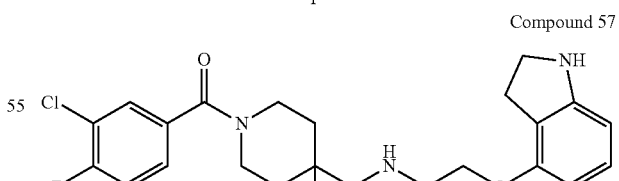
Compound 58
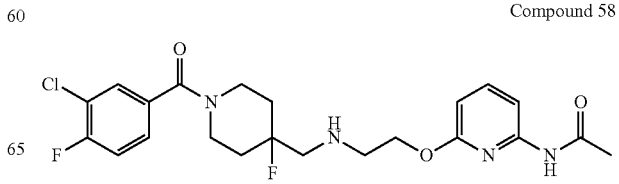

-continued
Compound 59
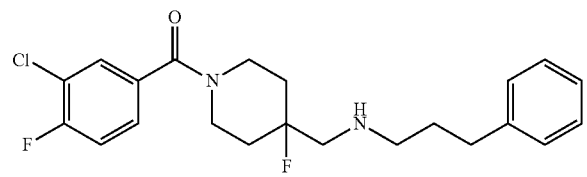
Compound 60
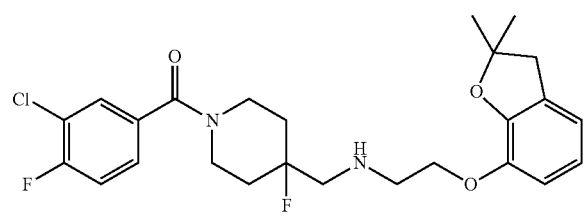
Compound 61
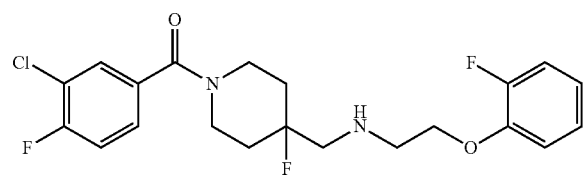
Compound 62
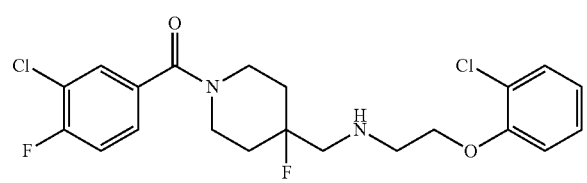
Compound 63
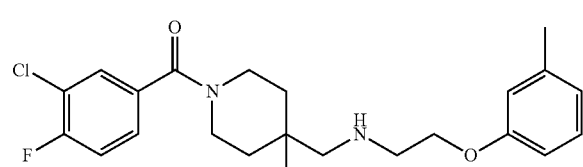
Compound 64
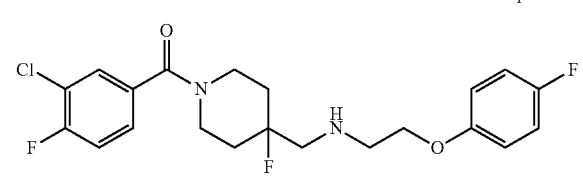
Compound 65
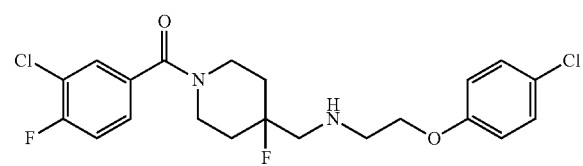
Compound 66
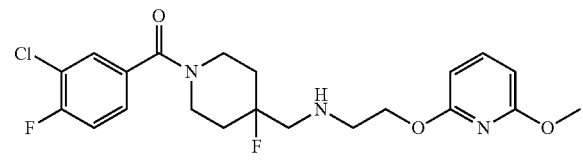
-continued
Compound 67
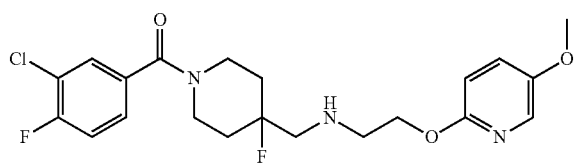
Compound 68
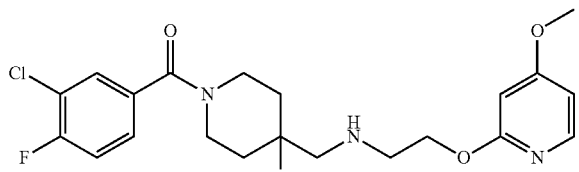
Compound 69
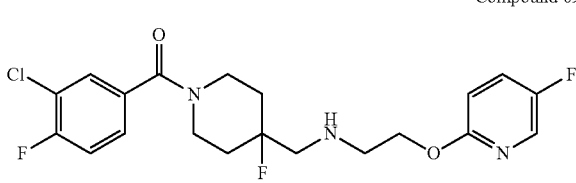
Compound 70
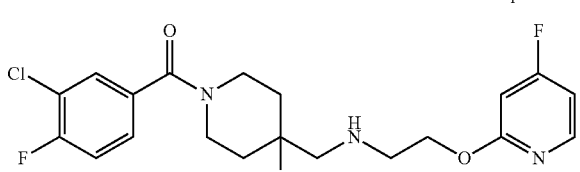
Compound 71
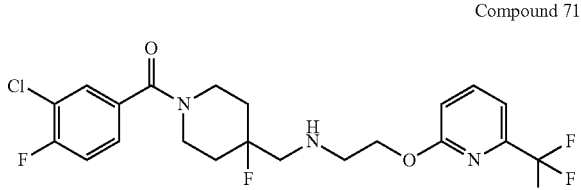
Compound 72
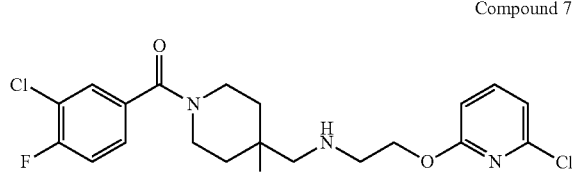
Compound 73
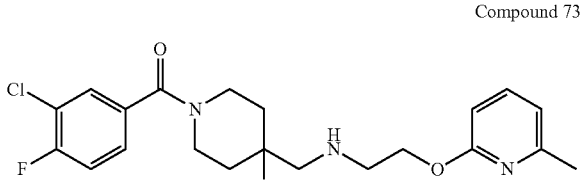
Compound 74
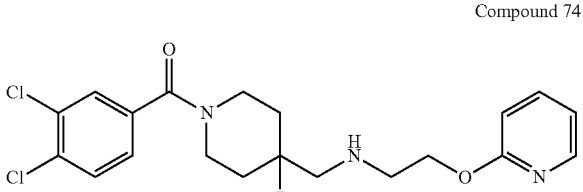

Compound 75

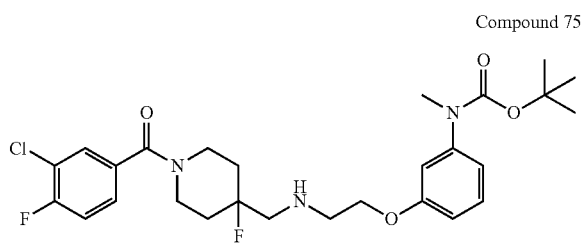

TABLE 1

Binding affinities of the compounds of the invention

| Compound | 5-HT$_{1A}$ receptor Ki (nM) | 5-HT$_{1A}$ 5-HT$_{1A}$ E$_{max}$ (%) | Alpha1 receptor Ki (nM) | D2 receptor Ki (nM) |
|---|---|---|---|---|
| 1 | 0.061 | 58% | 380 | >1000 |
| 2 | 0.083 | 96% | >1000 | >1000 |
| 3 | 0.073 | 86% | >1000 | >1000 |
| 4 | 0.043 | 69% | >1000 | >1000 |
| 5 | 0.023 | 57% | >1000 | >1000 |
| 6 | 0.035 | | 70 | 570 |
| 7 | 0.38 | | 46 | 450 |
| 8 | 0.052 | 67% | >1000 | >1000 |
| 9 | 0.057 | 57% | >1000 | >1000 |
| 10 | 8.6 | | >1000 | >1000 |
| 11 | 1.2 | | >1000 | >1000 |
| 12 | 0.029 | | 140 | >1000 |
| 13 | 0.50 | | 75 | 670 |
| 14 | 0.18 | | 190 | >1000 |
| 15 | 0.20 | | 190 | >1000 |
| 16 | 0.15 | 50% | 170 | >1000 |
| 17 | 0.45 | | 230 | 640 |
| 18 | 0.065 | 40% | 170 | >1000 |
| 19 | 1.7 | 91% | >1000 | >1000 |
| 21 | 5,2 | | >1000 | >1000 |
| 22 | 8.2 | | >1000 | >1000 |
| 23 | 0.40 | | 59 | 680 |
| 24 | 0.55 | 32% | >1000 | >1000 |
| 25 | 0.28 | 40% | 270 | >1000 |
| 26 | 0.08 | 107% | 320 | 850 |
| 27 | 0.08 | 94% | 300 | >1000 |
| 29 | 1.7 | 95% | 630 | >1000 |
| 30 | 2.7 | 39% | 290 | >1000 |
| 32 | 32 | | >1000 | >1000 |
| 35 | 12 | 23% | >1000 | >1000 |
| 36 | 0.57 | 47% | >1000 | >1000 |
| 39 | 0.7 | 31% | 33 | >1000 |
| 40 | 1.8 | | >1000 | >1000 |
| 44 | 0.1 | 73% | 110 | >1000 |
| 45 | 0.2 | 84% | >1000 | >1000 |
| 46 | 0.3 | 81% | >1000 | >1000 |
| 47 | 0.1 | 98% | >1000 | >1000 |
| 48 | 0.2 | 92% | >1000 | >1000 |
| 51 | 0.4 | 47% | 900 | >1000 |
| 52 | 0.2 | 88% | >1000 | >1000 |
| 53 | 1.3 | 62% | >1000 | >1000 |
| 54 | 2.7 | 72% | 40 | >1000 |
| 55 | 2.5 | 45% | 200 | >1000 |
| 58 | 0.5 | 77% | >1000 | >1000 |
| 59 | 2.0 | 45% | >1000 | >1000 |
| 60 | 0.01 | 89% | 25 | 25 |
| 61 | 0.3 | 81% | >1000 | >1000 |
| 62 | 0.2 | | >1000 | >1000 |
| 63 | 0.5 | 51% | >1000 | >1000 |
| 64 | .8 | 77% | >1000 | >1000 |
| 65 | 5.5 | 71% | >1000 | >1000 |
| 66 | 0.5 | 77% | >1000 | >1000 |
| 67 | 1.1 | 54% | 400 | >1000 |
| 68 | 0.09 | 67% | 770 | >1000 |
| 69 | 0.25 | 84% | >1000 | >1000 |
| 70 | 0.05 | 76% | 900 | >1000 |
| 71 | 3.7 | 45% | >1000 | >1000 |
| 72 | 0.2 | 62% | 180 | >1000 |
| 73 | 0.9 | 78% | 110 | >1000 |
| 74 | 0.2 | 74% | 130 | >1000 |
| Buspirone | 5.0 | 9% | >5000 | 240 |
| Befiradol | 0.4 | 92% | >1000 | >1000 |
| 8-OH-DPAT | 0.9 | 31% | >1000 | >1000 |

The results highlighted in Table 1 demonstrate the high affinity of the compounds of the invention for 5-HT$_{1A}$ receptors while exhibiting low affinity for alpha1 and D2 receptors. They also show that the efficacy of the compounds of the present invention are equivalent to or greater than those of the best known agonists (WO 98/22459) and far superior to that of the reference agonists (Buspirone and 8-OH-DPAT).

FIG. 1 shows the effects of Compound 18 in the rat Forced Swim Test

Compound 18 was tested in the rat Forced Swim Test, an in vivo behavioural model of potential antidepressant activity (Porsolt et al. 1978). In this test, control rats (i.e. that received only vehicle) exhibited immobility times of over 200 seconds (see Table 2). In contrast, rats that were treated with 18 showed decreased immobility. Statistical analysis (One-way ANOVA) indicated a highly significant effect of the treatment (F(4.33)=43.736; p<0,0001) with a lowest significant dose of 0.16 mg/kg p.o. Immobility behaviour was further dose-dependently reduced and almost abolished at the dose of 2.5 mg/kg p.o. Such activity is much greater in terms of effect size than that of commonly-used antidepressants such as imipramine or paroxetine(Koek et al., 1998).These data show that 18 has potent in vivo antidepressant-like effects that are exhibited by oral administration route, as is desirable for a pharmacotherapeutic agent to be used in a clinical environment. *p<0.01; **p<0.0001

These results suggest that compounds (I) are therefore potentially useful for treating disorders sensitive to a serotoninergic regulation controlled by the 5-HT$_{1A}$ receptors such as, for instance, the treatment and/or prevention of depression, the treatment and/or prevention of major depressive disorders, the treatment and/or prevention of anxiety, and the treatment and/or prevention of bipolar depression.

REFERENCES

Albert, P. R., Vahid-Ansari, F., Luckhart, C., 2014. Serotonin-prefrontal cortical circuitry in anxiety and depression phenotypes: pivotal role of pre- and post-synaptic 5-HT1A receptor expression. Frontiers in behavioral neuroscience. 8, 199.

Celada, P., Bortolozzi, A., Artigas, F., 2013. Serotonin 5-HT1A receptors as targets for agents to treat psychiatric disorders: rationale and current status of research. CNS drugs. 27, 703-16.

Hamik, A., et al., 1990. Analysis of tandospirone (SM-3997) interactions with neurotransmitter receptor binding sites. Biological psychiatry. 28, 99-109.

Iderberg, H., et al., 2015. Activity of serotonin 5-HT receptor 'biased agonists' in rat models of Parkinson's disease and I-DOPA-induced dyskinesia. Neuropharmacology. 93C, 52-67.

Koek, W., et al., 1998. F 11440, a potent, selective, high efficacy 5-HT1A receptor agonist with marked anxiolytic and antidepressant potential. J Pharmacol Exp Ther. 287, 266-83.

Koek, W., et al., 2001. 5-HT1A receptor activation and antidepressant-like effects: F 13714 has high efficacy and marked antidepressant potential. Eur J Pharmacol. 420, 103-12.

Kolaczkowski, M., et al., 2014. Novel arylsulfonamide derivatives with 5-HT(6)/5-HT(7) receptor antagonism targeting behavioral and psychological symptoms of dementia. Journal of medicinal chemistry. 57, 4543-57.

McCreary, A. C., Newman-Tancredi, A., 2015. Serotonin 5-HT1A Receptors and Antipsychotics—An Update in Light of New Concepts and Drugs. Current pharmaceutical design. 21, 3725-31.

Ohno, Y., et al., 2015. New insight into the therapeutic role of the serotonergic system in Parkinson's disease. Progress in neurobiology. 134, 104-21.

Pauwels, P. J., Van Gompel, P., Leysen, J. E., 1993. Activity of serotonin (5-HT) receptor agonists, partial agonists and antagonists at cloned human 5-HT1A receptors that are negatively coupled to adenylate cyclase in permanently transfected HeLa cells. Biochemical pharmacology. 45, 375-83.

Porsolt, R. D., et al., 1978. Behavioural despair in rats: a new model sensitive to antidepressant treatments. European journal of pharmacology. 47, 379-91.

Prinssen, E. P., Colpaert, F. C., Koek, W., 2002. 5-HT1A receptor activation and anti-cataleptic effects: high-efficacy agonists maximally inhibit haloperidol-induced catalepsy. Eur J Pharmacol. 453, 217-21.

The invention claimed is:
1. Compound according to formula (I):

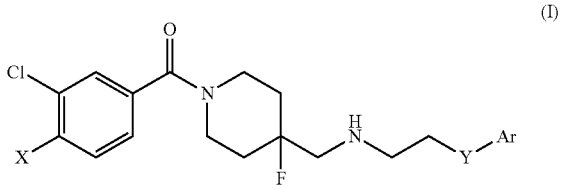

or a pharmaceutically acceptable salt and/or solvate thereof, wherein:
X represents a halo;
Y represents O, S or NH; and
Ar is selected from the group consisting of aryl, heterocycloalkyl-fused aryl and heteroaryl, said group being optionally substituted.

2. Compound according to claim 1, wherein:
X represents a halo;
Y represents O, S or NH; and
Ar is selected from the group consisting of aryl, heterocycloalkyl-fused aryl and heteroaryl, said group being optionally substituted with one or several groups selected from: halo, —$OR_1$, —$NR_2R_3$, —$NR_4COR_5$, —$NR_6C(O)OR_7$, —$SR_8$, —$S(O)R_9$, —$SO_2R_{10}$, —$SO_2NR_{11}R_{12}$, —$OCOR_{13}$, $CO_2R_{14}$, —$CONR_{15}R_{16}$, —$OCO_2R_{17}$, —$OCONR_{18}R_{19}$, —$COR_{20}$, —$CF_3$, nitro (—$NO_2$), and cyano (—CN) or a group consisting of —($C_1$-$C_6$) alkyl group, heteroaryl and heterocycloalkyl; with $R_1$ to $R_{20}$ being, independently of one another, H, ($C_1$-$C_6$)alkyl group.

3. A pharmaceutical composition comprising the compound according to claim 1.

4. A method of treating depression, which comprises administering a compound according to claim 1 to a patient in need thereof.

5. A method of treating major depressive disorders, which comprises administering a compound according to claim 1 to a patient in need thereof.

6. A method of treating bipolar type major depression according to the DSM IV, which comprises administering a compound according to claim 1 to a patient in need thereof.

7. A method of treating depression with severity evaluated with a score of more than 26 using the HAMD ("Hamilton Depression Scale") scale, or with a score of more than 35 on the MADRS (Montgomery and Asberg Depression Rating Scale) scale, which comprises administering a compound according to claim 1 to a patient in need thereof.

8. A method of treating movement disorders, which comprises administering a compound according to claim 1 to a patient in need thereof.

9. A method of treating L-DOPA-induced dyskinesia, which comprises administering a compound according to claim 1 to a patient in need thereof.

10. A method of treating anxiety, which comprises administering a compound according to claim 1 to a patient in need thereof.

11. Pharmaceutical compositions containing, as active ingredient, a compound according to claim 1, in combination with one or more inert carriers or other pharmaceutically acceptable vehicles.

12. A pharmaceutical composition comprising the compound to claim 2.

13. A method of treating depression, which comprises administering a compound according to claim 2 to a patient in need thereof.

14. A method of treating major depressive disorders, which comprises administering a compound according to claim 2 to a patient in need thereof.

15. A method of treating bipolar type major depression according to the DSM IV, which comprises administering a compound according to claim 2 to a patient in need thereof.

16. The method according to claim 6, wherein the bipolar type major depression according to the DSM IV is a major recurrent depressive disorder.

17. The method according to claim 15, wherein the bipolar type major depression according to the DSM IV is a major recurrent depressive disorder.

18. A method of treating depression with severity evaluated with a score of more than 26 using the HAMD ("Hamilton Depression Scale") scale, or with a score of more than 35 on the MADRS (Montgomery and Asberg Depression Rating Scale) scale, which comprises administering a compound according to claim 2 to a patient in need thereof.

19. A method of treating movement disorders, which comprises administering a compound according to claim 2 to a patient in need thereof.

20. A method of treating anxiety, which comprises administering a compound according to claim 2 to a patient in need thereof.

21. Compound according to claim 1, wherein X is Cl or F.

22. Compound according to claim 1, wherein Y is O or S.

23. Compound according to claim 2, wherein X is Cl or F.

24. Compound according to claim 2, wherein Y is O or S.

25. Compound according to claim 2, wherein Ar is substituted with one or two groups.

26. Compound according to claim 2, wherein selected said —($C_1$-$C_6$) alkyl group is methyl.

27. Compound according to claim 2, wherein said heteroaryl is pyrazole.

28. Compound according to claim 2, wherein said heterocycloalkyl is pyrrolidine.

29. Compound according to claim 2, wherein $R_1$ to $R_{20}$ being, independently of one another, H, methyl or ethyl.

* * * * *